United States Patent
Shiba et al.

(10) Patent No.: US 9,937,176 B2
(45) Date of Patent: Apr. 10, 2018

(54) PYRAZOLOTHIAZOLE COMPOUND AND MEDICINE COMPRISING SAME

(71) Applicant: NIPPON SHINYAKU CO., LTD., Kyoto-shi, Kyoto (JP)

(72) Inventors: Yoshinobu Shiba, Kyoto (JP); Satoshi Akiyama, Kyoto (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 0 days.

(21) Appl. No.: 15/505,767

(22) PCT Filed: Sep. 2, 2015

(86) PCT No.: PCT/JP2015/074935
§ 371 (c)(1),
(2) Date: Feb. 22, 2017

(87) PCT Pub. No.: WO2016/035814
PCT Pub. Date: Mar. 10, 2016

(65) Prior Publication Data
US 2017/0252341 A1 Sep. 7, 2017

(30) Foreign Application Priority Data
Sep. 2, 2014 (JP) ................... 2014-177969

(51) Int. Cl.
*A61K 31/506* (2006.01)
*C07D 513/04* (2006.01)
*A61K 31/25* (2006.01)
*A61K 31/135* (2006.01)
*A61K 31/095* (2006.01)
*A61K 31/381* (2006.01)

(52) U.S. Cl.
CPC .......... *A61K 31/506* (2013.01); *A61K 31/095* (2013.01); *A61K 31/135* (2013.01); *A61K 31/25* (2013.01); *A61K 31/381* (2013.01); *C07D 513/04* (2013.01)

(58) Field of Classification Search
CPC .. A61K 31/506; A61K 31/095; A61K 31/135; A61K 31/25; A61K 31/381; C07D 513/04
See application file for complete search history.

(56) References Cited

U.S. PATENT DOCUMENTS

| 4,918,073 A | 4/1990 | Ruger et al. |
|---|---|---|
| 5,082,847 A | 1/1992 | Pascal et al. |
| 7,528,143 B2 * | 5/2009 | Noronha ............. C07D 239/42 514/275 |
| 8,592,629 B2 | 11/2013 | Bell et al. |

FOREIGN PATENT DOCUMENTS

| JP | 2011-136925 A | 7/2011 |
|---|---|---|
| WO | 2004/006926 A1 | 1/2004 |
| WO | 2005/066156 A1 | 7/2005 |
| WO | 2005/105779 A1 | 11/2005 |
| WO | 2007/041130 A2 | 4/2007 |
| WO | 2007/084557 A2 | 7/2007 |
| WO | 2009/114512 A1 | 9/2009 |
| WO | 2010/010190 A1 | 1/2010 |
| WO | 2010/070060 A1 | 6/2010 |
| WO | 2010/149769 A1 | 12/2010 |
| WO | 2011/075334 A1 | 6/2011 |
| WO | 2011/076419 A1 | 6/2011 |
| WO | 2011/086053 A1 | 7/2011 |
| WO | 2011/087837 A2 | 7/2011 |
| WO | 2011/101161 A1 | 8/2011 |
| WO | 2012/022045 A1 | 2/2012 |
| WO | 2012/037132 A1 | 3/2012 |

(Continued)

OTHER PUBLICATIONS

D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
E. Derezini et al., 1 Blood Cancer Journal, 1-11 (2011).*
A. Ghigo et al., 32 BioEssays, 185-196 (2010).*
R.J. Kok, 25 Pharmaceutical Research, 2413-2415 (2008).*
Z. Ghiassi-Nejad et al. 2 Expert Review of Gastroenterology & Hepatology, 803-816 (2008).*

(Continued)

*Primary Examiner* — Alexander R Pagano

(57) ABSTRACT

The invention provides a pyrazolothiazole compound of the formula [I], or a pharmaceutically acceptable salt thereof:

The compound of the invention has JAK1 inhibitory activity, and thus, immunosuppressive effect, anti-inflammatory effect and anti-proliferative effect, and is useful in the treatment of the diseases, for example, rheumatoid arthritis, inflammatory bowel disease, psoriasis and vasculitis, bronchial asthma, chronic obstructive pulmonary disease and eosinophilic sinusitis, nasal polyp.

6 Claims, No Drawings

(56) References Cited

FOREIGN PATENT DOCUMENTS

| WO | 2012/054364 A2 | 4/2012 |
|---|---|---|
| WO | 2012/085176 A1 | 6/2012 |
| WO | 2013/025628 A1 | 2/2013 |

OTHER PUBLICATIONS

Z. Wang et al., 19 Drug Discovery Today, 145-150 (2014).*
U.K. Marelli et al., 3 Frontiers in Oncology, 1-12 (2013).*
Kinase Inhibitors Methods and Protocols (B. Kuster ed., 2012).*
R.J. Riese et al., 24 Best Practice & Research Clinical Rheumatology, 513-526 (2010).*
N.K. Williams et al., 387 Journal of Molecular Biology, 219-232 (2009).*
B.H. Kim et al., 7 Molecular Cancer Therapeutics, 2672-2680 (2008).*
S.N. Constantinescu et al., 33 Trends in Biochemical Sciences, 122-131 (2007).*
T. Diaz et al., 6 PLoS One, (2011).*
Jun Abe, "Cytokines in Kawasaki disease," Japanese journal of clinical, National Research Institute for Child Health & Development, Department of Allergy & Immunology, Special Issue: Kawasaki Disease, vol. 72, No. 9, pp. 1548-1553 (2014).
N. Akdeniz et al., "Serum Interleukin-2, Interleukin-6, Tumour Necrosis Factor-Alpha and Nitric Oxide Levels in Patients with Behcet's Disease," Annals Academy of Medicine Singapore, vol. 33, No. 5, pp. 596-599 (Sep. 2004).
Sabina A. Antoniu, "Pitrakinra, a dual IL-4/IL-13 antagonist for the potential treatment of asthma and eczema," Current Opinion in Investigational Drugs, vol. 11 (11), pp. 1286-1294 (2010).
Manabu Araki et al., "Efficacy of the anti-IL-6 receptor antibody tocilizumab in neuromyelitis optica, a pilot study," Neurology, vol. 82, pp. 1302-1306 (Apr. 15, 2014) American Academy of Neurology.
Lei Bao et al., "The involvement of the JAK-STAT signaling pathway in chronic inflammatory skin disease atopic dermatitis," JAK-STAT, 2:3, e24137 (Jul./Aug./Sep. 2013) Landes Bioscience.
Michiel Beekhuizen et al., "Inhibition of Oncostatin M in Osteoarthritic Synovial Fluid Enhances Gag Production in Osteoarthritic Cartilage Repair," European Cells and Materials, vol. 26, pp. 80-90 (2013).
Paula Brown et al., "Single nucleotide polymorphisms (SNPs) in key cytokines may modulate food allergy phenotypes," European Food Research and Technology, vol. 235, Issue 5, pp. 971-980 (Nov. 2012) Springer.
Paul J. Christner and Sergio A. Jimenez, "Animal models of systemic sclerosis: insights into systemic sclerosis pathogenesis and potential therapeutic approaches," Current Opinion in Rheumatology, vol. 16, Issue 6, pp. 746-752 (2004).
Ana P Costa-Pereira et al., "Dysregulation of janus kinases and signal transducers and activators of transcription in cancer," American Journal of Cancer Research, vol. 1(6), pp. 806-816 (2011).
Marinos C. Dalakas, "Biologics and other novel approaches as new therapeutic options in myasthenia gravis: a view to the future," Annals of the New York Academy of Sciences, vol. 1274, pp. 1-8 (2012).
Javier Donate-Correa et al., "Inflammatory Cytokines in Diabetic Nephropathy," Journal of Diabetes Research, vol. 2015, Article ID 948417,9 pages (2015) Hindawi Publishing Corporation.
J. Dong et al., "Activation of the STAT1 signalling pathway in lupus nephritis in MRL/lpr mice," Lupus, vol. 16, pp. 101-109 (2007).
Emily Yiping Gan et al., "Therapeutic strategies in psoriasis patients with psoriatic arthritis: focus on new agents," BioDrugs, vol. 27, pp. 359-373 (2013).
Maria Gliozzi et al., "A link between interferon and augmented plasmin generation in exocrine gland damage in Sjogren's syndrome," Journal of Autoimmunity, vol. 40, pp. 122-133 (2013) Elsevier B.V.
Takahisa Gono et al., "Cytokine profiles in polymyositis and dermatomyositis complicated by rapidly progressive or chronic interstitial lung disease," Rheumatology, vol. 53, pp. 2196-2203 (2014) British Society for Rheumatology (Oxford).
Takashi Goto et al., "Increase in B-cell-activation factor (BAFF) and IFN-gamma productions by tonsillar mononuclear cells stimulated with deoxycytidyl-deoxyguanosine oligodeoxynucleotides (CpG-ODN) in patients with IgA nephropathy," Clinical Immunology, vol. 126, pp. 260-269 (2008).
Bora Gülhan et al., "Studying cytokines of T helper cells in the kidney disease of IgA vasculitis (Henoch-Schönlein purpura)," Pediatric Nephrology, vol. 30, pp. 1269-1277 (2015) Springer.
Claude Haan et al., "Jak1 has a dominant role over Jak3 in signal transduction through γc-containing cytokine receptors," Chemistry & Biology, vol. 18, pp. 314-323 (Mar. 25, 2011) Elsevier Ltd.
Tamihiro Kawakami et al., "Serum Levels of Interleukin-6 in Patients with Cutaneous Polyarteritis Nodosa," Acta Derm Venereol, vol. 92, pp. 322-323 (2012).
P. Kieffer et al., "Efficacité clinique et biologique du tocilizumab au cours de la maladie de Horton : à propos de trois observations et revue de la littérature; Clinical and biological efficacy of tocilizumab in giant cell arteritis: Report of three patients and literature review," La revue de médecine interne, vol. 35, No. 1, pp. 56-59 (2014) Elsevier B.V.
Hirohito Kita et al., "Cytokine production at the site of disease in chronic eosinophilic pneumonitis," American Journal of Respiratory and Critical Care Medicine, vol. 153, No. 4, pp. 1437-1441 (1996).
A. C. Muller Kobold et al., "In vitro up-regulation of E-selectin and induction of interleukin-6 in endothelial cells by autoantibodies in Wegener's granulomatosis and microscopic polyangiitis," Clinical and Experimental Rheumatology, vol. 17, pp. 433-440 (1999).
Taku Kouro and Kiyoshi Takatsu, "IL-5- and eosinophil-mediated inflammation: from discovery to therapy," International Immunology, vol. 21, No. 12, pp. 1303-1309 (2009).
Janusz J. Kulagowski et al., "Identification of Imidazo-Pyrrolopyridines as Novel and Potent JAK1 Inhibitors," Journal of Medicinal Chemistry, vol. 55, pp. 5901-5921 (2012).
Fanny Legrand and Amy D. Klion, "Biologic therapies targeting eosinophils: current status and future prospects," Journal of Allergy and Clinical Immunology: In Practice, vol. 3, Issue 2, pp. 167-174 (2015).
Jun Li et al., "INCB16562, a JAK1/2 Selective Inhibitor, Is Efficacious against Multiple Myeloma Cells and Reverses the Protective Effects of Cytokine and Stromal Cell Support," Neoplasia, vol. 12, No. 1, pp. 28-38 (Jan. 2010) Elsevier B.V.
Sung A. Lim et al., "Association of IL-21 Cytokine With Severity of Primary Sjögren Syndrome Dry Eye," Cornea, vol. 34, No. 3, pp. 248-252 (Mar. 2015).
Jeremiah P. Malerich et al., "Diamino-1,2,4-triazole derivatives are selective inhibitors of TYK2 and JAK1 over JAK2 and JAK3," Bioorganic & Medicinal Chemistry Letters, vol. 20, pp. 7454-7457 (2010) Elsevier B.V.
Masatsugu Masuda et al., "Correlations of inflammatory biomarkers with the onset and prognosis of idiopathic sudden sensorineural hearing loss," Otology & Neurotology, vol. 33, pp. 1142-1150 (2012) Otology & Neurotology, Inc.
Masahiko Mihara et al., "IL-6/IL-6 receptor system and its role in physiological and pathological conditions," Clinical Science, vol. 122, pp. 143-159 (2012) Portland Press.
M. Nabavi et al., "Increased level of interleukin-13, but not interleukin-4 and interferon-γ in chronic rhinosinusitis with nasal polyps," Allergologia et Immunopathologia, vol. 42, Issue 5, pp. 465-471 (2014) Elsevier B.V.
Takashi Nanba et al., "Increases of the Th1/Th2 cell ratio in severe Hashimoto's disease and in the proportion of Th17 cells in intractable Graves' disease," Thyroid, vol. 19, No. 5, pp. 495-501 (2009) Mary Ann Liebert, Inc.
Björn Nashan et al., "Randomised trial of basiliximab versus placebo for control of acute cellular rejection in renal allograft recipients," The Lancet, vol. 350, pp. 1193-1198 (Oct. 25, 1997) Elsevier Limited.

(56) References Cited

OTHER PUBLICATIONS

Markus F. Neurath and Susella Finottob, "IL-6 signaling in autoimmunity, chronic inflammation and inflammation-associated cancer," Cytokine & Growth Factor Reviews, vol. 22, pp. 83-89 (Apr. 2011) Elsevier B.V.

Norihiro Nishimoto et al., "Toxicity, pharmacokinetics, and dose-finding study of repetitive treatment with the humanized anti-interleukin 6 receptor antibody MRA in rheumatoid arthritis. Phase I/II clinical study," The Journal of Rheumatology, vol. 30 (7), pp. 1426-1435 (Jul. 2003).

Norihiro Nishimoto et al., "Improvement in Castleman's disease by humanized anti-interleukin-6 receptor antibody therapy," Blood, vol. 95, No. 1, pp. 56-61 (Jan. 2000) American Society of Hematology.

John J. O'Shea and Robert Plenge, "JAKs and STATs in Immunoregulation and Immune-Mediated Disease," Immunity, vol. 36, Issue 4, pp. 542-550 (Apr. 20, 2012) Elsevier B.V.

Lynda A. O'Sullivan et al., "Cytokine receptor signaling through the Jak-Stat-Socs pathway in disease," Molecular Immunology, vol. 44, pp. 2497-2506 (Apr. 2007) Elsevier B.V.

Alfonso Quintás-Cardama et al., "Janus kinase inhibitors for the treatment of myeloproliferative neoplasias and beyond," Nature Reviews Drug Discovery, vol. 10, pp. 127-140 (Feb. 2011).

D. Saadoun et al., "Th1 and Th17 Cytokines Drive Inflammation in Takayasu Arteritis," Arthritis & Rheumatology, vol. 67, No. 5, pp. 1353-1360 (May 2015) American College of Rheumatology.

Osamu Sakai et al., "Involvement of NFκb in the Production of Chemokines by Rat and Human Conjunctival Cells Cultured Under Allergenic Conditions," Current Eye Research, vol. 38, Issue 8, pp. 825-834 (2013).

E. S. Slavov et al., "Cytokine production in thromboangiitis obliterans patients: New evidence for an immune-mediated inflammatory disorder," Clinical and Experimental Rheumatology, 23, pp. 219-226 (2005).

M. Sokolowska-Wojdylo et al., "Association of distinct IL-31 polymorphisms with pruritus and severity of atopic dermatitis," Journal of the European Academy of Dermatology and Venereology: Letters to the Editor, vol. 27, Issue 5, pp. 662-664 (2013) European Academy of Dermatology and Venereology.

T. Southworth et al., "IFN-γ synergistically enhances LPS signalling in alveolar macrophages from COPD patients and controls by corticosteroid-resistant STAT1 activation," British Journal of Pharmacology, vol. 166, pp. 2070-2083 (2012) The British Pharmacological Society.

B. Strober et al., "Effect of tofacitinib, a Janus kinase inhibitor, on haematological parameters during 12 weeks of psoriasis treatment," British Journal of Dermatology, vol. 169, pp. 992-999 (2013) British Association of Dermatologists.

Yoko Takanami-Ohnishi et al., "Essential Role of p38 Mitogen-activated Protein Kinase in Contact Hypersensitivity," The Journal of Biological Chemistry, vol. 277, No. 40, pp. 37896-37903 (2002) The American Society for Biochemistry and Molecular Biologym, Inc.

Kenchi Takenaka et al., "Successful treatment of refractory aortitis in antineutrophil cytoplasmic antibody-associated vasculitis using tocilizumab," Clinical Rheumatology, vol. 33, Issue 2, pp. 287-289 (2014) Springer International Publishing AG.

A. Vaglio et al., "Eosinophilic granulomatosis with polyangiitis (Churg-Strauss): state of the art," Allergy, vol. 68, Issue 3, pp. 261-273 (2013) John Wiley & Sons Inc.

William Vainchenker et al., "JAKs in pathology: Role of Janus kinases in hematopoietic malignancies and immunodeficiencies," Seminars in Cell & Developmental Biology, vol. 19, Issue 4, pp. 385-393 (Aug. 2008) Elsevier Ltd.

T. Van Zele et al., "Differentiation of chronic sinus diseases by measurement of inflammatory mediators," Allergy, vol. 61, Issue 11, pp. 1280-1289 (2006) John Wiley & Sons, Inc.

Lurine Vuitton et al., "Janus Kinase Inhibition with Tofacitinib: Changing the Face of Inflammatory Bowel Disease Treatment," Current Drug Targets, vol. 14, No. 12, pp. 1385-1391 (2013) Bentham Science Publishers.

Daniel J. Wallace et al., "MEDI-545, an Anti-Interferon Alpha Monoconal Antibody, Shows Evidence of Clinical Activity in Systemic Lupus Erythematosus," ACR Concurrent Session, SLE: Novel Terapies, Nov. 9, 2007, 71st Ann. Meet. Am. Coll. Rheumatol., Abs. 1315.

Shumpei Yokota et al., "Efficacy and safety of tocilizumab in patients with systemic-onset juvenile idiopathic arthritis: a randomised, double-blind, placebo-controlled, withdrawal phase III trial," The Lancet, vol. 371, pp. 998-1006 (Mar. 2008) Elsevier B.V.

Xiaoting Zhang et al., "Lesional infiltration of mast cells, Langerhans cells, T cells and local cytokine profiles in alopecia areata," Archives of Dermatological Research,vol. 307, Issue 4, pp. 319-331 (2015) Springer Nature.

Tomomichi Chonan et al., "Discovery of novel (4-piperidinyl)-piperazines as potent and orally active acetyl-CoA carboxylase ½ non-selective inhibitors: F-Boc and triF-Boc groups are acid-stable bioisosteres for the Boc group," Bioorganic & Medicinal Chemistry, vol. 19, pp. 1580-1593 (2011) Elsevier Ltd.

Wolfgang Kirmse et al., "Desaminierungsreaktionen, 44. Zerfall von 1-Alkylcyclopropandiazonium-Ionen," Chemische Berichte, vol. 119, Issue 12, pp. 3672-3693 (1986).

Dina Manetti et al., "4-Aminopiperidine Derivatives as a New Class of Potent Cognition Enhancing Drugs," Bioorganic & Medicinal Chemistry Letters, vol. 13, Issue 14, pp. 2303-2306 (2003) Elsevier Science Ltd.

Javier Mendiola et al., "Preparation, Use, and Safety of O-Mesitylenesulfonylhydroxylamine," Organic Process Research & Development, vol. 13, No. 2, pp. 263-267 (2009) American Chemical Society.

Melvin S. Newman et al., "Investigation of the gem-Dialkyl Effect in Medicinal Agents," Journal of Medicinal Chemistry, vol. 15, No. 10, pp. 1003-1006 (Oct. 1972) American Chemical Society.

Anette G. Sams et al., "Discovery of N-{1-[3-(3-Oxo-2,3-dihydrobenzo[1,4]oxazin-4-yl)propyl]piperidin-4-yl}-2-phenylacetamide (Lu AE51090): An Allosteric Muscarinic M1 Receptor Agonist with Unprecedented Selectivity and Procognitive Potential," Journal of Medicinal Chemistry, vol. 53, No. 17, pp. 6386-6397 (2010) American Chemical Society.

Sanjita Sasmal et al., "Design and optimization of quinazoline derivatives as melanin concentrating hormone receptor 1 (MCHR1) antagonists," Bioorganic & Medicinal Chemistry Letters, vol. 22, Issue 9, pp. 3157-3162 (2012) Elsevier Ltd.

\* cited by examiner

PYRAZOLOTHIAZOLE COMPOUND AND MEDICINE COMPRISING SAME

CROSS REFERENCE TO RELATED APPLICATIONS

This patent application is a U.S. national stage application under 35 U.S.C. § 371 of International Patent Application No. PCT/JP2015/074935 filed on Sep. 2, 2015, which claims the benefit of foreign priority to Japanese Patent Application No. JP 2014-177969 filed on Sep. 2, 2014. The International Application was published in Japanese on Mar. 10, 2016, as International Publication No. WO 2016/035814 A1 under PCT Article 21(2).

FIELD OF THE INVENTION

The present invention relates to a pharmaceutical composition comprising a novel pyrazolothiazole compound, or a pharmaceutically acceptable salt thereof, or a solvate thereof as an active ingredient.

BACKGROUND ART

Tyrosine kinases are a group of enzymes that specifically phosphorylate a tyrosine residue in proteins. The enzymes have a significant role in the intracellular signal transduction pathways and relate to a wide variety of biological functions including cell survival, differentiation, proliferation, and secretion. Janus Kinase (also referred to as JAK) family is known as that of intracellular tyrosine kinases involving a cytokine signaling. JAK family includes the four types of enzymes: JAK1, JAK2, JAK3 and Tyrosine Kinase 2 (also referred to as Tyk2). Once a cytokine associates with its respective cytokine receptor, JAK is phosphorylated, and a tyrosine residue of the receptor is then phosphorylated. Then, signal transducer and activator of transcription (also referred to as "STAT"), which exists in cells, will become associated with the phosphorylated tyrosine residue of the receptor, and a tyrosine residue of STAT is phosphorylated by JAK. The phosphorylated STATs form a dimer, and the dimer translocates into the nucleus and activates transcription of target gene, which leads to activation of the cells. JAK/STAT pathways are the key intracellular signal transduction pathways of cytokines in immunocompetent cells (Non-Patent Literature 1). About 40 types of cytokine signal transductions are mediated by a combination of the four JAKs and seven STATs, and abnormalities of a cytokine production and a cytokine signaling are believed to have an intimate involvement in not only various immune and inflammatory diseases, such as autoimmune diseases and allergic diseases, but also diseases having diverse pathologies such as cancers. Compounds suppressing the activation of these JAK/STAT pathways draw attention as new therapeutics for these diseases, and, in fact, JAK inhibitors have already been approved in the United States and Japan as a therapeutic for myelofibrosis, polycythemia vera and rheumatoid arthritis. Further, effects of such compounds are expected in the treatment of other autoimmune diseases (such as psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (such as Takayasu's arteritis, giant cell arteritis, microscopic polyangiitis, granulomatosis with polyangiitis and eosinophilic granulomatosis with polyangiitis), dermatomyositis, polymyositis and neuromyelitis optica), inflammatory diseases (such as atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (such as solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection. Currently, the clinical trials are in progress for some diseases as listed above in Japan, the United States and Europe.

Specifically, various biological studies have demonstrated an important role of JAK1 in the signal transductions of many cytokines (See Non-Patent Literatures 2, 3 and 4), indicating that JAK1 inhibitors are useful in the treatment of the diseases, such as autoimmune diseases: psoriatic arthritis (See Non-Patent Literature 5), juvenile arthritis (See Non-Patent Literature 6), Castleman's disease (See Non-Patent Literature 6), systemic lupus erythematosus (See Non-Patent Literature 7), Sjögren's syndrome (See Non-Patent Literature 8), multiple sclerosis (See Non-Patent Literature 9), inflammatory bowel disease (See Non-Patent Literature 10), Behçet's disease (See Non-Patent Literature 11), myasthenia gravis (See Non-Patent Literature 12), type 1 diabetes mellitus (See Non-Patent Literature 9), immunoglobulin nephropathy (See Non-Patent Literature 13), autoimmune thyroid diseases (See Non-Patent Literature 14), psoriasis (See Non-Patent Literature 15), scleroderma (See Non-Patent Literature 16), lupus nephritis (See Non-Patent Literature 17), dry eye (See Non-Patent Literature 18), vasculitis (See Non-Patent Literatures 19, 20, 21, 22 and 23), dermatomyositis (See Non-Patent Literature 24), polymyositis (See Non-Patent Literature 24), neuromyelitis optica (See Non-Patent Literature 25); inflammatory diseases: atopic dermatitis (See Non-Patent Literature 26), contact dermatitis (See Non-Patent Literature 27), eczema (See Non-Patent Literature 28), pruritus (See Non-Patent Literature 29), food allergies (See Non-Patent Literature 30), bronchial asthma (See Non-Patent Literature 31), eosinophilic pneumonia (See Non-Patent Literature 32), chronic obstructive pulmonary disease (See Non-Patent Literature 33), allergic rhinitis (See Non-Patent Literature 31), chronic sinusitis (See Non-Patent Literature 34), eosinophilic sinusitis, nasal polyp (See Non-Patent Literature 35), allergic conjunctivitis (See Non-Patent Literature 36), osteoarthritis (See Non-Patent Literature 37), ankylosing spondylitis (See Non-Patent Literature 6), Kawasaki disease (See Non-Patent Literature 38), Buerger's disease (See Non-Patent Literature 39), polyarteritis nodosa (See Non-Patent Literature 40), IgA vasculitis (See Non-Patent Literature 41); proliferative diseases: solid cancers, blood cancers, lymph malignant tumor, myeloproliferative diseases, multiple myeloma (See Non-Patent Literatures 42, 43 and 44), sudden hearing loss (See Non-Patent Literature 45), diabetic nephropathy (See Non-Patent Literature 46), alopecia areata (See Non-Patent Literature 47), bone marrow transplant rejection or organ transplant rejection, etc. For example, the following clinical trials are in progress. Rheumatoid arthritis (https://clinicaltrials.gov/NCT01888874 and NCT02049138), Crohn's disease (https://clinicaltrials.gov/NCT02365649), non small cell lung cancer (https://clinicaltrials.gov/NCT02257619), pancreatic cancer (https://clinicaltrials.gov/NCT01858883), myelofibrosis (https://clinicaltrials.gov/NCT01633372) and psoriasis (https://clinicaltrials.gov/NCT02201524).

Further, among the cytokine signalings associated with JAK1, the inhibitors for the following cytokines have already been launched.

(1) IL-6 (also referred to as interleukin-6): therapeutic agents for rheumatoid arthritis, juvenile arthritis and Castleman's disease (See Non-Patent Literatures 48, 49 and 50).
(2) IL-2: therapeutic agent for acute rejection following renal transplantation (See Non-Patent Literature 51).

In addition, the clinical trials on the following cytokine inhibitors are in progress.

(3) IL-4 and IL-13: therapeutic agent for bronchial asthma, atopic dermatitis, eosinophilic sinusitis, nasal polyp and eosinophilic esophagitis (See Non-Patent Literature 31).
(4) IL-13: therapeutic agent for pulmonary fibrosis (See https://clinicaltrials.gov/NCT02036580).
(5) IL-5: therapeutic agent for bronchial asthma, chronic obstructive pulmonary disease, eosinophilia, eosinophilic granulomatosis with polyangiitis, eosinophilic esophagitis, eosinophilic sinusitis/nasal polyp and atopic dermatitis (See Non-Patent Literature 31 and Non-Patent Literature 52).
(6) IFNα (also referred to as interferon-α): therapeutic agent for systemic lupus erythematosus (See Non-Patent Literature 7).
(7) IL-31: therapeutic agent for atopic dermatitis (https://clinicaltrials.gov/NCT01986933).
(8) TSLP (also referred to as thymic stromal lymphopoietin): therapeutic agents for bronchial asthma (https://clinicaltrials.gov/NCT02054130) and atopic dermatitis (https://clinicaltrials.gov/NCT00757042).

Thus, the inhibition of JAK1 signal is a preferred means for the prevention or treatment of the diseases caused by an abnormality of JAK1, such as autoimmune diseases, inflammatory diseases and proliferative diseases.

As a JAK1 inhibitor, [1,2,4]triazolo[1,5-a]pyridines (See Patent Literatures 1 and 2), tricyclic pyrazinones (See Patent Literature 3), pyrrolopyrimidines (See Patent Literatures 4 to 7), phthalazines (See Patent Literature 8), imidazopyrrolopyridines (See Patent Literature 9 and Non-Patent Literature 53), diamino-1,2,4-triazoles (See Non-Patent Literature 54), pyrazolo[1,5-a]pyridines (See Patent Literature 10), imidazo[1,2-a]pyridines (See Patent Literatures 11 and 12), benzimidazoles (See Patent Literature 13), 7-azaindoles (See Patent Literature 14) are reported. However, none of the documents as mentioned disclose pyrazolo[5,1-b][1,3]thiazole compounds.

PRIOR ART DOCUMENTS

Non-Patent Literatures

[Non-Patent Literature 1] O'Shea et al., Immunity, 2012, 36, 542-550.
[Non-Patent Literature 2] O'Sullivan et al., Mol. Immunol., 2007, 44, 2497-2506.
[Non-Patent Literature 3] Quintás-Cardama et al., Nat. Rev. Drug Discov., 2011, 10, 127-140.
[Non-Patent Literature 4] Haan et al., Chem. Biol., 2011, 18, 314-323.
[Non-Patent Literature 5] Gan et al., BioDrugs, 2013, 27, 359-373.
[Non-Patent Literature 6] Mihara et al., Clin. Sci. (Lond.), 2012, 122, 143-159.
[Non-Patent Literature 7] Wallace et al., 71st Ann. Meet. Am. Coll. Rheumatol., 2007, Abs. 1315.
[Non-Patent Literature 8] Gliozzi et al., J. Autoimmun., 2013, 40, 122-133.
[Non-Patent Literature 9] Neurath et al., Cytokine Growth Factor Rev., 2011, 22, 83-89.
[Non-Patent Literature 10] Vuitton et al., Curr. Drug Targets, 2013, 14, 1385-1391.
[Non-Patent Literature 11] Akdeniz et al., Ann. Acad. Med. Singapore, 2004, 33, 596-599.
[Non-Patent Literature 12] Dalakas, Ann. N.Y. Acad. Sci., 2012, 1274, 1-8.
[Non-Patent Literature 13] Goto et al., Clin. Immunol., 2008, 126, 260-269.
[Non-Patent Literature 14] Nanba et al., Thyroid, 2009, 19, 495-501.
[Non-Patent Literature 15] Strober et al., Br. J. Dermatol., 2013, 169, 992-999.
[Non-Patent Literature 16] Christner et al., Curr. Opin. Rheumatol., 2004, 16, 746-752.
[Non-Patent Literature 17] Dong et al., Lupus, 2007, 16, 101-109.
[Non-Patent Literature 18] Lim et al., Cornea, 2015, 34, 248-252.
[Non-Patent Literature 19] Saadoun et al., Arthritis Rheumatol., 2015, 67, 1353-1360.
[Non-Patent Literature 20] Kieffer et al., Rev. Med. Interne., 2014, 35, 56-59.
[Non-Patent Literature 21] Takenaka et al., Clin. Rheumatol., 2014, 33, 287-289.
[Non-Patent Literature 22] Kobold et al., Clin. Exp. Rheumatol., 1999, 17, 433-440.
[Non-Patent Literature 23] Vaglio et al., Allergy, 2013, 68, 261-273.
[Non-Patent Literature 24] Gono et al., Rheumatology, 2014, 53, 2196-2203.
[Non-Patent Literature 25] Araki et al., Neurology, 2014, 82, 1302-1306.
[Non-Patent Literature 26] Bao et al., JAKSTAT, 2013, 2, e24137.
[Non-Patent Literature 27] Takanami-Ohnishi et al., J. Biol. Chem., 2002, 277, 37896-37903.
[Non-Patent Literature 28] Antoniu, Curr. Opin. Investig. Drugs, 2010, 11, 1286-1294.
[Non-Patent Literature 29] Sokoowska-Wojdyo et al., J. Eur. Acad. Dermatol. Venereol., 2013, 27, 662-664.
[Non-Patent Literature 30] Brown et al., Eur. Food Res. Technol., 2012, 235, 971-980.
[Non-Patent Literature 31] Legrand et al., J. Allergy Clin. Immunol. Pract., 2015, 3, 167-174.
[Non-Patent Literature 32] Kita et al., Am. J. Respir. Crit. Care Med., 1996, 153, 1437-1441.
[Non-Patent Literature 33] Southworth et al., Br. J. Pharmacol., 2012, 166, 2070-2083.
[Non-Patent Literature 34] Van Zele et al., Allergy, 2006, 61, 1280-1289.
[Non-Patent Literature 35] Nabavi et al., Allergol. Immunopathol. (Madr.), 2014, 42, 465-471.
[Non-Patent Literature 36] Sakai et al., Curr. Eye Res., 2013, 38, 825-834.
[Non-Patent Literature 37] Beekhuizen et al., Eur. Cell Mater., 2013, 26, 80-90.
[Non-Patent Literature 38] Abe, Nihon Rinsho, 2014, 72, 1548-1553.
[Non-Patent Literature 39] Slavov et al., Clin. Exp. Rheumatol., 2005, 23, 219-226.

[Non-Patent Literature 40] Kawakami et al., Acta. Derm. Venereol. 2012, 92, 322-323.
[Non-Patent Literature 41] Gülhan et al., Pediatr. Nephrol., 2015, 30, 1269-1277.
[Non-Patent Literature 42] Costa-Pereira et al., Am. J. Cancer Res., 2011, 1, 806-816.
[Non-Patent Literature 43] Vainchenker et al., Semin. Cell Dev. Biol., 2008, 19, 385-393.
[Non-Patent Literature 44] Li et al., Neoplasia, 2010, 12, 28-38.
[Non-Patent Literature 45] Masuda et al., Otol. Neurotol., 2012, 33, 1142-1150.
[Non-Patent Literature 46] Donate-Correa et al., J. Diabetes Res., 2015, 948417.
[Non-Patent Literature 47] Zhang et al., Arch. Dermatol. Res., 2015, 307, 319-331.
[Non-Patent Literature 48] Nishimoto et al., J. Rheumatol., 2003, 30, 1426-1435.
[Non-Patent Literature 49] Yokota et al., LANCET, 2008, 371, 998-1006.
[Non-Patent Literature 50] Nishimoto et al., Blood, 2000, 95, 56-61.
[Non-Patent Literature 51] Nashan et al., LANCET, 1997, 350, 1193-1198.
[Non-Patent Literature 52] Kouro et al., Int. Immunol., 2009, 21, 1303-1309.
[Non-Patent Literature 53] Kulagowski et al., Journal of Medicinal Chemistry, 2012, 55, 5901-5921.
[Non-Patent Literature 54] Malerich et al., Bioorg. Med. Chem. Lett., 2010, 20, 7454-7457.

Patent Literature

[Patent Literature 1] WO 2010/149769
[Patent Literature 2] WO 2010/010190
[Patent Literature 3] WO 2012/085176
[Patent Literature 4] WO 2009/114512
[Patent Literature 5] WO 2011/075334
[Patent Literature 6] WO 2012/022045
[Patent Literature 7] WO 2012/054364
[Patent Literature 8] WO 2012/037132
[Patent Literature 9] WO 2011/086053
[Patent Literature 10] WO 2011/101161
[Patent Literature 11] WO 2011/076419
[Patent Literature 12] JP 2011/136925
[Patent Literature 13] WO 2005/066156
[Patent Literature 14] WO 2007/084557

SUMMARY OF THE INVENTION

Problem to be Solved by the Invention

An object of the present invention is to provide a compound with an excellent JAK1 inhibitory activity.

Means for Solving the Problem

The present invention is based on the inventors' discovery that a compound represented by the following general formula [I] or a pharmaceutically acceptable salt thereof, or a solvate thereof (herein after referred to as "the compound of the invention") has an excellent JAK1 inhibitory activity.
Thus, the present inventions as in the following (I) to (XVII) are disclosed.

(I) A pyrazolothiazole compound represented by the formula [I]:

[Formula 1]

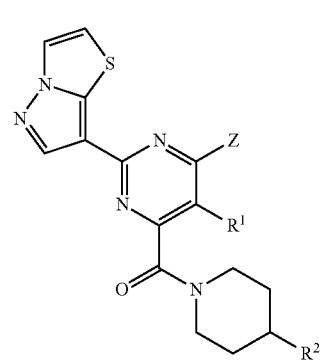

[I]

wherein,
$R^1$ is hydrogen, alkyl or alkoxy;
Z is —$OR^3$ or —$NR^4R^5$;
in which
$R^3$ is alkyl, alkyl substituted with cycloalkyl, cycloalkyl, aryl or heteroaryl;
$R^4$ is hydrogen or alkyl;
$R^5$ is alkyl, cycloalkyl or saturated heterocyclic group, said alkyl and cycloalkyl in $R^5$ is optionally substituted with one or two groups selected from the group consisting of the following (1) to (6):
(1) hydroxy,
(2) alkoxy, and difluoroalkoxy,
(3) cycloalkyl, cycloalkyl substituted with (difluoroalkoxy)alkyl, and cycloalkyl substituted with alkoxyalkyl,
(4) saturated heterocyclic group optionally substituted with (difluoroalkoxy)alkyl,
(5) aryl, aryl substituted with halogen, and aryl substituted with alkoxy, and
(6) nitrile, and
said saturated heterocyclic group in $R^5$ is optionally substituted with one or two groups selected from the group consisting of the following (1) to (3):
(1) alkyl,
(2) alkylcarbonyl, and
(3) alkoxycarbonyl;
$R^2$ is hydroxy or —$NHR^8$,
in which
$R^8$ is heteroaryl, heteroaryl substituted with halogen, heteroaryl substituted with alkyl, —$COL^1$, —$COOL^2$ or —$SO_2L^3$, said $L^1$ is a group selected from the group consisting of the following (1) to (5):
(1) alkyl, monohaloalkyl, dihaloalkyl, trihaloalkyl, and alkyl substituted with alkoxy,
(2) cycloalkyl,
(3) aryl,
(4) heteroaryl, and
(5) dialkylamino, and cycloalkylamino,
said $L^2$ is a group selected from the group consisting of the following (1) to (3):
(1) alkyl, monohaloalkyl, dihaloalkyl, trihaloalkyl, and alkyl substituted with alkoxy,
(2) cycloalkyl, and
(3) dialkylaminoalkyl, and
said $L^3$ is alkyl or cycloalkyl,
or a pharmaceutically acceptable salt thereof, or a solvate thereof.

(II) The pyrazolothiazole compound as described in (I) or a pharmaceutically acceptable salt thereof, or a solvate thereof, wherein $R^1$ is hydrogen.

(III) The pyrazolothiazole compound as described in (II) or a pharmaceutically acceptable salt thereof, or a solvate thereof, wherein Z is —$NR^4R^5$;

in which $R^4$ is hydrogen, $R^5$ is alkyl or cycloalkyl, said alkyl and cycloalkyl in $R^5$ are optionally substituted with a group selected from the group consisting of the following (1) to (3):
  (1) hydroxy,
  (2) alkoxy, and
  (3) cycloalkyl, $R^2$ is hydroxy or —$NHR^8$, $R^8$ is heteroaryl, heteroaryl substituted with halogen, heteroaryl substituted with alkyl, —$COL^1$ or —$COOL^2$, said $L^1$ is a group selected from the group consisting of the following (1) to (4):
  (1) alkyl, monohaloalkyl, dihaloalkyl, trihaloalkyl, and alkyl substituted with alkoxy,
  (2) cycloalkyl,
  (3) aryl, and
  (4) heteroaryl, and said $L^2$ is alkyl, monohaloalkyl, dihaloalkyl, trihaloalkyl, alkyl substituted with alkoxy or cycloalkyl.

(IV) The pyrazolothiazole compound as described in (III) or a pharmaceutically acceptable salt thereof, or a solvate thereof, wherein $R^5$ is alkyl, alkyl substituted with hydroxy, alkyl substituted with cyclopropyl or alkyl substituted with alkoxy, and $R^2$ is —NHR.

(V) The pyrazolothiazole compound as described in (III) or a pharmaceutically acceptable salt thereof, or a solvate thereof, wherein $R^5$ is alkyl having 2 to 6 carbon atoms or alkyl substituted with cyclopropyl, $R^2$ is —$NHR^8$, $R^8$ is —$COL^1$ or —$COOL^2$, said $L^1$ is alkyl having 2 to 6 carbon atoms or cyclopropyl, and said $L^2$ is alkyl or cyclopropyl.

(VI) The pyrazolothiazole compound as described in (I) which is any one of the following (1) to (135):

(1) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide, (2) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)acetamide, (3) N-(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide, (4) N-(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)acetamide, (5) N-(1-{[6-{[(1S,2S)-2-(difluoromethoxy)cyclopentyl](methyl)amino}-2-(pyrazolo[5,1-b][1,3]thiazol-7-yl)pyrimidin-4-yl]carbonyl}piperidin-4-yl)cyclopropanecarboxamide, (6) N-(1-{[6-{[(2S)-3,3-dimethylbutan-2-yl]amino}-5-methyl-2-(pyrazolo[5,1-b][1,3]thiazol-7-yl)pyrimidin-4-yl]carbonyl}piperidin-4-yl)acetamide, (7) N-(1-{[6-({[(2S)-3,3-dimethylbutan-2-yl]amino}-5-methyl-2-(pyrazolo[5,1-b][1,3]thiazol-7-yl)pyrimidin-4-yl]carbonyl}piperidin-4-yl)cyclopropanecarboxamide, (8) N-[1-({6-[({1-[(difluoromethoxy)methyl]cyclopropyl}methyl)amino]-2-(pyrazolo[5,1-b][1,3]thiazol-7-yl)pyrimidin-4-yl}carbonyl)piperidin-4-yl]cyclopropanecarboxamide, (9) N-[1-({6-[({1-[(difluoromethoxy)methyl]cyclobutyl}methyl)amino]-2-(pyrazolo[5,1-b][1,3]thiazol-7-yl)pyrimidin-4-yl}carbonyl)piperidin-4-yl]cyclopropanecarboxamide,

(10) N-[1-({6-[({1-[(difluoromethoxy)methyl]cyclopentyl}methyl)amino]-2-(pyrazolo[5,1-b][1,3]thiazol-7-yl)pyrimidin-4-yl}carbonyl)piperidin-4-yl]cyclopropanecarboxamide,

(11) N-[1-({6-[({4-[(difluoromethoxy)methyl]tetrahydro-2H-pyran-4-yl}methyl)amino]-2-(pyrazolo[5,1-b][1,3]thiazol-7-yl)pyrimidin-4-yl)carbonyl}piperidin-4-yl]cyclopropanecarboxamide,

(12) N-(1-{[6-{[(1S)-1-cyclopropylethyl]amino}-5-methyl-2-(pyrazolo[5,1-b][1,3]thiazol-7-yl)pyrimidin-4-yl]carbonyl}piperidin-4-yl)cyclopropanecarboxamide,

(13) N-(1-{[6-{[(1S)-1-cyclopropylethyl]amino}-5-methyl-2-(pyrazolo[5,1-b][1,3]thiazol-7-yl)pyrimidin-4-yl]carbonyl}piperidin-4-yl)acetamide,

(14) N-(1-{[6-{[(1S,2S)-2-(difluoromethoxy)cyclopentyl]amino}-2-(pyrazolo[5,1-b][1,3]thiazol-7-yl)pyrimidin-4-yl]carbonyl}piperidin-4-yl)cyclopropanecarboxamide,

(15) N-[1-({6-[(2,2-dimethylpropyl)amino]-2-(pyrazolo[5,1-b][1,3]thiazol-7-yl)pyrimidin-4-yl}carbonyl)piperidin-4-yl]cyclopropanecarboxamide,

(16) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,

(17) N-(1-{([6-{[(2S)-1-(difluoromethoxy)propan-2-yl]amino}-2-(pyrazolo[5,1-b][1,3]thiazol-7-yl)pyrimidin-4-yl]carbonyl}piperidin-4-yl)cyclopropanecarboxamide,

(18) N-(1-{([6-{[(1S)-1-cyclopropylethyl]amino}-5-methyl-2-(pyrazolo[5,1-b][1,3]thiazol-7-yl)pyrimidin-4-yl]carbonyl}piperidin-4-yl)-2,2-difluoroacetamide,

(19) N-(1-{([6-{[(1S,2S)-2-methoxycyclopentyl]amino}-2-(pyrazolo[5,1-b][1,3]thiazol-7-yl)pyrimidin-4-yl]carbonyl}piperidin-4-yl)cyclopropanecarboxamide,

(20) [6-{[(1S)-1-cyclopropylethyl]amino}-2-(pyrazolo[5,1-b][1,3]thiazol-7-yl)pyrimidin-4-yl](4-hydroxypiperidin-1-yl)methanone,

(21) 1-fluoro-2-methylpropan-2-yl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,

(22) methyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate,

(23) [6-{[(2S)-3,3-dimethylbutan-2-yl]amino}-2-(pyrazolo[5,1-b][1,3]thiazol-7-yl)pyrimidin-4-yl](4-hydroxypiperidin-1-yl)methanone,

(24) methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate,

(25) methyl(1-{[6-{[(2S)-3-methylbutan-2-yl]amino}-2-(pyrazolo[5,1-b][1,3]thiazol-7-yl)pyrimidin-4-yl]carbonyl}piperidin-4-yl)carbamate,

(26) methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,

(27) ethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,

(28) propan-2-yl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(29) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)benzamide,
(30) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)pyridine-3-carboxamide,
(31) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)thiophene-2-carboxamide,
(32) N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide,
(33) 1-cyclopropyl-3-(1-{[(6-{[(1S)-1-cyclopropylethyl]amino}-2-(pyrazolo[5,1-b][1,3]thiazol-7-yl)pyrimidin-4-yl]carbonyl}piperidin-4-yl)urea,
(34) [6-{[(1S)-1-cyclopropylethyl](methyl)amino}-2-(pyrazolo[5,1-b][1,3]thiazol-7-yl)pyrimidin-4-yl][4-(pyrimidin-2-ylamino)piperidin-1-yl]methanone,
(35) N-(1-{[6-(tert-butylamino)-2-(pyrazolo[5,1-b][1,3]thiazol-7-yl)pyrimidin-4-yl]carbonyl}piperidin-4-yl)cyclopropanecarboxamide,
(36) N-[1-({6-[(1-methylcyclopropyl)amino]-2-(pyrazolo[5,1-b][1,3]thiazol-7-yl)pyrimidin-4-yl}carbonyl)piperidin-4-yl]cyclopropanecarboxamide,
(37) N-[1-({6-[(1-methoxy-2-methylpropan-2-yl)amino]-2-(pyrazolo[5,1-b][1,3]thiazol-7-yl)pyrimidin-4-yl}carbonyl)piperidin-4-yl]cyclopropanecarboxamide,
(38) methyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(39) ethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(40) propan-2-yl(1-{[6-{[(1S)-1-cyclopropylethyl]amino}-2-(pyrazolo[5,1-b][1,6]thiazol-7-yl)pyrimidin-4-yl]carbonyl}piperidin-4-yl)carbamate,
(41) N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)benzamide,
(42) N-(1-{[6-(cyclopropylmethoxy)-2-(pyrazolo[5,1-b][1,3]thiazol-7-yl)pyrimidin-4-yl]carbonyl}piperidin-4-yl)cyclopropanecarboxamide,
(43) N-[1-({6-[(3,3-dimethylbutan-2-yl)oxy]-2-(pyrazolo[5,1-b][1,3]thiazol-7-yl)pyrimidin-4-yl}carbonyl)piperidin-4-yl]cyclopropanecarboxamide,
(44) N-(1-{[6-(cyclobutyloxy)-2-(pyrazolo[5,1-b][1,3]thiazol-7-yl)pyrimidin-4-yl]carbonyl}piperidin-4-yl)cyclopropanecarboxamide,
(45) N-(1-{[6-(cyclopentyloxy)-2-(pyrazolo[5,1-b][1,3]thiazol-7-yl)pyrimidin-4-yl]carbonyl}piperidin-4-yl)cyclopropanecarboxamide,
(46) N-(1-{[6-{[(1R)-1-cyclopropylethyl]amino}-2-(pyrazolo[5,1-b][1,3]thiazol-7-yl)pyrimidin-4-yl]carbonyl}piperidin-4-yl)cyclopropanecarboxamide,
(47) N-(1-({6-[(1-hydroxy-2-methylpropan-2-yl)amino)-2-(pyrazolo[5,1-b][1,3]thiazol-7-yl)pyrimidin-4-yl)carbonyl}piperidin-4-yl)cyclopropanecarboxamide,
(48) [6-([(1S)-1-cyclopropylethyl]amino)-2-(pyrazolo[5,1-b][1,3]thiazol-7-yl)pyrimidin-4-yl][4-(1,2-oxazol-3-ylamino)piperidin-1-yl]methanone,
(49) [6-{[(1S)-1-cyclopropylethyl]amino}-2-(pyrazolo[5,1-b][1,3]thiazol-7-yl)pyrimidin-4-yl][4-(1,3-thiazol-2-ylamino)piperidin-1-yl]methanone,
(50) [6-{[(1S)-1-cyclopropylethyl]amino}-2-(pyrazolo[5,1-b][1,3]thiazol-7-yl)pyrimidin-4-yl]{4-[(3-methyl-1,2-oxazol-5-yl)amino]piperidin-1-yl}methanone,
(51) N-(1-{[6-{[(2S)-1-hydroxy-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxanide,
(52) [6-(tert-butylamino)-2-(pyrazolo[5,1-b][1,3]thiazol-7-yl)pyrimidin-4-yl](4-hydroxypiperidin-1-yl)methanone,
(53) methyl(1-{[6-(tert-butylamino)-2-(pyrazolo[(5,1-b][1,3]thiazol-7-yl)pyrimidin-4-yl]carbonyl}piperidin-4-yl)carbamate,
(54) propan-2-yl(1-{[6-(tert-butylamino)-2-(pyrazolo[5,1-b][1,3]thiazol-7-yl)pyrimidin-4-yl]carbonyl}piperidin-4-yl)carbamate,
(55) methyl[1-({6-[(1-hydroxy-2-methylpropan-2-yl)amino]-2-(pyrazolo[5,1-b][1,3]thiazol-7-yl)pyrimidin-4-yl}carbonyl)piperidin-4-yl]carbamate,
(56) [6-{[(2R)-3,3-dimethylbutan-2-yl]amino}-2-(pyrazolo[5,1-b][1,3]thiazol-7-yl)pyrimidin-4-yl](4-hydroxypiperidin-1-yl)methanone,
(57) methyl(1-{[6-{[(2S)-1-hydroxy-3,3-dimethylbutan-2-yl]amino}-2-(pyrazolo[5,1-b][1,3]thiazol-7-yl)pyrimidin-4-yl]carbonyl}piperidin-4-yl)carbamate,
(58) methyl[1-({6-[(3,3-dimethylbutan-2-yl)oxy]-2-(pyrazolo[5,1-b][1,3]thiazol-7-yl)pyrimidin-4-yl}carbonyl)piperidin-4-yl]carbamate,
(59) methyl(1-{[6-(cyclobutyloxy)-2-(pyrazolo[5,1-b][1,3]thiazol-7-yl)pyrimidin-4-yl]carbonyl}piperidin-4-yl)carbamate,
(60) N-(1-{[6-{[(1S)-1-cyclopropylethyl]amino}-2-]carbonyl}piperidin-4-yl)methanesulfonamide,
(61) N-(1-{[6-[{(1S)-1-cyclopropylethyl]amino}-2-(pyrazolo[5,1-b][1,3]thiazol-7-yl)pyrimidin-4-yl]carbonyl}piperidin-4-yl)cyclopropanesulfonamide,
(62) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl) ethanesulfonamide,
(63) N-(1-{[6-(tert-butylamino)-2-(pyrazolo[5,1-b][1,3]thiazol-7-yl)pyrimidin-4-yl]carbonyl}piperidin-4-yl)-2-methylpropanamide,
(64) N-(1-{[6-(tert-butylamino)-2-(pyrazolo[5,1-b][1,3]thiazol-7-yl)pyrimidin-4-yl]carbonyl}piperidin-4-yl)-2,2-difluoroacetamide,
(65) ethyl(1-{[6-(tert-butylamino)-2-(pyrazolo[5,1-b][1,3]thiazol-7-yl)pyrimidin-4-yl]carbonyl}piperidin-4-yl)carbamate,
(66) [6-(tert-butylamino)-2-(pyrazolo[5,1-b][1,3]thiazol-7-yl)pyrimidin-4-yl][4-(pyridin-2-ylamino)piperidin-1-yl]methanone,
(67) ethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate,
(68) [6-(tert-butylamino)-2-(pyrazolo[5,1-b][1,3]thiazol-7-yl)pyrimidin-4-yl][4-(1,3-thiazol-2-ylamino)piperidin-1-yl]methanone,
(69) [6-(tert-butylamino)-2-(pyrazolo[5,1-b][1,3]thiazol-7-yl)pyrimidin-4-yl][4-(pyrimidin-2-ylamino)piperidin-1-yl]methanone,
(70) methyl(1-([6-[(2-methylbutan-2-yl)amino]-2-(pyrazolo[5,1-b][1,3]thiazol-7-yl)pyrimidin-4-yl)carbonyl)piperidin-4-yl]carbamate,
(71) (4-hydroxypiperidin-1-yl)[6-(pentan-3-ylamino)-2-(pyrazolo[5,1-b][1,3]thiazol-7-yl)pyrimidin-4-yl]ethylone,
(72) propyl(1-{[6-(tert-butylamino)-2-(pyrazolo[5,1-b][1,3]thiazol-7-yl)pyrimidin-4-yl]carbonyl}piperidin-4-yl)carbamate,

(73) propyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate,
(74) propyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(75) propyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(76) propyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate,
(77) methyl[1-({6-[(2,2-dimethylpropyl)amino]-2-(pyrazolo[5,1-b][1,3]thiazol-7-yl)pyrimidin-4-yl}carbonyl)piperidin-4-yl]carbamate,
(78) 2-methoxyethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate,
(79) 2-methoxyethyl(1-{[6-{[((1S)-1-cyclopropylethyl]amino}-2-(pyrazolo[5,1-b][1,3]thiazol-7-yl)pyrimidin-4-yl]carbonyl}piperidin-4-yl)carbamate,
(80) 2-methoxyethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(81) 2-methoxyethyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate,
(82) N-(1-{[6-[{(1R)-1-cyclopropylethyl]amino}-2-(pyrazolo[5,1-b][1,3]thiazol-7-yl)pyrimidin-4-yl]carbonyl}piperidin-4-yl)-2-methoxyacetamide,
(83) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)-2-methoxyacetamide,
(84) methyl[1-({6-[({[1-(methoxymethyl)cyclopropyl]methyl}(methyl)amino]-2-(pyrazolo[5,1-b][1,3]thiazol-7-yl)pyrimidin-4-yl}carbonyl)piperidin-4-yl]carbamate,
(85) 2,2-difluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate,
(86) 2,2-difluoroethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(87) 2,2-difluoroethyl(1-{[6-{[(1S)-1-cyclopropylethyl]amino}-2 (pyrazolo[5,1-b][1,3]thiazol-7-yl)pyrimidin-4-yl]carbonyl}piperidin-4-yl)carbamate,
(88) 2,2-difluoroethyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate,
(89) tert-butyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl) carbamate,
(90) 2-methoxyethyl(1-{[6-(tert-butylamino)-2-(pyrazolo[5,1-b][1,3]thiazol-7-yl)pyrimidin-4-yl]carbonyl}piperidin-4-yl)carbamate,
(91) 2-(dimethylamino)ethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(92) 2,2,2-trifluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl) carbamate,
(93) 2,2,2-trifluoroethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(94) 2-methoxy-N-(1-{[6-(pentan-3-ylamino)-2-(pyrazolo[5,1-b][1,3]thiazol-7-yl)pyrimidin-4-yl]carbonyl}piperidin-4-yl)acetamide,
(95) N-(1-{[6-(2-ethylbutoxy)-2-(pyrazolo[5,1-b][1,3]thiazol-7-yl)pyrimidin-4-yl]carbonyl}piperidin-4-yl)cyclopropanecarboxamide,
(96) methyl(1-{[6-(pentan-3-yloxy)-2-(pyrazolo[5,1-b][1,3]thiazol-7-yl)pyrimidin-4-yl]carbonyl}piperidin-4-yl)carbamate,
(97) methyl(1-{[6-(pentan-3-ylamino)-2-(pyrazolo[5,1-b][1,3]thiazol-7-yl)pyrimidin-4-yl]carbonyl}piperidin-4-yl)carbamate,
(98) N-[1-({6-[(2-ethylbutyl)amino]-2-(pyrazolo[5,1-b][1,3]thiazol-7-yl)pyrimidin-4-yl}carbonyl)piperidin-4-yl]cyclopropanecarboxamide,
(99) N-(1-{[6-(pentan-3-yloxy)-2-(pyrazolo[5,1-b][1,3]thiazol-7-yl)pyrimidin-4-yl]carbonyl}piperidin-4-yl)cyclopropanecarboxamnide,
(100) methyl[1-({6-[methyl(pentan-3-yl)amino]-2-(pyrazolo[5,1-b][1,3]thiazol-7-yl)pyrimidin-4-yl}carbonyl)piperidin-4-yl]carbamate,
(101) methyl(1-{[6-{[(2R)-3,3-dimethylbutan-2-yl](methyl)amino}-2-(pyrazolo[5,1-b][1,3]thiazol-7-yl)pyrimidin-4-yl]carbonyl}piperidin-4-yl)carbamate,
(102) N-(1-{[6-(2-ethylbutoxy)-2-(pyrazolo[5,1-b][1,3]thiazol-7-yl)pyrimidin-4-yl]carbonyl}piperidin-4-yl)propanamide,
(103) N-(1-{[6-{[(2R)-3,3-dimethylbutan-2-yl](methyl)amino}-2-(pyrazolo[5,1-b][1,3]thiazol-7-yl)pyrimidin-4-yl]carbonyl}piperidin-4-yl)propanamide,
(104) N-[1-({6-[methyl(pentan-3-yl)amino]-2-(pyrazolo[5,1-b][1,3]thiazol-7-yl)pyrimidin-4-yl}carbonyl)piperidin-4-yl]propanamide,
(105) [6-{[(2R)-3,3-dimethylbutan-2-yl]amino}-2-(pyrazolo[5,1-b][1,3]thiazol-7-yl)pyrimidin-4-yl]{4-[(3-fluoropyridin-2-yl)amino]piperidin-1-yl}methanone,
(106) N-[1-({6-[(2-methoxy-2-methylpropyl)amino]-2-(pyrazolo[5,1-b][1,3]thiazol-7-yl)pyrimidin-4-yl)carbonyl}piperidin-4-yl]propanamide,
(107) (4-hydroxypiperidin-1-yl) {6-[methyl(pentan-3-yl)amino]-2-(pyrazolo[5,1-b][1,3]thiazol-7-yl)pyrimidin-4-yl}methanone,
(108) N-(1-{[6-{[(2R)-3-methylbutan-2-yl]amino}-2-(pyrazolo[5,1-b][1,3]thiazol-7-yl)pyrimidin-4-yl]carbonyl}piperidin-4-yl)propanamide,
(109) N-(1-{[6-{[(2R)-3-methylbutan-2-yl]amino}-2-(pyrazolo[5,1-b][1,3]thiazol-7-yl)pyrimidin-4-yl]carbonyl}piperidin-4-yl)cyclopropanecarboxamide,
(110) N-(1-{[6-{[(2S)-3-methylbutan-2-yl]amino}-2-(pyrazolo[5,1-b][1,3]thiazol-7-yl)pyrimidin-4-yl]carbonyl}piperidin-4-yl)cyclopropanecarboxamide,
(111) N-(1-{[6-(pentan-3-ylamino)-2-(pyrazolo[5,1-b][1,3]thiazol-7-yl)pyrimidin-4-yl]carbonyl}piperidin-4-yl)cyclopropanecarboxamide,
(112) methyl[1-({6-[(2S)-butan-2-ylamino]-2-(pyrazolo[5,1-b][1,3]thiazol-7-yl)pyrimidin-4-yl)carbonyl}piperidin-4-yl]carbamate,
(113) methyl[1-({6-[(2R)-butan-2-ylamino]-2-(pyrazolo[5,1-b][1,3]thiazol-7-yl)pyrimidin-4-yl}carbonyl)piperidin-4-yl]carbamate,
(114) N-[1-({6-[(1-methylcyclopropyl)amino]-2-(pyrazolo[5,1-b][1,3]thiazol-7-yl)pyrimidin-4-yl}carbonyl)piperidin-4-yl]propanamide,
(115) [6-{[(2R)-3,3-dimethylbutan-2-yl]amino}-2-(pyrazolo[5,1-b][1,3]thiazol-7-yl)pyrimidin-4-yl]{4-[(5-fluoropyridin-2-yl)amino]piperidin-1-yl}methanone,
(116) 2-methyl-N-[1-({6-[(2-methylbutan-2-yl)amino]-2-(pyrazolo[5,1-b][1,3]thiazol-7-yl)pyrimidin-4-yl)carbonyl}piperidin-4-yl]propanamide, (117) N-[1-({6-[(2S)-butan-2-ylamino]-2-(pyrazolo[5,1-b][1,3]thiazol-7-yl)pyrimidin-4-yl}carbonyl)piperidin-4-yl]propanamide,
(118) methyl[1-({6-[tert-butyl(methyl)amino]-2-(pyrazolo[5,1-b][1,3]thiazol-7-yl)pyrimidin-4-yl}carbonyl)piperidin-4-yl]carbamate,
(119) cyclopropyl(1-{[6-{[(1S)-1-cyclopropylethyl]amino}-2-(pyrazolo[5,1-b][1,3]thiazol-7-yl)pyrimidin-4-yl]carbonyl)}piperidin-4-yl)carbamate,
(120) cyclopropyl(1-{[6-(tert-butylamino)-2-(pyrazolo[5,1-b][1,3]thiazol-7-yl)pyrimidin-4-yl]carbonyl}piperidin-4-yl)carbamate,
(121) 2,2-difluoro-N-(1-{[6-{[(2R)-3-methylbutan-2-yl]amino}-2-(pyrazolo[5,1-b][1,3]thiazol-7-yl)pyrimidin-4-yl]carbonyl}piperidin-4-yl)acetamide,
(122) 3-[1-({6-[(2,2-dimethylpropyl)amino]-2-(pyrazolo[5,1-b][1,3]thiazol-7-yl)pyrimidin-4-yl}carbonyl)piperidin-4-yl]-1,1-dimethylurea,
(123) 3-(1-{[6-{[(1R)-1-cyclopropylethyl]amino}-2-(pyrazolo[5,1-b][1,3]thiazol-7-yl)pyrimidin-4-yl]carbonyl}piperidin-4-yl)-1,1-dimethylurea,
(124) propan-2-yl[1-({6-[(3-methyloxetan-3-yl)amino]-2-(pyrazolo[5,1-b][1,3]thiazol-7-yl)pyrimidin-4-yl}carbonyl)piperidin-4-yl]carbamate,
(125) methyl[1-({6-[(dicyclopropylmethyl)amino]-2-(pyrazolo[5,1-b][1,3]thiazol-7-yl)pyrimidin-4-yl}carbonyl)piperidin-4-yl]carbamate,
(126) methyl(1-f{[6-phenoxy-2-(pyrazolo[5,1-b][1,3]thiazol-7-yl)pyrimidin-4-yl]carbonyl}piperidin-4-yl)carbamate,
(127) tert-butyl 4-{[6-({4-[(methoxycarbonyl)amino]piperidin-1-yl}carbonyl)-2-(pyrazolo[5,1-b][1,3]thiazol-7-yl)pyrimidin-4-yl]amino}piperidine-1-carboxylate,
(128) methyl(1-{[6-(piperidin-4-ylamino)-2-(pyrazolo[5,1-b][1,3]thiazol-7-yl)pyrimidin-4-yl]carbonyl}piperidin-4-yl)carbamate,
(129) methyl[1-({6-[(1-cyanocyclopropyl)amino]-2-(pyrazolo[5,1-b][1,3]thiazol-7-yl)pyrimidin-4-yl}carbonyl)piperidin-4-yl]carbamate,
(130) methyl(1-{[6-{[(1S)-1-cyclopropylethyl]amino}-5-methoxy-2-(pyrazolo[5,1-b][1,3]thiazol-7-yl)pyrimidin-4-yl]carbonyl}piperidin-4-yl)carbamate,
(131) methyl(1-{[6-{[(2R)-3,3-dimethylbutan-2-yl]amino}-5-methoxy-2-(pyrazolo[5,1-b][1,3]thiazol-7-yl)pyrimidin-4-yl]carbonyl}piperidin-4-yl)carbamate,
(132) methyl[1-({6-[(2S)-butan-2-ylamino]-5-methoxy-2-(pyrazolo[5,1-b][1,3]thiazol-7-yl)pyrimidin-4-yl}carbonyl)piperidin-4-yl]carbamate,
(133) methyl(1-{[6-{[(1S)-1-cyclopropylethyl]amino}-5-ethoxy-2-(pyrazolo[5,1-b][1,3]thiazol-7-yl)pyrimidin-4-yl]carbonyl}piperidin-4-yl)carbamate,
(134) methyl(1-{[6-{[(2R)-3,3-dimethylbutan-2-yl]amino}-5-ethoxy-2-(pyrazolo[5,1-b][1,3]thiazol-7-yl)pyrimidin-4-yl]carbonyl}piperidin-4-yl)carbamate, and
(135) methyl(1-{[2-(pyrazolo[5,1-b][1,3]thiazol-7-yl)-6-(pyridin-3-yloxy)pyrimidin-4-yl]carbonyl}piperidin-4-yl)carbamate,
or a pharmaceutically acceptable salt thereof, or a solvate thereof.

(VII) The pyrazolothiazole compound described in (I) which is any one of the following (1) to (58):
(1) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide,
(2) N-(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,
(3) N-(1-{[6-{[(1S,2S)-2-(difluoromethoxy)cyclopentyl](methyl)amino}-2-(pyrazolo[5,1-b][1,3]thiazol-7-yl)pyrimidin-4-yl]carbonyl}piperidin-4-yl)cyclopropanecarboxamide,
(4) N-(1-{[6-{[(2S)-3,3-dimethylbutan-2-yl]amino}-5-methyl-2-(pyrazolo[5,1-b][1,3]thiazol-7-yl)pyrimidin-4-yl]carbonyl}piperidin-4-yl)cyclopropanecarboxamide,
(5) N-[1-({6-[({1-[(difluoromethoxy)methyl]cyclopropyl}methyl)amino]-2-(pyrazolo[5,1-b][1,3]thiazol-7-yl)pyrimidin-4-yl}carbonyl)piperidin-4-yl]cyclopropanecarboxamide,
(6) N-[1-({6-[({1-[(difluoromethoxy)methyl]cyclobutyl}methyl)amino]-2-(pyrazolo[5,1-b][1,3]thiazol-7-yl)pyrimidin-4-yl}carbonyl)piperidin-4-yl]cyclopropanecarboxamide,
(7) N-[1-({6-[({1-[(difluoromethoxy)methyl]cyclopentyl}methyl)amino]-2-(pyrazolo[5,1-b][1,3]thiazol-7-yl)pyrimidin-4-yl}carbonyl)piperidin-4-yl]cyclopropanecarboxamide,
(8) N-[1-({6-[({4-[(difluoromethoxy)methyl]tetrahydro-2H-pyran-4-yl}methyl)amino]-2-(pyrazolo[5,1-b][1,3]thiazol-7-yl)pyrimidin-4-yl}carbonyl)piperidin-4-yl]cyclopropanecarboxamide,
(9) N-(1-({[6-{[(1S)-1-cyclopropylethyl]amino}-5-methyl-2-(pyrazolo[5,1-b][1,3]thiazol-7-yl)pyrimidin-4-yl]carbonyl}piperidin-4-yl)cyclopropanecarboxamide,
(10) N-(1-{[6-{[(1S,2S)-2-(difluoromethoxy)cyclopentyl]amino}-2-(pyrazolo[5,1-b][1,3]thiazol-7-yl)pyrimidin-4-yl]carbonyl}piperidin-4-yl)cyclopropanecarboxamide,
(11) N-[1-({6-[(2,2-dimethylpropyl)amino]-2-(pyrazolo[5,1-b][1,3]thiazol-7-yl)pyrimidin-4-yl}carbonyl)piperidin-4-yl]cyclopropanecarboxamide,
(12) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,
(13) N-(1-{[6-{[(2S)-1-(difluoromethoxy)propan-2-yl]amino}-2-(pyrazolo[5,1-b][1,3]thiazol-7-yl)pyrimidin-4-yl]carbonyl}piperidin-4-yl)cyclopropanecarboxamide,
(14) methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(15) ethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(16) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)benzamide,
(17) N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide,
(18) propan-2-yl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(19) N-(1-{[6-(cyclopropylmethoxy)-2-(pyrazolo[5,1-b][1,3]thiazol-7-yl)pyrimidin-4-yl]carbonyl}piperidin-4-yl)cyclopropanecarboxamide,
(20) N-[1-({6-[(3,3-dimethylbutan-2-yl)oxy]-2-(pyrazolo[5,1-b][1,3]thiazol-7-yl)pyrimidin-4-yl}carbonyl)piperidin-4-yl]cyclopropanecarboxamide,
(21) N-(1-{[6-(cyclobutyloxy)-2-(pyrazolo[5,1-b][1,3]thiazol-7-yl)pyrimidin-4-yl]carbonyl}piperidin-4-yl)cyclopropanecarboxamide,
(22) N-[1-({6-[(1-hydroxy-2-methylpropan-2-yl)amino]-2-(pyrazolo[5,1-b][1,3]thiazol-7-yl)pyrimidin-4-yl}carbonyl)piperidin-4-yl]cyclopropanecarboxamide,

(23) [6-{[(1S)-1-cyclopropylethyl]amino}-2-(pyrazolo[5,1-b][1,3]thiazol-7-yl)pyrimidin-4-yl][4-(1,3-thiazol-2-ylamino)piperidin-1-yl]methanone,
(24) N-(1-{[6-{[(2S)-1-hydroxy-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,
(25) methyl(1-{[6-(tert-butylamino)-2-(pyrazolo[5,1-b][1,3]thiazol-7-yl)pyrimidin-4-yl]carbonyl}piperidin-4-yl)carbamate,
(26) propan-2-yl(1-{[6-(tert-butylamino)-2-(pyrazolo[5,1-b][1,3]thiazol-7-yl)pyrimidin-4-yl]carbonyl}piperidin-4-yl)carbamate,
(27) methyl[1-({6-[(1-hydroxy-2-methylpropan-2-yl)amino]-2-(pyrazolo[5,1-b][1,3]thiazol-7-yl)pyrimidin-4-yl}carbonyl)piperidin-4-yl]carbamate,
(28) [6-{[(2R)-3,3-dimethylbutan-2-yl]amino}-2-(pyrazolo[5,1-b][1,3]thiazol-7-yl)pyrimidin-4-yl](4-hydroxypiperidin-1-yl)methanone,
(29) methyl(1-{[6-{[(2S)-1-hydroxy-3,3-dimethylbutan-2-yl]amino}-2-(pyrazolo[5,1-b][1,3]thiazol-7-yl)pyrimidin-4-yl]carbonyl}piperidin-4-yl)carbamate,
(30) methyl[1-({6-[(3,3-dimethylbutan-2-yl)oxy]-2-(pyrazolo[5,1-b][1,3]thiazol-7-yl)pyrimidin-4-yl}carbonyl)piperidin-4-yl]carbamate,
(31) methyl(1-{[6-(cyclobutyloxy)-2-(pyrazolo[5,1-b][1,3]thiazol-7-yl)pyrimidin-4-yl]carbonyl}piperidin-4-yl)carbamate,
(32) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanesulfonamide,
(33) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)ethanesulfonamide,
(34) ethyl(1-{[6-(tert-butylamino)-2-(pyrazolo[5,1-b][1,3]thiazol-7-yl)pyrimidin-4-yl]carbonyl}piperidin-4-yl)carbamate,
(35) [6-(tert-butylamino)-2-(pyrazolo[5,1-b][1,3]thiazol-7-yl)pyrimidin-4-yl][4-(pyridin-2-ylamino)piperidin-1-yl]methanone,
(36) propyl(1-{[6-(tert-butylamino)-2-(pyrazolo[5,1-b][1,3]thiazol-7-yl)pyrimidin-4-yl]carbonyl}piperidin-4-yl)carbamate,
(37) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)-2-methoxyacetamide,
(38) 2,2-difluoroethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(39) 2,2-difluoroethyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate,
(40) tert-butyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(41) 2-methoxyethyl(1-{[6-(tert-butylamino)-2-(pyrazolo[5,1-b][1,3]thiazol-7-yl)pyrimidin-4-yl]carbonyl}piperidin-4-yl)carbamate,
(42) 2-(dimethylamino)ethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(43) 2,2,2-trifluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate,
(44) 2,2,2-trifluoroethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate,
(45) methyl(1-{[6-(pentan-3-yloxy)-2-(pyrazolo[5,1-b][1,3]thiazol-7-yl)pyrimidin-4-yl]carbonyl}piperidin-4-yl)carbamate,
(46) N-[1-({6-[(2-ethylbutyl)amino]-2-(pyrazolo[5,1-b][1,3]thiazol-7-yl)pyrimidin-4-yl}carbonyl)piperidin-4-yl]cyclopropanecarboxamide,
(47) N-(1-{[6-(pentan-3-yloxy)-2-(pyrazolo[5,1-b][1,3]thiazol-7-yl)pyrimidin-4-yl]carbonyl}piperidin-4-yl)cyclopropanecarboxamide,
(48) methyl[1-({6-[(2S)-butan-2-ylamino]-2-(pyrazolo[5,1-b][1,3]thiazol-7-yl)pyrimidin-4-yl) carbonyl}piperidin-4-yl]carbamate,
(49) methyl[1-({6-[(2R)-butan-2-ylamino]-2-(pyrazolo[5,1-b][1,3]thiazol-7-yl)pyrimidin-4-yl}carbonyl)piperidin-4-yl]carbamate,
(50) N-[1-({6-[(1-methylcyclopropyl)amino]-2-(pyrazolo[5,1-b][1,3]thiazol-7-yl)pyrimidin-4-yl}carbonyl)piperidin-4-yl]propanamide,
(51) methyl[1-({6-[tert-butyl(methyl)amino]-2-(pyrazolo[5,1-b][1,3]thiazol-7-yl)pyrimidin-4-yl}carbonyl)piperidin-4-yl]carbamate,
(52) cyclopropyl(1-{[6-(tert-butylamino)-2-(pyrazolo[5,1-b][1,3]thiazol-7-yl)pyrimidin-4-yl]carbonyl}piperidin-4-yl)carbamate,
(53) propan-2-yl[1-({6-[(3-methyloxetan-3-yl)amino]-2-(pyrazolo[5,1-b][1,3]thiazol-7-yl)pyrimidin-4-yl}carbonyl)piperidin-4-yl]carbamate,
(54) methyl[1-({6-[(1-cyanocyclopropyl)amino]-2-(pyrazolo[5,1-b][1,3]thiazol-7-yl)pyrimidin-4-yl}carbonyl)piperidin-4-yl]carbamate,
(55) methyl[1-({6-[(2S)-butan-2-ylamino]-5-methoxy-2-(pyrazolo[5,1-b][1,3]thiazol-7-yl)pyrimidin-4-yl}carbonyl)piperidin-4-yl]carbamate,
(56) methyl(1-{[6-{[(1S)-1-cyclopropylethyl]amino}-5-ethoxy-2-(pyrazolo[5,1-b][1,3]thiazol-7-yl)pyrimidin-4-yl]carbonyl}piperidin-4-yl)carbamate,
(57) methyl(1-{[6-({[(2R)-3,3-dimethylbutan-2-yl]amino}-5-ethoxy-2-(pyrazolo[5,1-b][1,3]thiazol-7-yl)pyrimidin-4-yl]carbonyl}piperidin-4-yl)carbamate, and
(58) methyl(1-{[2-(pyrazolo[5,1-b][1,3]thiazol-7-yl)-6-(pyridin-3-yloxy)pyrimidin-4-yl]carbonyl}piperidin-4-yl)carbamate,
or a pharmaceutically acceptable salt thereof, or a solvate thereof.
(VIII) The pyrazolothiazole compound described in (I) which is any one of the following (1) to (8):
(1) N-(1-[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide,
(2) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,
(3) methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(4) ethyl(1-[6-{[(1S)-1-cyclopropylethyl]amino}-2-(pyrazolo[5,1-b][1,3]thiazol-7-yl)pyrimidin-4-yl]carbonyl piperidin-4-yl)carbamate,
(5) N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide,
(6) propan-2-yl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
(7) methyl[1-({6-[(2S)-butan-2-ylamino]-2-(pyrazolo[5,1-b][1,3]thiazol-7-yl)pyrimidin-4-yl}carbonyl)piperidin-4-yl]carbamate, and (8) methyl[1-({6-[(2R)-butan-2-ylamino]-2-(pyrazolo[5,1-b][1,3]thiazol-7-yl)pyrimidin-4-yl}carbonyl)piperidin-4-yl]carbamate,
or a pharmaceutically acceptable salt thereof, or a solvate thereof.

(IX) A pharmaceutical composition comprising the pyrazolothiazole compound or a pharmaceutically acceptable salt thereof or a solvate thereof according to any one of (I) to (VIII) as an active ingredient.

(X) A JAK1 inhibitor comprising the pyrazolothiazole compound or a pharmaceutically acceptable salt thereof or a solvate thereof according to any one of (I) to (VIII) as an active ingredient.

(XI) A therapeutic agent for an inflammatory disease, comprising the pyrazolothiazole compound or a pharmaceutically acceptable salt thereof or a solvate thereof according to any one of (I) to (VIII) as an active ingredient.

(XII) The therapeutic agent according to (XI) wherein the inflammatory disease is atopic dermatitis, eczema, bronchial asthma, eosinophilic pneumonia, chronic obstructive pulmonary disease, allergic rhinitis, eosinophilic sinusitis, nasal polyp, ankylosing spondylitis or eosinophilic esophagitis.

(XIII) A therapeutic agent for an autoimmune disease, comprising the pyrazolothiazole compound or a pharmaceutically acceptable salt thereof or a solvate thereof according to any one of (I) to (VIII) as an active ingredient.

(XIV) The therapeutic agent according to (XIII) wherein the autoimmune disease is rheumatoid arthritis, psoriatic arthritis, juvenile arthritis, Castleman's disease, systemic lupus erythematosus, Sjögren's syndrome, inflammatory bowel disease, psoriasis, scleroderma, dry eye, Takayasu's arteritis, giant cell arteritis, microscopic polyangiitis, granulomatosis with polyangiitis, eosinophilic granulomatosis with polyangiitis or neuromyelitis optica.

(XV) A therapeutic agent for a proliferative disease, comprising the pyrazolothiazole compound or a pharmaceutically acceptable salt thereof or a solvate thereof according to any one of (I) to (VIII) as an active ingredient.

(XVI) The therapeutic agent according to (XV) wherein the proliferative disease is solid cancers, blood cancers, lymph malignant tumor, myeloproliferative diseases, multiple myeloma, pulmonary fibrosis or eosinophilia.

(XVII) A therapeutic agent for diabetic nephropathy, alopecia areata, bone marrow transplant rejection or organ transplant rejection, comprising the pyrazolothiazole compound or a pharmaceutically acceptable salt thereof or a solvate thereof according to any one of (I) to (VIII) as an active ingredient.

The terms as used herein are defined below.

The term "halogen" represents fluorine, chlorine, bromine or iodine atom. Specially, fluorine atom is preferable.

The term "alkyl" includes, for example, an alkyl of straight or branched chain having 1 to 10 carbon atoms, preferably 1 to 8 carbon atoms, more preferably 1 to 6 carbon atoms. Specifically, the term may include, for example, methyl, ethyl, propyl, isopropyl, butyl, isobutyl, sec-butyl, tert-butyl, pentyl, sec-pentyl, 1-ethylpropyl, 1,2-dimethylpropyl, tert-pentyl, 2-methylbutyl, isopentyl, neopentyl, n-hexyl, sec-hexyl, 1-ethylbutyl, isohexyl, neohexyl, 1,1-dimethylbutyl, thexyl, 2-ethylbutyl, 1,2,2-trimethylpropyl, 2,2-dimethylbutyl, heptyl, isoheptyl, octyl and isooctyl.

Examples of the alkyl moiety in "(difluoroalkoxy)alkyl", "alkoxyalkyl", "dialkylamino", "dialkylaminoalkyl", "alkylcarbonyl", "monohaloalkyl", "dihaloalkyl", "trihaloalkyl" may include the same as described above for "alkyl".

The term "monohaloalkyl" refers to a group wherein an "alkyl" as defined above is substituted with a "halogen" as defined above. Specifically, the term may include, for example, monofluoromethyl, monochloromethyl and monofluoroethyl.

The term "dihaloalkyl" refers to a group wherein an "alkyl" as defined above is substituted with two "halogens" as defined above. Specifically, the term may include, for example, difluoromethyl, difluoroethyl and 1,2-difluoropropyl.

The term "trihaloalkyl" refers to a group wherein an "alkyl" as defined above is substituted with three "halogens" as defined above. Specifically, the term may include, for example, trifluoromethyl, trichloromethyl and trifluoroethyl.

The term "alkoxy" may include, for example, a straight or branched chain alkoxy having 1 to 8 carbon atoms, preferably 1 to 6 carbon atoms. Specifically, the term may include methoxy, ethoxy, n-propoxy, isopropoxy, n-butoxy, isobutoxy, sec-butoxy, tert-butoxy, n-pentyloxy, n-hexyloxy, n-heptyloxy and n-octyloxy.

Examples of the alkoxy moiety in "(difluoroalkoxy)alkyl", "alkoxyalkyl" may include the same as those described above for "alkoxy".

The term "cycloalkyl" may include, for example, mono- to tri-cyclic saturated hydrocarbon group having 3 to 10 carbon atoms. Monocyclic cycloalkyl having 3 to 6 carbon atoms is preferable. Specifically, the term may include cyclopropyl, cyclobutyl, cyclopentyl, cyclohexyl, cycloheptyl, bicyclo[2.1.0]pentyl, bicyclo[2.2.1]heptyl, and bicyclo[2.2.2]octyl.

For the "cycloalkyl" represented by $L^1$, monocyclic cycloalkyl having 3 to 6 carbon atoms is preferred, and cyclopropyl is more preferable.

For the "cycloalkyl" moiety in "cycloalkylamino", cyclopropyl is preferable.

The term "aryl" refers to, for example, a mono- to tri-cyclic aromatic hydrocarbon group having 6 to 14 carbon atoms. Specifically, the term may include phenyl, 1-naphthyl, 2-naphthyl, 1-anthryl, 2-anthryl, 9-anthryl, 1-phenanthryl, 2-phenanthryl, 3-phenanthryl, 4-phenanthryl and 10-phenanthryl. Especially, phenyl is preferable.

The term "heteroaryl" may include, for example, a 5- to 10-membered mono- to bi-cyclic aromatic heterocyclic group having 1 to 4 heteroatoms selected from the group consisting of nitrogen atom, sulfur atom and oxygen atom within the ring. Specifically, the term may include furyl (e.g., 2-furyl and 3-furyl), thienyl(e.g., 2-thienyl and 3-thienyl), pyrrolyl(e.g., 2-pyrrolyl and 3-pyrrolyl), imidazolyl (e.g., 2-imidazolyl and 4-imidazolyl), pyrazolyl (e.g., 3-pyrazolyl and 4-pyrazolyl), triazolyl(e.g., 1,2,4-triazol-3-yl, 1,2,4-triazol-5-yl and 1,2,3-triazol-4-yl), tetrazolyl(e.g., 5-tetrazolyl), oxazolyl(e.g., 2-oxazolyl, 4-oxazolyl and 5-oxazolyl), isoxazolyl(e.g., 3-isoxazolyl, 4-isoxazolyl and 5-isoxazolyl), oxadiazolyl (e.g., 1,3,4-oxadiazol-2-yl), thiazolyl(e.g., 2-thiazolyl, 4-thiazolyl and 5-thiazolyl), thiadiazolyl, isothiazolyl (e.g., 3-isothiazolyl, 4-isothiazolyl and 5-isothiazolyl), pyridyl(e.g., 2-pyridyl, 3-pyridyl and 4-pyridyl), pyridazinyl(e.g., 3-pyridazinyl and 4-pyridazinyl), pyrimidinyl(e.g., 2-pyrimidinyl, 4-pyrimidinyl and 5-pyrimidinyl), pyrazinyl(e.g., 2-pyrazinyl), benzimidazolyl (e.g., 2-benzimidazolyl, 4-benzimidazolyl, 5-benzimidazolyl, 6-benzimidazolyl and 7-benzimidazolyl), indazolyl (e.g., 3-indazolyl, 4-indazolyl, 5-indazolyl, 6-indazolyl and 7-indazolyl) and isoquinolyl(e.g., 1-isoquinolyl, 3-isoquinolyl, 4-isoquinolyl, 5-isoquinolyl, 6-isoquinolyl, 7-isoquinolyl and 8-isoquinolyl). Preferably, the heteroaryl may be furyl(e.g., 2-furyl and 3-furyl), imidazolyl(e.g., 2-imidazolyl and 4-imidazolyl), thiazolyl (e.g., 2-thiazolyl, 4-thiazolyl and 5-thiazolyl), pyridyl (e.g., 2-pyridyl, 3-pyridyl and 4-pyridyl), pyridazinyl (e.g., 3-pyridazinyl and 4-pyridazinyl), pyrimidinyl(e.g., 2-pyrimidinyl, 4-pyrimidinyl and 5-pyrimidinyl) or pyrazinyl(e.g., 2-pyrazinyl).

For the "heteroaryl" represented by $R^3$, 3-pyridyl is preferable.

For the "heteroaryl" represented by $R^8$, isoxazolyl (e.g., 3-isoxazolyl, 4-isoxazolyl and 5-isoxazolyl), thiazolyl(e.g., 2-thiazolyl, 4-thiazolyl and 5-thiazolyl), pyrimidinyl(e.g., 2-pyrimidinyl, 4-pyrimidinyl, 5-pyrimidinyl and 6-pyrimidinyl) and pyridyl(2-pyridyl, 3-pyridyl and 4-pyridyl) are preferable, and 3-isoxazolyl, 5-isoxazolyl, 2-thiazolyl, 2-pyrimidinyl and 2-pyridyl are more preferable.

For the "heteroaryl" represented by $L^1$, thienyl(e.g., 2-thienyl and 3-thienyl) and pyridyl(e.g., 2-pyridyl, 3-pyridyl and 4-pyridyl) are more preferable.

The term "saturated heterocyclic group" may include, for example, a 3- to 8-membered saturated heterocyclic group having 1 to 3 heteroatoms selected from the group consisting of nitrogen atom, sulfur atom and oxygen atom within the ring. Specifically, the term may include oxetanyl(e.g., 2-oxetanyl and 3-oxetanyl), azetidinyl (e.g., 2-azetidinyl and 3-azetidinyl), tetrahydropyranyl (e.g., 2-tetrahydropyranyl, 3-tetrahydropyranyl and 4-tetrahydropyranyl), pyrrolidinyl (e.g., 1-pyrrolidinyl, 2-pyrrolidinyl and 3-pyrrolidinyl), piperidinyl(e.g., 2-piperidinyl, 3-piperidinyl and 4-piperidinyl), piperazinyl (e.g., 2-piperazinyl and 3-piperazinyl), morpholinyl(e.g., 2-morpholinyl and 3-morpholinyl), thiomorpholinyl(e.g., 2-thiomorpholinyl and 3-thiomorpholinyl) and tetrahydrofuryl(2-tetrahydrofuryl and 3-tetrahydrofuryl). More preferably, the term may include piperidinyl(e.g., 2-piperidinyl, 3-piperidinyl and 4-piperidinyl), tetrahydrofuryl(2-tetrahydrofuryl and 3-tetrahydrofuryl) and tetrahydropyranyl(2-tetrahydropyranyl, 3-tetrahydropyranyl, and 4-tetrahydropyranyl).

MODE FOR CARRYING OUT THE INVENTION

The compound of the invention can be produced according to, for example, the following procedures and examples as described below, or methods known in the art, using a compound or an intermediate, which is available or can be prepared easily. In the case where a starting material has a functional group that may affect the reaction in the process for the production of the compound of the invention, the starting material should be protected with an appropriate protective group according to a known method in advance. The protective group can be removed by a known method after the reaction.

Scheme 1

[Formula 2]

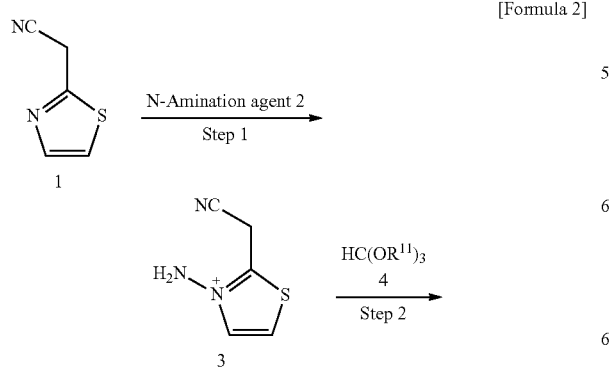

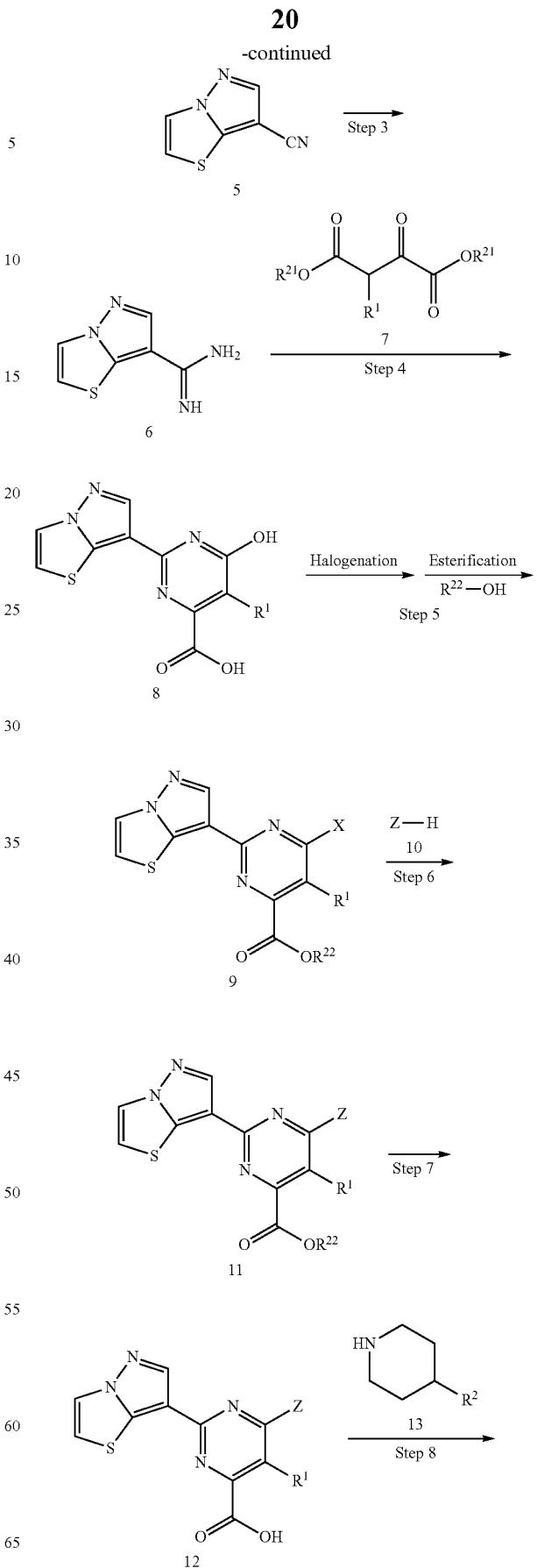

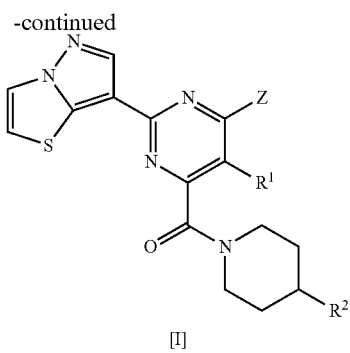

[I]

wherein, Z, $R^1$ and $R^2$ are as defined above. $R^{11}$ is alkyl, $R^{21}$ is hydrogen or alkyl, $R^{22}$ is alkyl and X is a leaving group such as halogen.

Step 1

The step is an N-amination of the compound 1 (which can be synthesized by using a method as described in, for example, Heterocycles, 2008, 75, 2005-2012) by using an N-amination agent 2 to give an N-aminothiazolium salt 3.

The N-amination agent to be used depends on the solvent employed in the reaction, and examples include but not limited to O-(mesitylenesulfonyl)hydroxyamine.

The N-amination agent may be used in an amount of 1 to 5 mole equivalent of the compound 1.

The solvent to be used in the reaction is not limited as long as it does not participate in the reaction, and the examples may include, for example, ethers such as tetrahydrofuran (hereinafter referred to as "THF"), diethyl ether, 1,4-dioxane and dimethoxyethane (hereinafter referred to as "DME"), nitriles such as acetonitrile and propionitrile, ketones such as acetone, hydrocarbons such as benzene and toluene, halogenated hydrocarbons such as chloroform, dichloromethane and 1,2-dichloroethane, and mixed solvents thereof.

The reaction temperature may be −78° C. to 100° C., preferably −78° C. to 50° C.

The reaction time may depend on the reaction temperature, and typically, it is 10 minutes to 24 hours.

Step 2

The step is the reaction of the N-aminothiazolium salt 3 with the orthoester compound 4 in an appropriate solvent to obtain the compound 5.

The solvent to be used in the reaction is not limited as long as it does not participate in the reaction, and examples of the solvent may include, ethers such as THF, diethyl ether, 1,4-dioxane and DME, nitriles such as acetonitrile and propionitrile, ketones such as acetone, hydrocarbons such as benzene and toluene, halogenated hydrocarbons such as chloroform, dichloromethane and 1,2-dichloroethane, and mixed solvents thereof. Alternatively, the orthoester compound 4 by itself may be used as the solvent in the reaction.

The reaction temperature may be 0° C. to 200° C., preferably 0° C. to 150° C.

The reaction time may depend on the reaction temperature, and typically, it is 10 minutes to 24 hours.

It is preferred that the orthoester compound 4 may be used in an amount of 1 to 50 mole equivalent of the N-aminothiazolium salt 3.

Step 3

The step is the conversion of the nitrile to an amidine, which may be conducted according to the procedure as described in, for example, Slee et al., J. Med. Chem. 2008, 51, 1719-1729. That is, the compound 5 is stirred in the presence of a base such as an alkali metal alkoxide in an appropriate solvent to obtain the imidate, and the obtained imidate is reacted with ammonia or an ammonium salt to give the amidine compound 6.

Examples of the base used in the reaction may include alkoxides such as sodium methoxide and sodium ethoxide.

It is preferred that the alkoxide may be used in an amount of 1 to 5 mole equivalent of the compound 5.

The solvent to be used in the reaction is not limited as long as it does not participate in the reaction, and, typically, an alcohol such as methanol and ethanol may be used.

In the preparation of the imidate, the reaction temperature may be 0° C. to 150° C., preferably 0° C. to 100° C.

In the preparation of the imidate, the reaction time may depend on the reaction temperature, and typically, it is 30 minutes to 24 hours.

In the preparation of the amidine compound 6, examples of the ammonium salt used in the reaction may include ammonium chloride and ammonium acetate.

The ammonium salt or ammonia may be used in an amount of 1 to 10 mole equivalent of the imidate.

The solvent to be used in the reaction is not limited as long as it does not participate in the reaction, and, typically, an alcohol such as methanol and ethanol may be used.

The reaction temperature may be −78° C. to 150° C., preferably 0° C. to 150° C.

The reaction time may depend on the reaction temperature, and typically, it is 30 minutes to 24 hours.

The ammonium salt may be added directly to the reaction mixture wherein the imidate has been prepared.

Step 4

The step is the reaction of the amidine compound 6 with an oxaloacetic acid compound 7 or a salt thereof in the presence of a base such as potassium hydroxide in an appropriate solvent to obtain the pyrimidine compound 8. The step may be conducted according to the procedure as described in, for example, WO 2009/138712.

Examples of the base used in the reaction may include inorganic bases such as sodium hydroxide, potassium hydroxide, lithium hydroxide, sodium hydrogen carbonate, sodium carbonate, potassium carbonate and cesium carbonate, and alkoxides such as sodium methoxide, sodium ethoxide and potassium tert-butoxide.

The base may be used in an amount of 1 to 50 mole equivalent of the amidine compound 6.

The solvent to be used in the reaction is not limited as long as it does not participate in the reaction, and examples may include, for example, ethers such as THF, 1,4-dioxane and DME, alcohols such as methanol and ethanol, ketones such as acetone, water, and mixed solvents thereof.

In this reaction, the reaction temperature may be 0° C. to 200° C., preferably 0° C. to 150° C.

In this reaction, the reaction time may depend on the reaction temperature, and typically, it is 30 minutes to 24 hours.

Step 5

The step is the process to obtain the compound 9 by halogenation of the pyrimidine compound 8 in the presence of a halogenating agent in an appropriate solvent at 0° C. to 180° C., followed by esterification of the obtained acid halide.

In the halogenation reaction, examples of the halogenating agent may include phosphorus oxychloride, phosphorus oxybromide and phosphorus pentachloride. These halogenating agents may be used alone or in combination thereof in the reaction.

In the halogenation reaction, a base is optionally used. Examples of the base used may include diethylaniline, pyridine, 2,6-lutidine, N,N-diisopropylethylamine (hereinafter referred to as "DIPEA") and triethylamine (hereinafter referred to as "TEA").

The halogenating agent and the base may be used in an amount of 1 to 100 mole equivalent of the pyrimidine compound 8.

The solvent to be used in the reaction is not limited as long as it does not participate in the reaction, and examples may include, ethers such as THF, diethyl ether, 1,4-dioxane and DME, amides such as N,N-dimethylformamide (hereinafter referred to as "DMF"), N,N-dimethylacetamide, N-methylpyrrolidone (hereinafter referred to as "NMP"), nitriles such as acetonitrile and propionitrile, ketones such as acetone, hydrocarbons such as benzene and toluene, halogenated hydrocarbons such as chloroform, dichloromethane and 1,2-dichloroethane, sulfoxides such as dimethyl sulfoxide (hereinafter referred to as "DMSO"), and mixed solvents thereof.

The reaction temperature may be 0° C. to 200° C., preferably 0° C. to 150° C.

The reaction time may depend on the reaction temperature, and typically, it is 10 minutes to 48 hours.

The esterification reaction may be conducted according to a common method. Examples of the alcohol ($R^{22}$—OH) used in the reaction may include methanol and ethanol.

In the esterification reaction, a base is optionally used. Examples of the base used may include organic bases such as diethylaniline, pyridine, 2,6-lutidine, DIPEA and TEA, and inorganic bases such as sodium hydrogen carbonate.

The alcohol and the base may be used in an amount of 1 to 100 mole equivalent of the acid halide.

In the esterification reaction, the solvent to be used in the reaction is not limited as long as it does not participate in the reaction, and examples include ethers such as THF, diethyl ether, 1,4-dioxane and DME, amides such as DMF and N,N-dimethylacetamide, nitriles such as acetonitrile and propionitrile, ketones such as acetone, hydrocarbons such as benzene and toluene, halogenated hydrocarbons such as chloroform, dichloromethane and 1,2-dichloroethane, sulfoxides such as DMSO, and mixed solvents thereof. Also, the alcohol to be reacted may be used as the solvent.

The reaction temperature may be −78° C. to 200° C., preferably 0° C. to 50° C.

The reaction time may depend on the reaction temperature, and typically, it is 10 minutes to 48 hours.

Step 6

The step is the reaction of the compound 9 with the compound 10 (alcoholic compound $R^3OH$ or amine compound $NHR^4R^5$) in an appropriate solvent to obtain the compound 11.

In the reaction, the compound 10 may be used in an amount of 1 to 10 mole equivalent of the compound 9.

The reaction may be conducted in the presence of an acid or a base, as necessary. Examples of the acid used may include, inorganic acids such as hydrochloric acid and sulfuric acid. Examples of the base used may include organic bases such as TEA, DIPEA, N,N-dimethylaniline, pyridine, DMAP and 1,8-diazabicyclo[5.4.0]-7-undecen, inorganic bases such as sodium hydroxide, potassium hydroxide, lithium hydroxide, sodium hydrogen carbonate, sodium carbonate, potassium carbonate and cesium carbonate, alkoxides such as sodium methoxide, sodium ethoxide and potassium tert-butoxide, and alkali metal hydrides such as sodium hydride and potassium hydride.

The solvent to be used in the reaction is not limited as long as it does not participate in the reaction, and examples include ethers such as THF, diethyl ether, 1,4-dioxane and DME, nitriles such as acetonitrile and propionitrile, ketones such as acetone, halogenated hydrocarbons such as chloroform, dichloromethane and 1,2-dichloroethane, hydrocarbons such as toluene, benzene and cyclohexane, alcohols such as methanol, ethanol, isopropylalcohol and butanol, amides such as DMF, N,N-dimethylacetamide, and NMP, sulfoxides such as DMSO, and mixed solvents thereof.

In this reaction, the reaction temperature may be 0° C. to 200° C., preferably 0° C. to 150° C. If necessary, the reaction may be conducted by using microwave or in a closed condition.

The reaction time may depend on the type of starting materials and the base and the reaction temperature, and typically, it is 30 minutes to 48 hours.

Step 7

The step is hydrolysis reaction of the ester compound 11 in the presence of an appropriate acid or base in an appropriate solvent to obtain the carboxylic acid 12.

In the reaction, examples of the acid used may include inorganic acids such as hydrochloric acid and sulfuric acid, and organic acids such as trifluoroacetic acid (hereinafter referred to as "TFA"), methanesulfonic acid and toluenesulfonic acid. Examples of the base may include inorganic bases such as sodium hydroxide, potassium hydroxide and lithium hydroxide.

In the reaction, the acid or base may be used in an amount of 1 to 10 mole equivalent of the ester compound 11.

The solvent to be used in the reaction is not limited as long as it does not participate in the reaction, and examples include water, alcohols such as methanol, ethanol and isopropanol, ethers such as THF, diethyl ether, 1,4-dioxane and DME, nitriles such as acetonitrile and propionitrile, ketones such as acetone, and mixed solvents thereof.

In this reaction, the reaction temperature may be −78° C. to 200° C., preferably 0° C. to 100° C.

The reaction time may depend on the reaction temperature, and typically, it is 30 minutes to 48 hours.

Step 8

The step is the condensation reaction of the carboxylic acid 12 and the compound 13 in an appropriate solvent to obtain compound [I]. The compound [I] can be prepared by reacting the carboxylic acid 12 or its reactive derivative with the compound 13.

Examples of the reactive derivatives of the carboxylic acid 12 may include, those commonly used in the amide condensation formation reaction such as acid halides (e.g., acid chloride and acid bromide), mixed anhydrides, imidazolides and reactive amides.

When using the carboxylic acid 12, a condensing agent such as 1,1'-carbonyldiimidazole, 1-ethyl-3-(3-dimethylaminopropyl)carbodiimide (hereinafter referred to as "WSCD (Water Soluble Carbodiimide)"), N,N'-dicyclohexylcarbodiimide (hereinafter referred to as "DCC"), O-(7-azabenzotriazol-1-yl)-1,1,3,3-tetramethyluronium hexafluorophosphate (hereinafter referred to as "HATU"), O-(benzotriazol-1-yl)-N,N,N',N'-tetramethyluronium hexafluorophosphate (hereinafter referred to as "HBTU"), diethyl cyanophosphonate, diphenylphosphoryl azide, 2-chloro-1-methylpyridinium iodide, 1H-benzotriazol-1-yloxytripyrrolizinophosphonium hexafluorophosphate or benzotriazol-1-yloxytris(dimethylamino)phosphonium hexafluorophosphate can be used.

In the reaction, the condensing agent may be used in an amount of 1 to 3 mole equivalent of the carboxylic acid 12.

The reaction may be conducted in the presence of a base, as necessary. Examples of the base used may include, for example, organic bases such as TEA, DIPEA, N,N-dimethylaniline, pyridine, DMAP and 1,8-diazabicyclo[5.4.0]-7-undecene.

An additive such as 1-hydroxybenzotriazole (hereinafter referred to as "HOBt") and N-hydroxysuccinimide can be added to the reaction.

The solvent to be used in the reaction is not limited as long as it does not participate in the reaction, and examples include ethers such as THF, diethyl ether, 1,4-dioxane and DME, amides such as DMF and N,N-dimethylacetamide, nitriles such as acetonitrile and propionitrile, ketones such as acetone, hydrocarbons such as benzene and toluene, halogenated hydrocarbons such as chloroform and dichloromethane, and mixed solvents thereof.

The reaction temperature may be −78° C. to 200° C., preferably −20° C. to 50° C.

The reaction time may depend on the type of starting materials and condensing agents and the reaction temperature, and typically, it is 10 minutes to 24 hours.

The compound [I] also may be prepared according to the following Scheme 2.

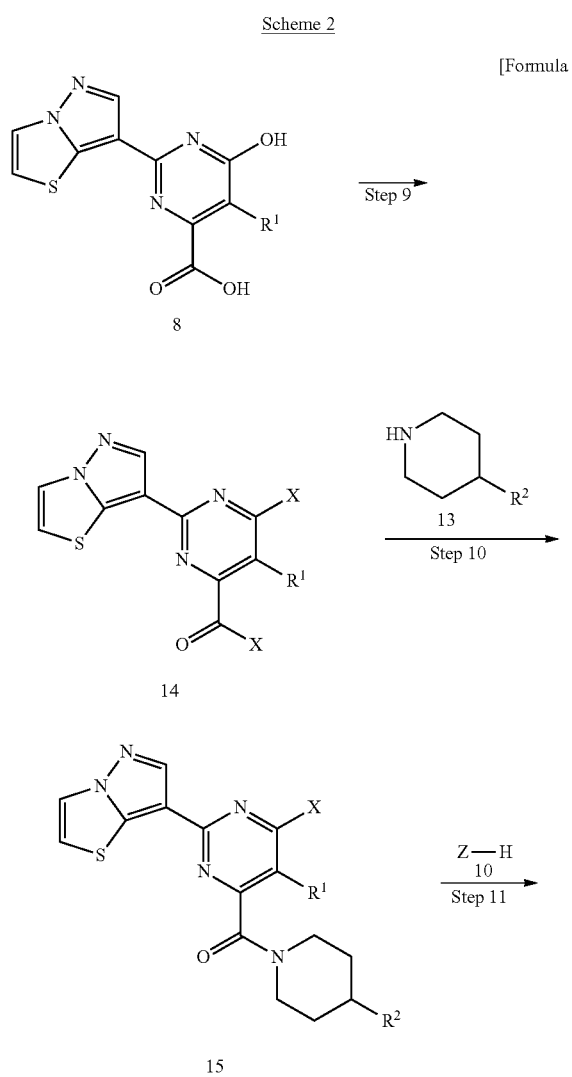

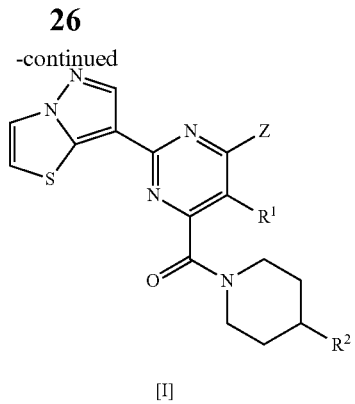

wherein, Z, $R^1$ and $R^2$ are as defined above. X is halogen.

Step 9

The step is halogenation reaction of the hydroxide moiety of the compound 8 with a halogenating agent, such as phosphorus oxychloride in an appropriate solvent, to obtain the acid halide 14. The step may be conducted as described in Step 5

Step 10

The step is a reaction of the acid halide 14 with the amine compound 13 in an appropriate solvent to obtain the amide compound 15.

In the reaction, the compound 13 may be used in an amount of 1 to 3 mole equivalent of the compound 14.

The reaction may be conducted in the presence of a base, as necessary. Examples of the base used may include organic bases such as TEA, DIPEA, N,N-dimethylaniline, pyridine, DMAP and 1,8-diazabicyclo[5.4.0]-7-undecene, and inorganic bases such as sodium hydrogen carbonate, sodium carbonate, potassium carbonate and cesium carbonate.

The solvent to be used in the reaction is not limited as long as it does not participate in the reaction, and examples include ethers such as THF, diethyl ether, 1,4-dioxane and DME, nitriles such as acetonitrile and propionitrile, ketones such as acetone, halogenated hydrocarbons such as chloroform, dichloromethane and 1,2-dichloroethane, hydrocarbons such as toluene, benzene and cyclohexane, amides such as DMF and N,N-dimethylacetamide, sulfoxides such as DMSO, and mixed solvents thereof.

In this reaction, the reaction temperature may be −50° C. to 100° C., preferably 0° C. to 50° C.

The reaction time may depend on the type of starting materials and bases and the reaction temperature, and typically, it is 5 minutes to 48 hours.

Step 11

The step is a reaction of the compound 15 with the compound 10 (an alcohol compound $R^3OH$ or an amine compound $R^4R^5NH$) in an appropriate solvent to obtain the compound [I]. The step may be conducted as described in the above Step 6.

The pyrazolothiazole compound of the invention can be used as a medicine as it is, and also may be modified and used in a form of a pharmaceutically acceptable salt, a solvate or a solvate of salt by using a well-known method. Examples of the pharmaceutically acceptable salt may include, for example, a salt with a mineral acid such as hydrochlorate, hydrobromate, sulfate and phosphate, and a salt with an organic salt such as acetate, citrate, tartarate, maleate, succinate, fumarate, p-toluenesulfonate, benzenesulfonate and methanesulfonate.

The solvate includes a solvate with an organic solvent and a hydrate. Examples of the pharmaceutically acceptable solvate may include, for example, alcoholate (e.g., ethanolate) and hydrate. The hydrate may include for example, monohydrate and dihydrate. The solvate is formed by coordination with any type and number of solvents. The pharmaceutically acceptable salt may form a solvate.

For example, a hydrochloride salt of the compound can be obtained by dissolving the pyrazolothiazole compound of the invention in a solution of hydrogen chloride in alcohol, a solution of hydrogen chloride in ethyl acetate, a solution of hydrogen chloride in 1,4-dioxane or a solution of hydrogen chloride in diethyl ether.

Some of the compounds of the present invention may have an asymmetric carbon, and the respective stereo isomers and mixtures thereof are all included in the present invention. The stereo isomers can be prepared, for example, by means of optical resolution from the racemate thereof according to a known method using an optically active acid (e.g., tartaric acid, dibenzoyltartaric acid, mandelic acid and 10-camphor sulfonic acid, etc.), or by using an optically active compound prepared in advance as a starting material. In addition, the stereo isomers may be prepared by optical resolution using a chiral column or by asymmetric synthesis. Also, some of the compounds of the present invention may form tautomers, and the respective tautomers and mixtures thereof are also included in the invention.

The compound of the invention has JAK1 inhibitory activity as shown in the following test examples. Further, the compound of the invention also has anti-inflammatory, immunosuppressive and anti-proliferative effects etc., based on their JAK1 inhibitory activity.

Accordingly, the compound of the invention can be used as a preventive or therapeutic agent, for example, for the diseases associated with JAK1 and also the diseases for which the effect of the compound is expected in view of its anti-inflammatory, immunosuppressive and anti-proliferative effects etc.

Examples of specific diseases for which the compound of the invention can be applied include autoimmune disease (e.g., rheumatoid arthritis, psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (e.g., Takayasu's arteritis, giant cell arteritis, microscopic polyangiitis, granulomatosis with polyangiitis and eosinophilic granulomatosis with polyangiitis), dermatomyositis and polymyositis and neuromyelitis optica), inflammatory diseases (e.g., atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (e.g., solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection.

The compound of the invention may be administered as a medicament to mammals, including human, as it is or as a pharmaceutical composition containing the same in an amount of, for example, 0.001% to 99.5%, preferably 0.1% to 90%, in combination with one or more pharmaceutically acceptable nontoxic and inactive carrier(s).

As the carrier, one or more selected from solid, semi-solid, or liquid diluents, fillers, and other auxiliaries for pharmaceutical formulation may be used. The pharmaceutical composition according to the invention may be administered in a unit dosage form. The pharmaceutical composition may be administered by interstitial, oral, intravenous, topical (e.g., transdermal, instillation, intraperitoneal or intrathoracic administration) or transrectal administration. The composition should be administered in a dosage form suitable for these administration methods.

The dose of the compound should be adjusted taking into account the conditions of the patient, such as age, body weight, and the disease to be treated and the stage of the disease, the route of administration, and the compound to be administered, the type of salt in case where the compound is a salt, etc. In the case of oral administration to an adult, a typical daily dose of the compound of the invention or its pharmaceutically acceptable salt may be 0.01 mg to 5 g, and preferably 1 mg to 500 mg. In some cases, a lower dose may be sufficient, or conversely, a higher dose may be required. In general, the dose is given once a day or several times per day as divided portions, or in the case of intravenous administration, the medicine can be a bolus injection or continuously administered within 24 hours.

One or more of hydrogen, carbon and/or other atoms in the compound of the invention can be replaced with the respective isotope of hydrogen, carbon and/or other atoms. Examples of such isotopes include those of hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. A compound substituted with such isotope may be useful as a medicament, and all of such radiolabeled forms of the compound are included in the invention.

EXAMPLES

The invention is described in more detail with reference to the following Examples, Test Examples and Formulation Examples, which are not intended to limit the scope of the present invention.

The abbreviations used in the Examples are as follows.
DMF: dimethylformamide
DMSO: dimethyl sulfoxide
DIPEA: N,N-diisopropylethylamine
TEA: triethylamine
THF: tetrahydrofuran
TFA: trifluoroacetic acid
NMP: N-methylpyrrolidone
HATU: O-(7-azabenzotriazol-1-yl)-1,1,3,3-tetramethyluronium hexafluorophosphate
$CDCl_3$: deuterochloroform
DMSO-d6: hexadeuteroddimethyl sulfoxide
MS: mass spectrometry
LCMS: high-pressure liquid chromatograph mass spectrometry
ESI: electron spray ionization
M: molar concentration MS was determined by using LCMS. ESI method was used as the ionization method. The measurements of the mass spectrometry are shown as m/z.

The measurement condition for LCMS is as follows.
Analyzer: ACQUITY UPLC MS/PDA system (Waters)
Mass spectrometer: Waters 3100 MS detector
Photodiode array detector: ACQUITY PDA detector (UV Detection wavelength: 210 to 400 nm)

Column: Acquity BEH $C_{18}$, 1.7 µm, 2.1×50 mm
Flow rate: 0.5 mL/min
Column temperature: 40° C.
Solvent;
Solution A: 0.1% formic acid/$H_2O$ (v/v; the same hereinafter)
Solution B: 0.1% formic acid/acetonitrile The microwave experiment was done using Biotage Initiator 60™, which is able to achieve a temperature from 40 to 250° C. and a pressure up to 20 bar.

Reference Example 1

Pyrazolo[5,1-b][1,3]thiazole-7-carbonitrile

[Step 1] Preparation of 2-(thiazol-2-yl)acetonitrile

To a solution of tert-butyl cyanoacetate (28 g) in DMF (100 mL) was added 60% sodium hydride (7.9 g) in portions under ice cooling, and the resulting mixture was stirred for 10 min. To the mixture was added 2-bromothiazole (25 g), and the mixture was stirred at room temperature for 15 min, then at 120° C. for 2 h. To the reaction mixture was added 1 M aqueous solution of hydrochloric acid, and the aqueous layer was extracted with ethyl acetate. The organic layer was washed with water, dried over anhydrous magnesium sulfate, and concentrated under reduced pressure. The resulting residue was washed with hexane, the resulting solid was suspended in toluene (200 mL), to the suspension was added para-toluenesulfonic acid monohydrate (2.0 g), and the mixture was stirred at 105° C. for 2 h. The reaction solution was diluted with ethyl acetate, and the liquid separation was carried out by an addition of saturated aqueous sodium bicarbonate solution. The aqueous layer was further extracted with ethyl acetate, and the combined organic layer was dried over anhydrous magnesium sulfate, and concentrated under reduced pressure. The resulting residue was purified by silica gel column chromatography to give the title compound (7.0 g).
MS (m/z): 125 [M+H]$^+$

[Step 2] Preparation of pyrazolo[5,1-b][1,3]thiazole-7-carbonitrile

To a solution of 2-(thiazol-2-yl)acetonitrile obtained in Step 1 (5 g) in dichloromethane (50 mL) was added a solution of O-(mesitylsulfonyl)hydroxyamine (which can be prepared according to the method described in, for example, Organic Process Research & Development, 2009, 13, 263-267) in dichloromethane (20 mL) under ice cooling, and the mixture was stirred at room temperature for 2 h. Under ice cooling, to the reaction mixture was added diethyl ether, and the precipitated solid was collected on a filter. The resulting solid was suspended in triethyl orthoformate (35 mL), and the mixture was stirred at 120° C. for 1 h. The reaction solution was concentrated under reduced pressure, and the resulting residue was purified by silica gel column chromatography to give the title compound (2.5 g).
MS (m/z): 150 [M+H]$^+$ Reference Example 2

6-Hydroxy-2-(pyrazolo[5,1-b][1,3]thiazol-7-yl)pyrimidine-4-carboxylic acid

To a solution of pyrazolo[5,1-b][1,3]thiazole-7-carbonitrile obtained in Reference Example 1 (6 g) in methanol (150 mL) was added a solution of 28% sodium methoxide in methanol (24.6 mL), and the mixture was stirred at room temperature for 3 h. Then, ammonium chloride (12.9 g) was added thereto, and the mixture was stirred at 90° C. for 1 h. The reaction solution was concentrated under reduced pressure, to the resulting residue was added a solution of sodium diethyl oxalacetate (33.8 g) in 5 M aqueous sodium hydroxide solution (200 mL), and the mixture was stirred at 100° C. overnight. To the reaction mixture was added conc. hydrochloric acid to make the solution acidic, and the precipitated solid was collected on a filter. The resulting solid was dissolved in 5 M aqueous potassium hydroxide solution, and was washed with chloroform. To the aqueous layer was added conc. hydrochloric acid to make the solution acidic, and the precipitated solid was collected on a filter, and dried to obtain the title compound (10 g).
MS (m/z): 263 [M+H]$^+$ Reference Example 3

Methyl 6-chloro-2-(pyrazolo[5,1-b][1,3]thiazol-7-yl)pyrimidin-4-carboxylate

6-Hydroxy-2-(pyrazolo[5,1-b][1,3]thiazol-7-yl)pyrimidine-4-carboxylic acid obtained in Reference Example 2 (1.4 g) was suspended in phosphorus oxychloride (20 mL), to the suspension was added diethylaniline (1.6 g), and the mixture was stirred at 130° C. for 2 h. The reaction solution was concentrated under reduced pressure, to the reaction mixture was added methanol (100 mL) under ice cooling, and the resulting mixture was stirred at 10 min. The reaction solution was diluted with chloroform, separated by adding water, and the aqueous layer was further extracted with chloroform. The combined organic layer was dried over anhydrous magnesium sulfate, and concentrated under reduced pressure. The resulting residue was purified by silica gel column chromatography to give the title compound (910 mg).
MS (m/z): 297 [M+H]$^+$ Reference Example 4

6-Hydroxy-5-methyl-2-(pyrazolo[5,1-b][1,3]thiazol-7-yl)pyrimidine-4-carboxylic acid To a solution of pyrazolo[5,1-b][1,3]thiazole-7-carbonitrile obtained in Reference Example 1 (300 mg) in methanol (6 mL) was added a solution of 28% sodium methoxide in methanol (0.41 mL), and the mixture was stirred at room temperature for 1 h. Then, ammonium chloride (215 mg) was added thereto, and the mixture was stirred at 70° C. for 2 h. The reaction solution was concentrated under reduced pressure, the resulting residue was dissolved in 5 M aqueous sodium hydroxide solution (1.2 mL) and water (7 mL), methyloxalacetic acid diethyl ester (611 mg) was added to the solution, and the mixture was stirred at 90° C. for 45 min. To the reaction mixture was added conc. hydrochloric acid to make the solution acidic, and the precipitated solid was, collected on a filter, and dried to obtain the title compound (166 mg).
MS (m/z): 277 [M+H]$^+$ Reference Example 5

Methyl 6-chloro-5-methyl-2-(pyrazolo[5,1-b][1,3]thiazol-7-yl)pyrimidin-4-carboxylate Analogous to the method in Reference Example 3, the title compound was synthesized by using 6-hydroxy-5- methyl-2-(pyrazolo[5,1-b][1,3]thiazol-7-yl)pyrimidine-4-carboxylic acid obtained in Reference Example 4 in place of 6-hydroxy-2-(pyrazolo[5,1-b][1,3]thiazol-7-yl)pyrimidine-4-carboxylic acid.

MS (m/z): 311 [M+H]$^+$

Reference Example 6

(2S)-1-(Difluoromethoxy)propan-2-amine hydrochloride

[Step 1] Preparation of benzyl N-[(2S)-1-(difluoromethoxy)propan-2-yl]carbamate

Under argon atmosphere, to a solution of benzyl[(1S)-1-(hydroxymethyl)ethyl]carbamate (2 g) in acetonitrile (40 mL) were added 2,2-difluoro-2-(fluorosulfonyl)acetic acid (2.6 g) and copper iodide (364 mg), and the mixture was stirred at 50° C. for 1 h 30 min. The reaction solution was diluted with ethyl acetate, separated by adding saturated aqueous sodium bicarbonate solution, and the aqueous layer was further extracted with ethyl acetate. The combined organic layer was dried over anhydrous magnesium sulfate, and concentrated under reduced pressure. The resulting residue was purified by silica gel column chromatography to give the title compound (1.3 g).

$^1$H-NMR (CDCl$_3$) δ: 1.23 (3H, d), 3.75-3.90 (2H, m), 4.00 (1H, bs), 4.82 (1H, bs), 5.11 (2H, s), 6.22 (1H, t), 7.30-7.40 (5H, m)

[Step 2] Preparation of (2S)-1-(difluoromethoxy)propan-2-amine hydrochloride

To a solution of benzyl N-[(2S)-1-(difluoromethoxy)propan-2-yl]carbamate obtained in Step 1 (1.3 g) in ethanol (40 mL) was added 20% palladium hydroxide (on activated carbon, 300 mg), and medium pressure catalytic reduction was conducted. The reaction mixture was filtered to remove the palladium, then 4 M hydrogen chloride-ethyl acetate solution (2 mL) was added to the mother liquid, and the solvent was concentrated under reduced pressure to give the title compound (668 mg).

$^1$H-NMR (DMSO-d6) δ: 1.19 (3H, d), 3.40-3.50 (1H, m), 3.86 (1H, dd), 3.97 (1H, dd), 6.77 (1H, t), 8.06 (3H, bs)

Reference Example 7

(1S,2S)-2-(Difluoromethoxy)cyclopentanamine hydrochloride

[Step 1] Preparation of benzyl N-[(1S,2S)-2-hydroxycyclopentyl]carbamate

To a solution of (1S,2S)-2-benzyloxycyclopentanamine (5.0 g) in ethanol (40 mL) was added 20% palladium hydroxide (on activated carbon, 1.0 g), and medium pressure catalytic reduction was conducted. Palladium was filtered off, and the solvent was concentrated under reduced pressure. To the resulting residue were added water (100 mL) and sodium carbonate (7.0 g), then benzyl chloroformate (6.7 g) was added thereto under ice cooling, and the mixture was stirred at room temperature overnight. The reaction mixture was extracted with chloroform, and the organic layer was washed with saturated brine, dried over anhydrous magnesium sulfate, and concentrated under reduced pressure. The resulting residue was purified by silica gel column chromatography to give the title compound (5.9 g).

MS (m/z): 236 [M+H]$^+$

[Step 2] Preparation of benzyl N-[(1S,2S)-2-(difluoromethoxy)cyclopentyl]carbamate Analogous to the method in Reference Example 6 Step 1, the title compound was synthesized by using benzyl N-[(1S,2S)-2-hydroxycyclopentyl]carbamate obtained in Step 1 in place of benzyl[(1S)-1-(hydroxymethyl)ethyl]carbamate.

$^1$H-NMR (CDCl$_3$) δ: 1.40-1.50 (1H, m), 1.62-1.88 (3H, m), 1.91-2.05 (1H, m), 2.10-2.25 (1H, m), 3.95-4.00 (1H, m), 4.40 (1H, bs), 4.72 (1H, bs), 5.10 (2H, dd), 6.33 (1H, t), 7.30-7.41 (5H, m)

[Step 3] Preparation of (1S,2S)-2-(difluoromethoxy)cyclopentanamine hydrochloride Analogous to the method in Reference Example 6 Step 2, the title compound was synthesized by using benzyl N-[(1S,2S)-2-(difluoromethoxy)cyclopentyl]carbamate obtained in Step 2 in place of benzyl N-[(2S)-1-(difluoromethoxy)propan-2-yl]carbamate.

$^1$H-NMR (DMSO-d6) δ: 1.50-1.78 (4H, m), 2.01-2.10 (2H, m), 3.48 (1H, bs), 4.55 (1H, bs), 6.78 (1H, t), 8.28 (3H, bs)

Reference Example 8

{1-[(Difluoromethoxy)methyl]cyclopropyl}methanamine

To a solution of [1-(aminomethyl)cyclopropyl]methanol (720 mg) in dichloromethane (15 mL) was added DIPEA (2.5 mL), then benzyl chloroformate (1.46 g) was added thereto under ice cooling, and the mixture was stirred at room temperature overnight. The reaction solution was concentrated under reduced pressure, and the resulting residue was purified by silica gel column chromatography to give an oil (348 mg). To a solution of this oil (348 mg) in acetonitrile (10 mL) were added 2,2-difluoro-2-(fluorosulfonyl)acetic acid (395 mg) and copper iodide (56 mg), and the mixture was stirred at 50° C. for 1 h. The reaction solution was separated by adding saturated aqueous sodium bicarbonate solution, and the aqueous layer was further extracted with ethyl acetate. The combined organic layer was washed with saturated brine, dried over anhydrous magnesium sulfate, and concentrated under reduced pressure. The resulting residue was purified by silica gel column chromatography to give an oil (129 mg). To a solution of the oil (129 mg) in methanol (8.0 mL) was added 20% palladium hydroxide (on activated carbon, 43 mg), and medium pressure catalytic reduction was conducted. The reaction solution was filtered to remove the palladium, and the mother liquid was concentrated under reduced pressure to give the title compound (68 mg).

$^1$H-NMR (CDCl$_3$) δ: 0.51-0.52 (4H, m), 2.69 (2H, s), 3.79 (2H, s), 6.25 (1H, t)

Reference Example 9

{1-[(Difluoromethoxy)methyl]cyclobutyl}methanamine

Analogous to the method in Reference Example 8, the title compound was synthesized by using [1-(aminomethyl)

cyclobutyl]methanol (which is prepared according to the method described in, for example, Journal of Medicinal Chemistry, 1972, 15, 1003-1006) in place of [1-(aminomethyl)cyclopropyl]methanol.

$^1$H-NMR (CDCl$_3$) δ: 1.78-1.91 (6H, m), 2.78 (2H, s), 3.86 (2H, s), 6.23 (1H, t)

Reference Example 10

{1-[(Difluoromethoxy)methyl]cyclopentyl}methanamine

Analogous to the method in Reference Example 8, the title compound was synthesized by using [1-(aminomethyl)cyclopentyl]methanol (which is prepared according to the method described in, for example, Journal of Medicinal Chemistry, 1972, 15, 1003-1006) in place of [1-(aminomethyl)cyclopropyl]methanol.

1H-NMR (CDCl$_3$) δ: 1.42-1.46 (4H, m), 1.58-1.64 (4H, m), 2.69 (2H, s), 3.72 (2H, s), 6.24 (1H, t)

Reference Example 11

{4-[(Difluoromethoxy)methyl]tetrahydro-2H-pyran-4-yl}methanamine

To a solution of ethyl 4-{[(tert-butoxycarbonyl)amino]methyl}tetrahydro-2H-pyran-4-carboxylate (1.3 g) in dichloromethane (10 mL) was added TFA (5.0 mL), and the mixture was stirred at room temperature for 4 h. The reaction solution was concentrated under reduced pressure, to a solution of the resulting residue in dichloromethane (10 mL) was added DIPEA (3.1 mL), then benzyl chloroformate (1.1 g) was added thereto under ice cooling, and the mixture was stirred at room temperature overnight. The reaction solution was concentrated under reduced pressure, and the resulting residue was purified by silica gel column chromatography to give an oil (1.4 g). To a solution of the oil (1.3 g) in ethanol (20 mL) was added sodium borohydride (382 mg) under ice cooling, and the mixture was stirred at room temperature for 2.5 days. Then, sodium borohydride (382 mg) was added thereto, the mixture was stirred at room temperature for 4 h, then at 50° C. for 3 h, and further at room temperature overnight. To the reaction solution was added water under ice water cooling, and the solution was extracted with ethyl acetate. The organic layer was washed with saturated brine, dried over anhydrous magnesium sulfate, and concentrated under reduced pressure. The resulting residue was purified by silica gel column chromatography to give an oil (484 mg). To a solution of the oil (484 mg) in acetonitrile (10 mL) were added 2,2-difluoro-2-(fluorosulfonyl)acetic acid (463 mg) and copper iodide (66 mg), and the mixture was stirred at 50° C. for 1 h. To the reaction solution was added saturated aqueous sodium bicarbonate solution, and the mixture was extracted with ethyl acetate. The organic layer was washed with saturated brine, dried over anhydrous magnesium sulfate, and concentrated under reduced pressure. The resulting residue was purified by silica gel column chromatography to give an oil (209 mg). To a solution of the oil (200 mg) in methanol (8.0 mL) was added 20% palladium hydroxide (on activated carbon, 80 mg), and medium pressure catalytic reduction was conducted. The reaction mixture was filtered to remove the palladium, and the mother liquid was concentrated under reduced pressure to give the title compound (108 mg).

$^1$H-NMR (CDCl$_3$) δ: 1.50-1.53 (4H, m), 2.76 (2H, s), 3.64-3.71 (4H, m), 3.84 (2H, s), 6.24 (1H, t)

Reference Example 12

(2R)—N,3,3-Trimethylbutan-2-amine hydrochloride

To a solution of (2R)-3,3-dimethylbutan-2-amine (5.0 g) in dichloromethane (100 ml) was added TEA (15 ml), benzyl chloroformate (9.3 g) was added dropwise thereto under ice cooling, and the mixture was stirred overnight. The reaction mixture was diluted with chloroform, the solution was separated by adding saturated aqueous sodium bicarbonate solution, the aqueous layer was further extracted with chloroform, and the combined organic layer was washed with saturated aqueous sodium bicarbonate solution, dried over anhydrous sodium sulfate, and concentrated under reduced pressure. The resulting residue was purified by silica gel column chromatography to give the crude product (4.0 g). To a solution of the obtained crude product (4.0 g) in DMF (15 ml) was added iodomethane (4.8 g), and 60% sodium hydride (748 mg) was added thereto under ice cooling. After the mixture was stirred at room temperature for 1 h, ice water was added thereto and the reaction solution was extracted with ethyl acetate. The organic layer was washed with saturated aqueous sodium bicarbonate solution, dried over anhydrous magnesium sulfate, and concentrated under reduced pressure. The resulting residue was purified by silica gel column chromatography to give the crude product (4.2 g). To a solution of the obtained crude product (4.2 g) in ethanol (20 mL) was added 20% palladium hydroxide (on activated carbon, 1.0 g), and medium pressure catalytic reduction was conducted. The reaction mixture was filtered to remove the palladium, 2 M hydrogen chloride-ethanol solution (9.0 ml) was added to the mother liquid, and the solvent was concentrated under the reduced pressure to give the title compound (2.0 g).

MS (m/z): 116 [M−Cl]$^+$

Reference Example 13

1-[1-(Methoxymethyl)cyclopropyl]-N-methylmethanamine hydrochloride

[Step 1] Preparation of benzyl {[1-(hydroxymethyl)cyclopropyl]methyl}carbamate

To a solution of [1-(aminomethyl)cyclopropyl]methanol (1.5 g) (which was prepared analogous to the method described in, for example, Journal of Medicinal Chemistry, 1972, 15, 1003-1006) in dichloromethane (30 mL) was added DIPEA (3.7 g), benzyl chloroformate (3.5 g) was added thereto under ice cooling, and the mixture was stirred at room temperature overnight. The reaction solution was concentrated under reduced pressure, and the resulting residue was purified by silica gel column chromatography to give the title compound (3.0 g).

$^1$H-NMR (CDCl$_3$) δ: 0.46 (4H, s), 2.78 (1H, t), 3.20 (2H, d), 3.40 (2H, d), 5.12 (2H, s), 5.23 (1H, s), 7.35-7.37 (5H, m)

[Step 2] Preparation of benzyl {[1-(methoxymethyl)cyclopropyl]methyl}methylcarbamate To a solution of benzyl(([1-(hydroxymethyl)cyclopropyl]methyl carbamate obtained in Step 1 (350 mg) in DMF (3.0 mL) were added iodomethane (1.0 g) and silver oxide (1.7 g), and the mixture was stirred at room temperature overnight. Under ice cooling, to the reaction mixture was added saturated aqueous ammonium chloride solution, and the mixture was extracted with diethyl ether. The organic layer was dried over anhydrous magnesium sulfate, and concentrated under reduced pressure. The resulting residue was purified by silica gel column chromatography to give the title compound (189 mg).

$^1$H-NMR (CDCl$_3$) δ: 0.46-0.60 (4H, m), 2.99 (3H, s), 3.15-3.36 (7H, m), 5.13 (2H, s), 7.28-7.39 (5H, m)

[Step 3] Preparation of 1-[1-(methoxymethyl)cyclopropyl]-N-methylmethanamine hydrochloride To a solution of benzyl{[1-(methoxymethyl)cyclopropyl]methyl}methylcarbamate obtained in Step 2 (165 mg) in ethanol (6.0 mL) was added palladium hydroxide (on activated carbon, 80 mg), and medium pressure catalytic reduction was conducted. The reaction mixture was filtered to remove the palladium, 2 M hydrogen chloride-ethanol solution (27 µL) was added to the mother liquid, and the solvent was concentrated under reduced pressure to give the title compound (95 mg).

$^1$H-NMR (DMSO-d6) δ: 0.53 (2H, t), 0.66 (2H, t), 2.51 (3H, s), 2.88 (2H, s), 3.26 (3H, s), 3.27 (2H, s), 8.52 (2H, br)

Reference Example 14

Methyl(1-{[6-chloro-2-(pyrazolo[5,1-b][1,3]thiazol-7-yl)pyrimidin-4-yl]carbonyl}piperidin-4-yl)carbamate

[Step 1] Preparation of methyl piperidin-4-ylcarbamate

To a solution of 1-benzylpiperidin-4-amine (5.0 g) in dichloromethane (100 mL) was added TEA (9.2 mL), methyl chloroformate (2.6 g) was added dropwise thereto under ice cooling, and the mixture was stirred for 1 h. The reaction solution was diluted with chloroform, separated by adding water, and the aqueous layer was further extracted with chloroform. The combined organic layer was dried over anhydrous magnesium sulfate, and then, concentrated under reduced pressure to give an oil (3.4 g). To a solution of the resulting oil (3.4 g) in ethanol (50 mL) was added 20% palladium hydroxide (on activated carbon, 1 g), and medium pressure catalytic reduction was conducted. The reaction mixture was filtered to remove the palladium, and the mother liquid was concentrated under reduced pressure to give the title compound (1.9 g).

MS (m/z): 159 [M+H]$^+$

[Step 2] Preparation of methyl(1-{[6-chloro-2-(pyrazolo[5,1-b][1,3]thiazol-7-yl)pyrimidin-4-yl]carbonyl}piperidin-4-yl)carbamate 6-Hydroxy-2-(pyrazolo[5,1-b][1,3]thiazol-7-yl)pyrimidine-4-carboxylic acid obtained in Reference Example 2 (700 mg) was suspended in phosphorus oxychloride (5.0 mL), diethylaniline (0.4 g) was added to the suspension, and the mixture was stirred at 110° C. for 2 h. The reaction solution was concentrated under reduced pressure, and dissolved in dichloromethane (40 mL) under ice cooling. To the resulting solution were added DIPEA (2.3 mL) and methyl piperidin-4-ylcarbamate obtained in Step 1 (443 mg), and the mixture was stirred at room temperature for 30 min. The reaction solution was diluted with chloroform, separated by adding saturated aqueous sodium bicarbonate solution, and the aqueous layer was further extracted with chloroform. The combined organic layer was dried over anhydrous magnesium sulfate, and concentrated under reduced pressure. The resulting residue was purified by silica gel column chromatography to give the title compound (570 mg).

MS (m/z): 421, 423 [M+H]$^+$

Reference Example 15

N-(1-{[6-Chloro-2-(pyrazolo[5,1-b][1,3]thiazol-7-yl)pyrimidin-4-yl]carbonyl}piperidin-4-yl)cyclopropanecarboxamide Analogous to the method in Reference Example 14 Step 2, the title compound was synthesized by using N-(piperidin-4-yl)cyclopropanecarboxamide (which was prepared analogous to the method described in, for example, Journal of Medicinal Chemistry, 2010, 53, 6386-6397) in place of methyl piperidin-4-ylcarbamate.

MS (m/z): 431, 433 [M+H]$^+$

Reference Example 16

N-(1-{[6-Chloro-2-(pyrazolo[5,1-b][1,3]thiazol-7-yl)pyrimidin-4-yl]carbonyl}piperidin-4-yl)-2-methylpropanamide Analogous to the method in Reference Example 14 Step 2, the title compound was synthesized by using 2-methyl-N-(4-piperidyl)propanamide (which was prepared analogous to the method described in, for example, Bioorganic & Medicinal Chemistry Letters, 2012, 22, 3157-3162) in place of methyl piperidin-4-ylcarbamate.

MS (m/z): 433, 435 [M+H]$^+$

Reference Example 17 tert-Butyl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using tert-butyl N-(4-piperidyl)carbamate in place of methyl piperidin-4-ylcarbamate.

MS (m/z): 463, 465 [M+H]$^+$

Reference Example 18

[6-Chloro-2-(pyrazolo[5,1-b][1,3]thiazol-7-yl)pyrimidin-4-yl][4-(pyridin-2-ylamino)piperidin-1-yl]methanone Under argon atmosphere, to a solution of 1-benzylpiperidin-4-amine (980 mg) and 2-fluoropyridine (500 mg) in THF (3.0 mL) was added 1 M lithium bis(trimethylsilyl)amide (THF solution, 10.3 mL) at −78° C. The mixture was stirred at room temperature for 1 h, then at 70° C. overnight. The reaction mixture was diluted with chloroform, separated by adding saturated aqueous sodium bicarbonate solution, and the aqueous layer was further extracted with chloroform. The combined organic layer was dried over anhydrous magnesium sulfate, and concentrated under reduced pressure. The resulting residue was purified by silica gel column chromatography to give an oil (155 mg). To a solution of the resulting oil (150 mg) in ethanol (10 mL) were added 20% palladium hydroxide (on activated carbon, 50 mg) and TFA (1 drop), and medium pressure catalytic reduction was conducted at 40° C. The reaction mixture was filtered to remove the palladium, and the mother liquid was concentrated under reduced pressure to give a solid (110 mg). 6-Hydroxy-2-(pyrazolo[5,1-b][1,3]thiazol-7-yl)pyrimidine-4-carboxylic acid obtained in Reference Example 2 (150 mg) was suspended in phosphorus oxychloride (1.1 mL), diethylaniline (85 mg) was added to the suspension, and the mixture was stirred at 110° C. for 2 h. The reaction solution was concentrated under reduced pressure, and the resulting residue was dissolved in dichloromethane (10 mL) under ice cooling, DIPEA (0.5 mL) and the above solid (101 mg) were added to the solution, and the mixture was stirred at room temperature for 30 min. The reaction solution was diluted with chloroform, separated by adding saturated aqueous sodium bicarbonate solution, and the aqueous layer was further extracted with chloroform. The combined organic layers were dried over anhydrous magnesium sulfate, and concentrated under reduced pressure. The resulting residue was purified by silica gel column chromatography to give the title compound (36 mg).

MS (m/z): 400, 402 [M+H]$^+$

Reference Example 19

[6-Chloro-2-(pyrazolo[5,1-b][1,3]thiazol-7-yl)pyrimidin-4-yl][4-(1,3-thiazol-2-ylamino)piperidin-1-yl]methanone Under argon atmosphere, to a solution of tert-butyl N-thiazol-2-ylcarbamate (1.9 g) and tert-butyl 4-hydroxypiperidine-1-carboxylate (1.8 g) in THF (20 mL) was added diethyl azodicarboxylate (2.2 M toluene solution, 5.1 mL) under ice cooling, and the mixture was stirred at room temperature for 16 h. The solvent was distilled off, and the resulting residue was purified by silica gel column chromatography to give a solid 1 (2.2 g). To a solution of the obtained solid 1 (2.2 g) in dichloromethane (5 mL) was added TFA (5 mL), and the mixture was stirred at room temperature for 1 h 30 min. The reaction solution was concentrated under reduced pressure, and the resulting residue was purified by silica gel column chromatography to give a solid 2 (796 mg). 6-Hydroxy-2-(pyrazolo[5,1-b][1,3]thiazol-7-yl)pyrimidine-4-carboxylic acid obtained in Reference Example 2 (100 mg) was suspended in phosphorus oxychloride (1.1 mL), diethylaniline (57 mg) was added to the suspension, and the mixture was stirred at 110° C. for 2 h. The reaction solution was concentrated under reduced pressure, the concentrate was dissolved in dichloromethane (10 mL) under ice cooling, DIPEA (0.33 mL) and the solid 2 (136 mg) were added to the solution, and the mixture was stirred at room temperature for 30 min. The reaction solution was diluted with chloroform, separated by adding saturated aqueous sodium bicarbonate solution, and the aqueous layer was further extracted with chloroform. The combined organic layers were dried over anhydrous magnesium sulfate, and concentrated under reduced pressure. The resulting residue was purified by silica gel column chromatography to give the title compound (70 mg).

MS (m/z): 446, 448 [M+H]$^+$

Reference Example 20

[6-Chloro-2-(pyrazolo[5,1-b][1,3]thiazol-7-yl)pyrimidin-4-yl][4-(pyrimidin-2-ylamino)piperidin-1-yl]methanone To a solution of tert-butyl 4-(pyrimidin-2-ylamino)piperidine-1-carboxylate (251 mg) in dichloromethane (3.0 mL) was added TFA (1.0 mL), and the mixture was stirred at room temperature for 30 min. The solvent was concentrated under reduced pressure, and the resulting residue was purified by silica gel column chromatography to give a solid (248 mg). 6-Hydroxy-2-(pyrazolo[5,1-b][1,3]thiazol-7-yl)pyrimidine-4-carboxylic acid obtained in Reference Example 2 (100 mg) was suspended in phosphorus oxychloride (1.1 mL), diethylaniline (57 mg) was added to the suspension, and the mixture was stirred at 110° C. for 1 h. The reaction solution was concentrated under reduced pressure, the resulting residue was dissolved in dichloromethane (10 mL) under ice cooling, DIPEA (0.33 mL) and the solid (134 mg) were added to the solution, and the mixture was stirred at room temperature for 30 min. The reaction solution was diluted with chloroform, separated by adding saturated aqueous sodium bicarbonate solution, and the aqueous layer was further extracted with chloroform. The combined organic layer was dried over anhydrous magnesium sulfate, and concentrated under reduced pressure. The resulting residue was purified by silica gel column chromatography to give the title compound (104 mg).

MS (m/z): 441, 443 [M+H]$^+$

Reference Example 21

Cyclopropyl(1-{[6-chloro-2-(pyrazolo[5,1-b][1,3]thiazol-7-yl)pyrimidin-4-yl]carbonyl}piperidin-4-yl)carbamate

[Step 1] Preparation of benzyl 4-(cyclopropanecarbonylamino)piperidine-1-carboxylate To a solution of 1-benzyloxycarbonylpiperidin-4-carboxylic acid (400 mg) in toluene (3 mL) were added TEA (0.85 mL) and diphenylphosphoryl azide (627 mg), and the mixture was stirred at 90° C. for 3 h. Then, cyclopropanol (132 mg) (which was prepared analogous to the method described in, for example, US 2012/0010183) was added thereto, and the mixture was stirred at 80° C. overnight. The reaction mixture was diluted with ethyl acetate, separated by adding saturated aqueous sodium bicarbonate solution, and the aqueous layer was further extracted with ethyl acetate. The combined organic layer was dried over anhydrous magnesium sulfate, and concentrated under reduced pressure. The resulting residue was purified by silica gel column chromatography to give the title compound (190 mg).

MS (m/z): 319 [M+H]$^+$

[Step 2] Preparation of cyclopropyl piperidin-4-ylcarbamate

To a solution of benzyl 4-(cyclopropanecarbonylamino)piperidine-1-carboxylate obtained in Step 1 (190 mg) in ethanol (10 mL) was added 20% palladium hydroxide (on activated carbon, 50 mg), and medium pressure catalytic reduction was conducted. The reaction solution was filtered to remove the palladium, and the mother liquid was concentrated under reduced pressure to give the title compound (110 mg).

MS (m/z): 185 [M+H]$^+$

[Step 3] Preparation of cyclopropyl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using cyclopropyl piperidin-4-ylcarbamate obtained in Reference Example 21 Step 2 in place of methyl piperidin-4-ylcarbamate.
MS (m/z): 447, 449 [M+H]⁺

Reference Example 22

Propan-2-yl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using propan-2-yl piperidin-4-ylcarbamate (which was prepared analogous to the method described in, for example, U.S. Pat. No. 5,082,847) in place of methyl piperidin-4-ylcarbamate.
MS (m/z): 449, 451 [M+H]⁺

Reference Example 23

Propyl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using propyl piperidin-4-ylcarbamate (which was prepared analogous to the method described in, for example, U.S. Pat. No. 5,082,847) in place of methyl piperidin-4-ylcarbamate.
MS (m/z): 449, 451 [M+H]⁺

Reference Example 24

2-Methoxyethyl(1-{[6-chloro-2-(pyrazolo[5,1-b][1,3]thiazol-7-yl)pyrimidin-4-yl]carbonyl}piperidin-4-yl)carbamate

[Step 1] Preparation of 2-methoxyethyl piperidin-4-ylcarbamate

To a solution of 1-benzyloxycarbonylpiperidin-4-carboxylic acid (300 mg) in toluene (2 mL) were added TEA (556 μL), diphenylphosphoryl azide (320 μL) and 2-methoxyethanol (2 mL), and the mixture was stirred at 100° C. for 4 h. The reaction solution was concentrated under reduced pressure, and the resulting residue was purified by silica gel column chromatography to give an oil (189 mg). To a solution of the resulting oil (189 mg) in methanol (10 mL) was added 5% palladium (on activated carbon, 30 mg), and medium pressure catalytic reduction was conducted. The reaction solution was filtered to remove the palladium, and the mother liquid was concentrated under reduced pressure to give the title compound (111 mg).
$^1$H-NMR (CDCl$_3$) δ: 1.32-1.37 (2H, m), 1.94-1.97 (2H, m), 2.60-2.74 (2H, t), 3.08 (2H, d), 3.40 (3H, s), 3.57-3.59 (3H, m), 4.20-4.22 (2H, m), 4.75-4.77 (1H, m)

[Step 2] Preparation of 2-methoxyethyl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using 2-methoxyethyl piperidin-4-ylcarbamate obtained in Step 1 in place of methyl piperidin-4-ylcarbamate.
MS (m/z): 465, 467 [M+H]⁺

Reference Example 25

2,2-Difluoroethyl(1-{[6-chloro-2-(pyrazolo[5,1-b][1,3]thiazol-7-yl)pyrimidin-4-yl]carbonyl}piperidin-4-yl)carbamate

[Step 1] Preparation of 2,2-difluoroethyl piperidin-4-ylcarbamate

To a solution of 2,2-difluoroethanol (100 mg) in dichloromethane (1.0 mL) were added TEA (255 μL) and triphosgene (145 mg) under ice cooling. After the mixture was stirred for 30 min, 4-amino-1-benzylpiperidine (497 μL) was added thereto and the mixture was further stirred for 30 min. To the reaction solution was added saturated aqueous sodium bicarbonate solution, and the solution was extracted with ethyl acetate. The organic layer was dried over anhydrous magnesium sulfate, and concentrated under reduced pressure. The resulting residue was purified by silica gel column chromatography to give an oil (185 mg). To a solution of the resulting oil (185 mg) in methanol (10 mL) was added 5% palladium (on activated carbon, 30 mg), and medium pressure catalytic reduction was conducted. The reaction solution was filtered to remove the palladium, and the mother liquid was concentrated under reduced pressure to give the title compound (123 mg).
$^1$H-NMR (CDCl$_3$) δ: 1.25-1.34 (2H, m), 1.94-1.97 (2H, m), 2.60-2.71 (2H, m), 3.04-3.08 (2H, m), 3.55-3.68 (1H, m), 4.20-4.35 (2H, m), 4.77 (1H, br), 5.78-6.08 (1H, m)

[Step 2] Preparation of 2,2-difluoroethyl(1-{[6-chloro-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using 2,2-difluoroethyl piperidin-4-ylcarbamate obtained in Step 1 in place of methyl piperidin-4-ylcarbamate.
MS (m/z): 471, 473 [M+H]⁺

Reference Example 26

2,2,2-Trifluoroethyl(1-{[6-chloro-2-(pyrazolo[5,1-b][1,3]thiazol-7-yl)pyrimidin-4-yl]carbonyl}piperidin-4-yl)carbamate Analogous to the method in Reference Example 25, the title compound was synthesized by using 2,2,2-trifluoroethanol in place of 2,2-difluoroethanol.
MS (m/z): 489, 491 [M+H]⁺

Reference Example 27

N-(1-{[6-Chloro-2-(pyrazolo[5,1-b][1,3]thiazol-7-yl)pyrimidin-4-yl]carbonyl}piperidin-4-yl)-2-methoxyacetamide

[Step 1] Preparation of 2-methoxy-N-(4-piperidyl)acetamide

To a solution of 1-benzylpiperidin-4-amine (10 g) and TEA (15.9 mL) in dichloromethane (200 mL) was added methoxyacetyl chloride (6.3 g) dropwise under ice cooling, and the mixture was stirred for 3 h. To the reaction solution was added saturated aqueous sodium bicarbonate solution, and the solution was extracted with ethyl acetate. The combined organic layer was dried over anhydrous sodium sulfate, and concentrated under reduced pressure to give an oil. The resulting oil was purified by silica gel column chromatography to give an oil (13.8 g). To a solution of the resulting oil in ethanol (100 mL) was added 20% palladium hydroxide (on activated carbon, 1.0 g), and medium pressure catalytic reduction was conducted. The reaction mixture was filtered to remove the palladium, and the mother liquid was concentrated under reduced pressure to give the title compound (8.0 g).

MS (m/z): 173 [M+H]$^+$

[Step 2] Preparation of N-(1-{[6-chloro-2-(pyrazolo[5,1-b][1,3]thiazol-7-yl)pyrimidin-4-yl]carbonyl}piperidin-4-yl)-2-methoxyacetamide Analogous to the method in Reference Example 14 Step 2, the title compound was synthesized by using 2-methoxy-N-(4-piperidyl)acetamide obtained in Step 1 in place of methyl piperidin-4-ylcarbamate.

MS (m/z): 435, 437 [M+H]$^+$

Reference Example 28

N-(1-{[6-Chloro-2-(pyrazolo[5,1-b][1,3]thiazol-7-yl)pyrimidin-4-yl]carbonyl}piperidin-4-yl)-2,2-difluoroacetamide

[Step 1] Preparation of 2,2-difluoro-N-(4-piperidyl)acetamide

To a solution of difluoroacetic acid (2.3 g) in dichloromethane (100 mL) was added DMF (0.1 mL), oxalyl chloride (2.6 g) was added dropwise thereto under ice cooling, and the mixture was stirred for 1 h. Then, 1-benzylpiperidin-4-amine (3.0 g) was added thereto, TEA (6.1 g) was added dropwise to the mixture under ice cooling, and the mixture was stirred at room temperature for 1 h. To the reaction solution was added saturated aqueous sodium bicarbonate solution, and the solution was extracted with ethyl acetate. The organic layer was dried over anhydrous sodium sulfate, and concentrated under reduced pressure. The resulting residue was purified by silica gel column chromatography to give an oil (500 mg). To a solution of the resulting oil in ethanol (5.0 mL) was added 20% palladium hydroxide (on activated carbon, 300 mg), and medium pressure catalytic reduction was conducted. The reaction mixture was filtered to remove the palladium, and the mother liquid was concentrated under reduced pressure to give the title compound (200 mg).

MS (m/z): 179 [M+H]$^+$

[Step 2] Preparation of N-(1-{[6-chloro-2-(pyrazolo[5,1-b][1,3]thiazol-7-yl)pyrimidin-4-yl]carbonyl}piperidin-4-yl)-2,2-difluoroacetamide Analogous to the method in Reference Example 14 Step 2, the title compound was synthesized by using 2,2-difluoro-N-(4-piperidyl)acetamide obtained in Step 1 in place of methyl piperidin-4-ylcarbamate.

$^1$H-NMR (CDCl$_3$) δ: 1.55-1.65 (4H, m), 2.04-2.15 (2H, m), 3.03-3.06 (1H, m), 3.28-3.30 (1H, m), 4.72-4.75 (1H, m) 5.91 (1H, t), 6.22-6.24 (1H, m) 7.09 (1H, d), 7.30 (1H, s), 7.90 (1H, d), 8.50 (1H, s)

Reference Example 29

[6-chloro-2-(pyrazolo[5,1-b][1,3]thiazol-7-yl)pyrimidin-4-yl](4-hydroxypiperidin-1-yl)methanone Analogous to the method in Reference Example 14 Step 2, the title compound was synthesized by using piperidin-4-ol in place of methyl piperidin-4-ylcarbamate.

MS (m/z): 364, 366 [M+H]$^+$

Reference Example 30

(4-{[tert-Butyl(dimethyl)silyl]oxy}piperidin-1-yl)[6-chloro-2-(pyrazolo[5,1-b][1,3]thiazol-7-yl)pyrimidin-4-yl]methanone Analogous to the method in Reference Example 14 Step 2, the title compound was synthesized by using 4-{[tert-butyl(dimethyl)silyl]oxy}piperidine (which was prepared analogous to the method described in, for example, WO 2004/006926) in place of methyl piperidin-4-ylcarbamate.

$^1$H-NMR (CDCl$_3$) δ: 0.07 (6H, d), 0.91 (9H, s), 1.56-1.75 (2H, m), 1.79-1.91 (2H, m), 3.40-3.50 (1H, m) 3.63-3.92 (3H, m), 4.02-4.11 (1H, m) 7.07 (1H, d), 7.26 (1H, s), 7.88 (1H, d), 8.51 (1H, s)

Reference Example 31

N-(1-{[6-Chloro-2-(pyrazolo[5,1-b][1,3]thiazol-7-yl)pyrimidin-4-yl]carbonyl}piperidin-4-yl)propanamide Analogous to the method in Reference Example 14 Step 2, the title compound was synthesized by using N-(4-piperidyl)propanamide (which was prepared analogous to the method described in, for example, Bioorganic & Medicinal Chemistry Letters, 2003, 13, 2303-2306) in place of methyl piperidin-4-ylcarbamate.

MS (m/z): 419, 421 [M+H]$^+$

Reference Example 32

[6-Chloro-2-(pyrazolo[5,1-b][1,3]thiazol-7-yl)pyrimidin-4-yl]{4-[(3-fluoropyridin-2-yl)amino]piperidin-1-yl}methanone

[Step 1] Preparation of N-(1-benzylpiperidin-4-yl)-3-fluoropyridin-2-amine

To a solution of 1-benzylpiperidin-4-amine (100 mg) in DMSO (2.0 mL) were added 2,3-difluoropyridine (25 μL) and DIPEA (95 μL), and the mixture was stirred by using a microwave reactor at 130° C. for 2 h. The reaction solution was diluted with ethyl acetate, separated by adding water, and the aqueous layer was further extracted with ethyl acetate. The combined organic layer was dried over anhydrous magnesium sulfate, and concentrated under reduced pressure. The resulting residue was purified by silica gel column chromatography to give the title compound (74 mg).

MS (m/z): 286 [M+H]$^+$

[Step 2] Preparation of 3-fluoro-N-(piperidin-4-yl)pyridin-2-amine

To a solution of N-(1-benzylpiperidin-4-yl)-3-fluoropyridin-2-amine obtained in Step 1 (970 mg) in ethanol (15 mL) were added 20% palladium hydroxide (on activated carbon, 300 mg) and a catalytic amount of TFA, and medium pressure catalytic reduction was conducted. The reaction solution was filtered to remove the palladium, and the mother liquid was concentrated under reduced pressure to give the title compound (770 mg).
MS (m/z): 196 [M|H]$^+$

[Step 3] Preparation of [6-chloro-2-(pyrazolo[5,1-b][1,3]thiazol-7-yl)pyrimidin-4-yl]{4-[(3-fluoropyridin-2-yl)amino]piperidin-1-yl}methanone Analogous to the method in Reference Example 14 Step 2, the title compound was synthesized by using 3-fluoro-N-(piperidin-4-yl)pyridin-2-amine obtained in Step 2 in place of methyl piperidin-4-ylcarbamate.
MS (m/z): 458, 460 [M+H]$^+$ Reference Example 33

3-(1-{[6-Chloro-2-(pyrazolo[5,1-b][1,3]thiazol-7-yl)pyrimidin-4-yl]carbonyl}piperidin-4-yl)-1,1-dimethylurea

[Step 1]Preparation of 3-(1-benzylpiperidin-4-yl)-1,1-dimethylurea

To a solution of 1-benzylpiperidin-4-amine (2.0 g) in dichloromethane (50 mL) was added TEA (4.4 mL), then, under ice cooling, N,N-dimethylcarbamoyl chloride (1.2 mL) was slowly added dropwise thereto, and the mixture was stirred at room temperature overnight. To the reaction mixture was added water, and the solution was extracted with chloroform. The organic layer was dried over anhydrous magnesium sulfate, and concentrated under reduced pressure to give the title compound (2.7 g).
$^1$H-NMR (CDCl$_3$) δ: 1.43 (2H, q), 1.94 (2H, d), 2.13 (2H, t), 2.80 (2H, d), 2.88 (6H, s), 3.50 (2H, s), 3.67 (1H, m), 4.17 (1H, d), 7.22-7.32 (5H, m)

[Step 2] Preparation of 1,1-dimethyl-3-piperidin-4-ylurea

Analogous to the method in Reference Example 21 Step 2, the title compound was synthesized by using 3-(1-benzylpiperidin-4-yl)-1,1-dimethylurea obtained in Step 1 in place of benzyl 4-(cyclopropanecarbonylamino)piperidine-1-carboxylate.
MS (m/z): 172 [M+H]$^+$

[Step 3] Preparation of 3-(1-{[6-chloro-2-(pyrazolo[5,1-b][1,3]thiazol-7-yl)pyrimidin-4-yl]carbonyl}piperidin-4-yl)-1,1-dimethylurea Analogous to the method in Reference Example 14 Step 2, the title compound was synthesized by using 1,1-dimethyl-3-piperidin-4-ylurea obtained in Step 2 in place of methyl piperidin-4-ylcarbamate.
MS (m/z): 434, 436 [M+H]$^+$ Reference Example 34

[6-Chloro-2-(pyrazolo[5,1-b][1,3]thiazol-7-yl)pyrimidin-4-yl]{4-[(5-fluoropyridin-2-yl)amino]piperidin-1-yl}methanone

[Step 1] Preparation of N-(1-benzylpiperidin-4-yl)-5-fluoropyridin-2-amine

Analogous to the method in Reference Example 32 Step 1, the title compound was synthesized by using 2,5-difluoropyridine in place of 2,3-difluoropyridine.
MS (m/z): 286 [M+H]$^+$

[Step 2] Preparation of 5-fluoro-N-(piperidin-4-yl)pyridin-2-amine

Analogous to the method in Reference Example 32 Step 2, the title compound was synthesized by using N-(1-benzylpiperidin-4-yl)-5-fluoropyridin-2-amine obtained in Step 1 in place of N-(1-benzylpiperidin-4-yl)-3-fluoropyridin-2-amine.
$^1$H-NMR (CDCl$_3$) δ: 1.75 (2H, d), 2.24 (2H, d), 2.99 (2H, t), 3.40 (2H, d), 3.97 (1H, s), 4.28 (2H, d), 6.36 (1H, d), 7.19 (1H, t), 7.93 (1H, d)

[Step 3] Preparation of [6-chloro-2-(pyrazolo[5,1-b][1,3]thiazol-7-yl)pyrimidin-4-yl]{4-[(5-fluoropyridin-2-yl)amino]piperidin-1-yl}methanone Analogous to the method in Reference Example 14 Step 2, the title compound was synthesized by using 5-fluoro-N-(piperidin-4-yl)pyridin-2-amine obtained in Step 2 in place of methyl piperidin-4-ylcarbamate.
MS (m/z): 458, 460 [M+H]$^+$ Reference Example 35

Methyl(1-{[6-chloro-5-methoxy-2-(pyrazolo[5,1-b][1,3]thiazol-7-yl)pyrimidin-4-yl]carbonyl}piperidin-4-yl)carbamate

[Step 1] Preparation of ethyl 6-hydroxy-5-methoxy-2-(pyrazolo[5,1-b][1,3]thiazol-7-yl)pyrimidine-4-carboxylate To a solution of methoxyacetic acid (1.0 g) and diethyl oxalate (1.24 g) in THF (10 mL) were added 60% sodium hydride (372 mg) and ethanol (1 drop), and the mixture was stirred at room temperature for 6 h. The reaction solution was concentrated under reduced pressure to give solid. On the one hand, to a solution of pyrazolo[5,1-b][1,3]thiazole-7-carbonitrile obtained in Reference Example 1 (10 g) in methanol (300 mL) was added a solution of 28% sodium methoxide in methanol (41 mL), and the mixture was stirred at room temperature for 1 h. Then, ammonium chloride (21.5 g) was added thereto, and the mixture was stirred at 80° C. for 2 h. The reaction solution was concentrated under reduced pressure, the resulting residue was dissolved in ethanol (5 mL), and the solution of the above solid in ethanol (5 mL) and sodium ethoxide (576 mg) were added to the solution, and the mixture was stirred at 80° C. overnight. To the reaction mixture was added a small amount of acetic acid, the mixture was concentrated under reduced pressure, the resulting residue was diluted with ethyl acetate, and the liquid was separated by an addition of saturated aqueous sodium bicarbonate solution. The aqueous layer was further extracted with ethyl acetate, and the combined organic layer was dried over anhydrous magnesium sulfate, and concentrated under reduced pressure. The resulting residue was purified by silica gel column chromatography to give the title compound (119 mg).
MS (m/z): 321 [M+H]$^+$

[Step 2] Preparation of 6-hydroxy-5-methoxy-2-(pyrazolo[5,1-b][1,3]thiazol-7-yl)pyrimidine-4-carboxylic acid To a solution of ethyl 6-hydroxy-5-methoxy-2-(pyrazolo[5,1-b][1,3]thiazol-7-yl)pyrimidine-4-carboxylate obtained in Step 1 (115 mg) in THF (2 mL) and water (1 mL) was added lithium hydroxide monohydrate (60 mg), and the mixture was stirred at 60° C. for 6 h. To the reaction mixture was added 1 M aqueous solution of hydrochloric acid to neutralize the mixture, which was concentrated under reduced pressure, and the resulting residue was washed with water, collected on a filter, and heat-dried under reduced pressure to give the title compound (73 mg).
MS (m/z): 293 [M+H]$^+$

[Step 3] Preparation of methyl(1-{[6-chloro-5-methoxy-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using 6-hydroxy-5-methoxy-2-(pyrazolo[5,1-b][1,3]thiazol-7-yl)pyrimidine-4-carboxylic acid obtained in Step 2 in place of 6-hydroxy-2-(pyrazolo[5,1-b][1,3]thiazol-7-yl)pyrimidine-4-carboxylic acid.
MS (m/z): 451, 453 [M+H]$^+$ Reference Example 36

Methyl(1-{[6-chloro-5-ethoxy-2-(pyrazolo[5,1-b][1,3]thiazol-7-yl)pyrimidin-4-yl]carbonyl}piperidin-4-yl)carbamate

[Step 1] Preparation of 6-hydroxy-5-ethoxy-2-(pyrazolo[5,1-b][1,3]thiazol-7-yl)pyrimidine-4-carboxylic acid To a solution of 2-ethoxyethyl acetate (1 g) in THF (10 mL) were added diethyl oxalate (1.1 g) and 60% sodium hydride (333 mg) followed by an addition of a catalytic amount of ethanol, and the mixture was stirred at room temperature overnight. The reaction mixture was concentrated under reduced pressure, and the resulting residue was suspended in sodium hydroxide (762 mg) and water (10 mL).
To a solution of pyrazolo[5,1-b][1,3]thiazole-7-carbonitrile obtained in Reference Example 1 (406 mg) in methanol (10 mL) was added a solution of 28% sodium methoxide in methanol (1.7 mL), and the mixture was stirred at room temperature for 1 h. Then, ammonium chloride (873 mg) was added thereto, and the mixture was stirred at 80° C. for 2 h. The reaction mixture was concentrated under reduced pressure, to the resulting residue was added the above suspension, and the mixture was stirred at 100° C. for 10 h. To the reaction mixture was added conc. hydrochloric acid to make the solution acidic, and the precipitated solid was collected on a filter, and dried to obtain the title compound (217 mg).
MS (m/z): 307 [M+H]$^+$

[Step 2] Preparation of methyl(1-{[6-chloro-5-ethoxy-2-(pyrazolo[5,1-b][1,3]thiazol-7-yl)pyrimidin-4-yl]carbonyl}piperidin-4-yl)carbamate Analogous to the method in Reference Example 14 Step 2, the title compound was synthesized by using 6-hydroxy-5-ethoxy-2-(pyrazolo[5,1-b][1,3]thiazol-7-yl)pyrimidine-4-carboxylic acid obtained in Step 1 in place of 6-hydroxy-2-(pyrazolo[5,1-b][1,3]thiazol-7-yl)pyrimidine-4-carboxylic acid.
MS (m/z): 465, 467 [M+H]$^+$ Reference Example 37

6-{[(2S)-1-(Difluoromethoxy)propan-2-yl]amino}-2-(pyrazolo[5,1-b][1,3]thiazol-7-yl)pyrimidine-4-carboxylic acid

[Step 1] Preparation of methyl 6-{[(2S)-1-(difluoromethoxy)propan-2-yl]amino}-2-(pyrazolo[5,1-b][1,3]thiazol-7-yl)pyrimidine-4-carboxylate To a solution of methyl 6-chloro-2-(pyrazolo[5,1-b][1,3]thiazol-7-yl)pyrimidine-4-carboxylate obtained in Reference Example 3 (30 mg) in DMF (0.5 mL) were added (2S)-1-(difluoromethoxy)propan-2-amine hydrochloride obtained in Reference Example 6 (21 mg) and DIPEA (0.1 mL), and the mixture was stirred at 100° C. for 3 h. The reaction mixture was purified by silica gel column chromatography to give the title compound (22 mg).
MS (m/z): 384 [M+H]$^+$

[Step 2] Preparation of 6-{[(2S)-1-(difluoromethoxy)propan-2-yl]amino}-2-(pyrazolo[5,1-b][1,3]thiazol-7-yl)pyrimidine-4-carboxylic acid To a solution of methyl 6-{[(2S)-1-(difluoromethoxy)propan-2-yl]amino}-2-(pyrazolo[5,1-b][1,3]thiazol-7-yl)pyrimidin-4-carboxylate obtained in Step 1 (15 mg) in THF (3 mL) and water (1 mL) was added lithium hydroxide monohydrate (5 mg), and the mixture was stirred at 50° C. for 2 h. To the reaction mixture was added 1 M aqueous solution of hydrochloric acid to make the solution acidic, the aqueous layer was extracted with a mixed solvent of chloroform and methanol, and the organic layer was dried over anhydrous magnesium sulfate, and concentrated under reduced pressure to give the title compound (17 mg).
MS (m/z): 370 [M+H]$^+$ Reference Example 38

6-{[(1S)-1-Cyclopropylethyl]amino}-2-(pyrazolo[5,1-b][1,3]thiazol-7-yl)pyrimidine-4-carboxylic acid

[Step 1] Preparation of methyl 6-{[(1S)-1-cyclopropylethyl]amino}-2-(pyrazolo[5,1-b][1,3]thiazol-7-yl)pyrimidine-4-carboxylate To a solution of methyl 6-chloro-2-(pyrazolo[5,1-b][1,3]thiazol-7-yl)pyrimidine-4-carboxylate obtained in Reference Example 3 (50 mg) in DMF (2 mL) were added DIPEA (88 µL) and (1S)-1-cyclopropylethanamine (16 mg), and the mixture was stirred at 80° C. for 3 h. The reaction mixture was purified by silica gel column chromatography to give the title compound (40 mg).
MS (m/z): 344 [M+H]$^+$

[Step 2] Preparation of 6-{[(1S)-1-cyclopropylethyl]amino}-2-(pyrazolo[5,1-b][1,3]thiazol-7-yl)pyrimidine-4-carboxylic acid To a solution of methyl 6-{[(1S)-1-cyclopropylethyl]amino}-2-(pyrazolo[5,1-b][1,3]thiazol-7-yl)pyrimidine-4-carboxylate obtained in Step 1 (40 mg) in THF (9 mL) and water (3 mL) was added lithium hydroxide monohydrate (10 mg), and the mixture was stirred at room temperature for 1 h. To the reaction mixture was added 1 M aqueous solution of hydrochloric acid to make the solution acidic, THF was distilled off under reduced pressure, and the aqueous layer was extracted with chloroform. The organic layer was dried over anhydrous sodium sulfate, and concentrated under reduced pressure to give the title compound (36 mg).

MS (m/z): 330 [M+H]$^+$

Reference Example 39

6-{[(1R)-1-Cyclopropylethyl]amino}-2-(pyrazolo[5, 1-b][1,3]thiazol-7-yl)pyrimidine-4-carboxylic acid Analogous to the method in Reference Example 38 Steps 1 and 2, the title compound was synthesized by using (1R)-1-cyclopropylethanamine in place of (1S)-1-cyclopropylethanamine.

MS (m/z): 330 [M+H]$^+$

Reference Example 40

6-{[(2S)-3,3-Dimethylbutan-2-yl]amino}-2-(pyrazolo[5,1-b][1,3]thiazol-7-yl)pyrimidine-4-carboxylic acid Analogous to the method in Reference Example 38 Steps 1 and 2, the title compound was synthesized by using (2S)-3,3-dimethylbutan-2-amine in place of (1S)-1-cyclopropylethanamine.

MS (m/z): 346 [M+H]$^+$

Reference Example 41

6-{[(2R)-3,3-Dimethylbutan-2-yl]amino}-2-(pyrazolo[5,1-b][1,3]thiazol-7-yl)pyrimidine-4-carboxylic acid Analogous to the method in Reference Example 38 Steps 1 and 2, the title compound was synthesized by using (2R)-3,3-dimethylbutan-2-amine in place of (1S)-1-cyclopropylethanamine.

MS (m/z): 346 [M+H]$^+$

Reference Example 42

6-{[(1S,2S)-2-(difluoromethoxy)cyclopentyl]amino}-2-(pyrazolo[5,1-b][1,3]thiazol-7-yl)pyrimidine-4-carboxylic acid Analogous to the method in Reference Example 38 Steps 1 and 2, the title compound was synthesized by using (1S,2S)-2-(difluoromethoxy)cyclopentanamine hydrochloride obtained in Reference Example 7 in place of (1S)-1-cyclopropylethanamine.

MS (m/z): 396 [M+H]$^+$

Reference Example 43

Methyl 6-{[(1S)-1-cyclopropylethyl](methyl)amino}-2-(pyrazolo[5,1-b][1,3]thiazol-7-yl)pyrimidine-4-carboxylate To a solution of methyl 6-{[(1S)-1-cyclopropylethyl]amino}-2-(pyrazolo[5,1-b][1,3]thiazol-7-yl)pyrimidine-4-carboxylate obtained in Reference Example 38 Step 1 (820 mg) in DMF (8.0 mL) was added 60% sodium hydride (115 mg) at room temperature, and the mixture was stirred for 3 min. Then, iodomethane (1.4 g) was added thereto and the mixture was stirred for 5 min. Further, an additional 60% sodium hydride (11 mg) was added thereto and the mixture was stirred for 5 min. The reaction solution was diluted with chloroform, separated by adding water, the aqueous layer was further extracted with chloroform, and the combined organic layer was dried over anhydrous magnesium sulfate, and concentrated under reduced pressure. The resulting residue was purified by silica gel column chromatography to give the title compound (665 mg).

MS (m/z): 358 [M+H]$^+$

Reference Example 44

6-{[(1R)-1-(4-methoxyphenyl)ethyl]amino}-2-(pyrazolo[5,1-b][1,3]thiazol-7-yl)pyrimidine-4-carboxylic acid Analogous to the method in Reference Example 38 Steps 1 and 2, the title compound was synthesized by using (1R)-1-(4-methoxyphenyl)ethanamine in place of (1S)-1-cyclopropylethanamine.

MS (m/z): 396 [M+H]$^+$

Reference Example 45

6-{[(1S,2S)-2-(Difluoromethoxy)cyclopentyl](methyl)amino}-2-(pyrazolo[5,1-b][1,3]thiazol-7-yl)pyrimidine-4-carboxylic acid

[Step 1] Preparation of methyl 6-{[(1S,2S)-2-(difluoromethoxy)cyclopentyl](methyl)amino}-2-(pyrazolo[5,1-b][1,3]thiazol-7-yl)pyrimidine-4-carboxylate To a solution of benzyl[(S,2S)-2-(difluoromethoxy)cyclopentyl]carbamate obtained in Reference Example 7 Step 2 (710 mg) in DMF (5 mL) was added 60% sodium hydride (149 mg) in portions at room temperature, and the resulting mixture was stirred for 10 min. Then, iodomethane (530 mg) was added thereto, and the mixture was stirred for 2 h. The reaction mixture was diluted with ethyl acetate, separated by adding water, and the aqueous layer was further extracted with ethyl acetate. The combined organic layer was dried over anhydrous magnesium sulfate, and concentrated under reduced pressure. The resulting residue was purified by silica gel column chromatography to give an oil (338 mg). To a solution of the resulting oil (300 mg) in ethanol (6 mL) was added 20% palladium hydroxide (on activated carbon, 100 mg), and medium pressure catalytic reduction was conducted. To the mixture was added 4 M hydrogen chloride-ethyl acetate, the reaction solution was filtered to remove the palladium, and the mother liquid was concentrated under reduced pressure to give a solid (271 mg). To a solution of the obtained solid (75 mg) and methyl 6-chloro-2-(pyrazolo[5,1-b][1,3]thiazol-7-yl)pyrimidine-4-carboxylate obtained in Reference Example 3 (100 mg) in DMF (2 mL) was added DIPEA (0.18 mL), and the mixture was stirred at 100° C. for 3 h. The reaction mixture was purified by silica gel column chromatography to give the title compound (102 mg).

MS (m/z): 424 [M+H]$^+$

[Step 2] Preparation of 6-{[(1S,2S)-2-(difluoromethoxy)cyclopentyl](methyl)amino}-2-(pyrazolo[5,1-b][1,3]thiazol-7-yl)pyrimidine-4-carboxylic acid Analogous to the method in Reference Example 38 Step 2, the title compound was synthesized by using methyl 6-{[(1S,2S)-2-(difluoromethoxy)cyclopentyl](methyl) amino}-2-(pyrazolo[5,1-b][1,3]thiazol-7-yl)pyrimidine-4-carboxylate obtained in Step 1 in place of methyl 6-{[(1S)-1-cyclopropylethyl]amino}-2-(pyrazolo[5,1-b][1,3]thiazol-7-yl)pyrimidine-4-carboxylate.

MS (m/z): 410 [M+H]$^+$

Reference Example 46

6-{[(1S,2S)-2-methoxycyclopentyl]amino}-2-(pyrazolo[5,1-b][1,3]thiazol-7-yl)pyrimidine-4-carboxylic acid

[Step 1] Preparation of methyl 6-{[(1S,2S)-2-methoxycyclopentyl]amino}-2-(pyrazolo[5,1-b][1,3]thiazol-7-yl)pyrimidine-4-carboxylate To a solution of tert-butyl N-[(1S,2S)-2-hydroxycyclopentyl]carbamate (4.0 g) in DMF (20 mL) was added 60% sodium hydride (870 mg) in portions under ice cooling, and the mixture was stirred at room temperature for 10 min. Then, iodomethane (3.1 g) was added thereto under ice cooling, and the mixture was stirred at room temperature. The reaction mixture was diluted with ethyl acetate, separated by adding water, and the aqueous layer was further extracted with ethyl acetate. The combined organic layer was washed with saturated brine, dried over anhydrous sodium sulfate, and concentrated under reduced pressure. The resulting residue was purified by silica gel column chromatography to give a solid 1 (2.3 g). To a solution of the obtained solid 1 in dichloromethane (10 mL) was added 4 M hydrogen chloride-ethyl acetate solution (5.3 mL), and the mixture was stirred at room temperature for 4 h. The solvent was concentrated under reduced pressure to give a solid 2 (1.5 g). To a solution of the obtained solid 2 (93 mg) and methyl 6-chloro-2-(pyrazolo[5,1-b][1,3]thiazol-7-yl)pyrimidine-4-carboxylate obtained in Reference Example 3 (150 mg) in DMF (2.0 mL) was added DIPEA (0.26 mL), and the mixture was stirred at 100° C. for 3 h. The reaction mixture was purified by silica gel column chromatography to give the title compound (112 mg).

MS (m/z): 374 [M+H]$^+$

[Step 2] Preparation of 6-{[(1S,2S)-2-methoxycyclopentyl]amino}-2-(pyrazolo[5,1-b][1,3]thiazol-7-yl)pyrimidine-4-carboxylic acid Analogous to the method in Reference Example 38 Step 2, the title compound was synthesized by using methyl 6-{[(1S,2S)-2-methoxycyclopentyl]amino}-2-(pyrazolo[5,1-b][1,3]thiazol-7-yl)pyrimidine-4-carboxylate obtained in Step 1 in place of methyl 6-{[(1S)-1-cyclopropylethyl]amino}-2-(pyrazolo[5,1-b][1,3]thiazol-7-yl)pyrimidine-4-carboxylate.

MS (m/z): 360 [M+H]$^+$

Reference Example 47

6-{[(2S)-3,3-Dimethylbutan-2-yl]amino}-5-methyl-2-(pyrazolo[5,1-b][1,3]thiazol-7-yl)pyrimidine-4-carboxylic acid

[Step 1] Preparation of methyl 6-{[(2S)-3,3-dimethylbutan-2-yl]amino}-5-methyl-2-(pyrazolo[5,1-b][1,3]thiazol-7-yl)pyrimidine-4-carboxylate To a solution of methyl 6-chloro-5-methyl-2-(pyrazolo[5,1-b][1,3]thiazol-7-yl)pyrimidin-4-carboxylate obtained in Reference Example 5 (50 mg) in NMP (1 mL) were added (2S)-3,3-dimethylbutan-2-amine (33 mg) and DIPEA (56 µL), and the mixture was stirred at 110° C. for 2 h 30 min. The mixture was diluted with ethyl acetate, separated by adding saturated aqueous sodium bicarbonate solution, the aqueous layer was further extracted with ethyl acetate, and the combined organic layer was dried over anhydrous magnesium sulfate, and concentrated under reduced pressure. The resulting residue was purified by silica gel column chromatography to give the title compound (39 mg).

MS (m/z): 374 [M+H]$^+$

[Step 2] Preparation of 6-{[(2S)-3,3-dimethylbutan-2-yl]amino}-5-methyl-2-(pyrazolo[5,1-b][1,3]thiazol-7-yl)pyrimidine-4-carboxylic acid To a solution of methyl 6-{[(2S)-3,3-dimethylbutan-2-yl]amino}-5-methyl-2-(pyrazolo[5,1-b][1,3]thiazol-7-yl)pyrimidine-4-carboxylate obtained in Step 1 (35 mg) in THF (5.0 mL) and water (2.0 mL) was added lithium hydroxide monohydrate (12 mg), and the mixture was stirred at 50° C. for 1 h. To the reaction mixture was added 1 M aqueous solution of hydrochloric acid to make the solution acidic, and the aqueous layer was extracted with a mixed solvent of chloroform and methanol. The organic layer was dried over anhydrous magnesium sulfate, and concentrated under reduced pressure to give the title compound (35 mg).

MS (m/z): 360 [M+H]$^+$

Reference Example 48

6-{[(1S)-1-Cyclopropylethyl]amino}-5-methyl-2-(pyrazolo[5,1-b][1,3]thiazol-7-yl)pyrimidine-4-carboxylic acid Analogous to the method in Reference Example 47 Steps 1 and 2, the title compound was synthesized by using (1S)-1-cyclopropylethanamine in place of (2S)-3,3-dimethylbutan-2-amine.

MS (m/z): 344 [M+H]$^+$

Reference Example 49

6-[(2,2-Dimethylpropyl)amino]-2-(pyrazolo[5,1-b][1,3]thiazol-7-yl)pyrimidine-4-carboxylic acid Analogous to the method in Reference Example 38 Steps 1 and 2, the title compound was synthesized by using 2,2-dimethylpropan-1-amine in place of (1S)-1-cyclopropylethanamine.

MS (m/z): 332 [M+H]$^+$

Reference Example 50

1-cyclopropyl-3-piperidin-4-ylurea hydrochloride

To a solution of cyclopropanecarboxylic acid (300 mg) in toluene (3 mL) were added TEA (0.5 mL) and diphenylphosphoryl azide (1.1 g), and the mixture was stirred at 80° C. for 3 h. Then, tert-butyl 4-aminopiperidine-1-carboxylate (600 mg) was added thereto at room temperature, and the mixture was stirred for 1 h. The reaction solution was concentrated under reduced pressure, and the resulting residue was purified by silica gel column chromatography to give a solid (234 mg). To a solution of the obtained solid (230 mg) in dichloromethane (5 mL) was added 4 M hydrogen chloride-ethyl acetate solution (0.6 mL), and the mixture was stirred at room temperature overnight. The reaction solution was concentrated under reduced pressure to give the title compound (200 mg).

MS (m/z): 184 [M−Cl]$^+$

Reference Example 51

1-Fluoro-2-methylpropan-2-yl piperidin-4-ylcarbamate

To a solution of 1-benzylpiperidin-4-amine (4.0 g) and 1-{[(1-fluoro-2-methylpropan-2-yl)oxy]carbonyl}-3-methyl-1H-imidazole-3-ium iodide (7.6 g) (which was prepared analogously to the method described in, for example, Bioorganic Medicinal Chemistry, 2011, 19, 1580-1593) in acetonitrile (20 mL) was added TEA (5.9 mL), and the mixture was stirred at room temperature for 1 h. To the reaction mixture was added water, and the solution was extracted with chloroform. The organic layer was dried over anhydrous magnesium sulfate, concentrated under reduced pressure, and the resulting residue was purified by silica gel column chromatography to give a solid (2.0 g). To a solution of the obtained solid (2.0 g) in ethanol (20 mL) was added 20% palladium hydroxide (on activated carbon, 1.0 g), and medium pressure catalytic reduction was conducted. The reaction solution was filtered to remove the palladium, the mother liquid was concentrated under reduced pressure, and the resulting residue was washed with ethyl acetate to give the tile compound (306 mg).

MS (m/z): 219 [M+H]$^+$

Reference Example 52

2-(Dimethylamino)ethyl piperidin-4-ylcarbamate

Analogous to the method in Reference Example 25 Step 1, the title compound was synthesized by using 2-dimethylaminoethanol in place of 2,2-difluoroethanol.

$^1$H-NMR (CDCl$_3$) δ: 1.21-1.35 (2H, m), 1.90-2.00 (2H, m), 2.28 (6H, s), 2.51-2.59 (2H, m), 2.62-2.70 (2H, m), 3.00-3.10 (2H, m), 3.52-3.64 (1H, m), 4.14 (2H, t), 4.74 (1H, br)

Example 1

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)cyclopropanecarboxamide hydrochloride

[Step 1] Preparation of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide To a solution of 6-{[(1S)-1-cyclopropylethyl]amino}-2-(pyrazolo[5,1-b][1,3]thiazol-7-yl)pyrimidine-4-carboxylic acid obtained in Reference Example 38 (15 mg) in DMF (1.0 mL) were added N-(piperidin-4-yl)cyclopropanecarboxamide (11 mg), DIPEA (24 μL) and HATU (26 mg), and the mixture was stirred at room temperature for 1 h. The reaction mixture was purified by silica gel column chromatography to give the title compound (9 mg).

MS (m/z): 480 [M+H]$^+$

[Step 2] Preparation of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide hydrochloride To a solution of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide obtained in Step 1 (540 mg) in dichloromethane was added 4 M hydrogen chloride-ethyl acetate solution (0.5 mL). The reaction solution was concentrated under reduced pressure to give the title compound (580 mg).

MS (m/z): 480 [M−Cl]$^+$
Specific rotation[α]$^D_{25}$=−45.2° (c=1.00, DMSO)

Example 2

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)acetamide Analogous to the method in Example 1 Step 1, the title compound was synthesized by using N-(4-piperidyl)acetamide in place of N-(piperidin-4-yl)cyclopropanecarboxamide.

MS (m/z): 454 [M+H]$^+$

Example 3

N-(1-{[6-{[(2S)-3,3-Dimethylbutan-2-yl]amino}-2-(pyrazolo[5,1-b][1,3]thiazol-7-yl)pyrimidin-4-yl]carbonyl}piperidin-4-yl)cyclopropanecarboxamide To a solution of 6-{[(2S)-3,3-dimethylbutan-2-yl]amino}-2-(pyrazolo[5,1-b][1,3]thiazol-7-yl)pyrimidine-4-carboxylic acid obtained in Reference Example 40 (15 mg) in DMF (1.0 mL) were added N-(piperidin-4-yl)cyclopropanecarboxamide (11 mg), DIPEA (23 μL) and HATU (25 mg), and the mixture was stirred at room temperature for 1 h. The reaction mixture was purified by silica gel column chromatography to give the title compound (7 mg).

MS (m/z): 496 [M+H]$^+$

Example 4

N-(1-{[6-{[(2S)-3,3-Dimethylbutan-2-yl]amino}-2-(pyrazolo[5,1-b][1,3]thiazol-7-yl)pyrimidin-4-yl]carbonyl}piperidin-4-yl)acetamide Analogous to the method in Example 3, the title compound was synthesized by using N-(4-piperidyl)acetamide in place of N-(piperidin-4-yl)cyclopropanecarboxamide.

MS (m/z): 470 [M+H]$^+$

Example 5

N-(1-{[6-{[(1S,2S)-2-(Difluoromethoxy)cyclopentyl](methyl)amino}-2-(pyrazolo[5,1-b][1,3]thiazol-7-yl)pyrimidin-4-yl]carbonyl}piperidin-4-yl)cyclopropanecarboxamide To a solution of 6-{[(1S,2S)-2-(difluoromethoxy)cyclopentyl](methyl)amino}-2-(pyrazolo[5,1-b][1,3]thiazol-7-yl)

pyrimidine-4-carboxylic acid obtained in Reference Example 45 (15 mg) in DMF (1.0 mL) were added N-(piperidin-4-yl)cyclopropanecarboxamide (9.0 mg), DIPEA (19 µL) and HATU (21 mg), and the mixture was stirred at room temperature for 3 h. The reaction mixture was purified by silica gel column chromatography to give the title compound (16 mg).

MS (m/z): 560 [M+H]$^+$

Example 6

N-(1-{[6-{[(2S)-3,3-Dimethylbutan-2-yl]amino}-5-methyl-2-(pyrazolo[5,1-b][1,3]thiazol-7-yl)pyrimidin-4-yl]carbonyl}piperidin-4-yl)acetamide To a solution of 6-{[(2S)-3,3-dimethylbutan-2-yl]amino}-5-methyl-2-(pyrazolo[5,1-b][1,3]thiazol-7-yl)pyrimidine-4-carboxylic acid obtained in Reference Example 47 (15 mg) and N-(4-piperidyl)acetamide (9.0 mg) in DMF (1.0 mL) were added DIPEA (14 µL) and HATU (24 mg), and the mixture was stirred at room temperature for 1 h 30 min. The reaction mixture was purified by silica gel column chromatography to give the title compound (15 mg).

MS (m/z): 484 [M+H]$^+$

Example 7

N-(1-{[6-{[(2S)-3,3-Dimethylbutan-2-yl]amino}-5-methyl-2-(pyrazolo[5,1-b][1,3]thiazol-7-yl)pyrimidin-4-yl]carbonyl}piperidin-4-yl)cyclopropanecarboxamide Analogous to the method in Example 6, the title compound was synthesized by using N-(piperidin-4-yl)cyclopropanecarboxamide in place of N-(4-piperidyl)acetamide.

MS (m/z): 510 [M+H]$^+$

Example 8

N-[1-({6-[({1-[(Difluoromethoxy)methyl]cyclopropyl}methyl)amino]-2-(pyrazolo[5,1-b][1,3]thiazol-7-yl)pyrimidin-4-yl}carbonyl)piperidin-4-yl]cyclopropanecarboxamide To a solution of methyl 6-chloro-2-(pyrazolo[5,1-b][1,3]thiazol-7-yl)pyrimidine-4-carboxylate obtained in Reference Example 3 (200 mg) in DMF (1.5 mL) wore added {1-[(difluoromethoxy)methyl]cyclopropyl}methanamine obtained in Reference Example 8 (113 mg) and DIPEA (236 µL), and the mixture was stirred at 80° C. for 1 h 30 min. To the reaction solution was added water, the solution was extracted with ethyl acetate, and the organic layer was washed with saturated brine, dried over anhydrous magnesium sulfate, and concentrated under reduced pressure. The resulting residue was purified by silica gel column chromatography to give a solid 1 (233 mg). To a solution of the obtained solid 1 (210 mg) in THF (4.0 mL) and water (1.0 mL) was added lithium hydroxide monohydrate (32 mg), and the mixture was stirred at 40° C. for 20 min. The reaction solution was neutralized with 1 M aqueous solution of hydrochloric acid, and concentrated under reduced pressure to give a solid 2 (246 mg). To a solution of the obtained solid 2 (40 mg) in DMF (0.5 mL) were added N-(piperidin-4-yl)cyclopropanecarboxamide (26 mg), DIPEA (35 µL) and HATU (58 mg), and the mixture was stirred at room temperature overnight. To the reaction solution was added water, and the mixture was extracted with ethyl acetate. The organic layer was washed with saturated brine, dried over anhydrous magnesium sulfate, and concentrated under reduced pressure. The resulting residue was purified by silica gel column chromatography to give the title compound (25 mg).

MS (m/z): 546 [M+H]$^+$

Example 9

N-[1-({6-[({1-[(Difluoromethoxy)methyl]cyclobutyl}methyl)amino]-2-(pyrazolo[5,1-b][1,3]thiazol-7-yl)pyrimidin-4-yl}carbonyl)piperidin-4-yl]cyclopropanecarboxamide Analogous to the method in Example 8, the title compound was synthesized by using {1-[(difluoromethoxy)methyl]cyclobutyl}methanamine obtained in Reference Example 9 in place of {1-[(difluoromethoxy)methyl]cyclopropyl}methanamine.

MS (m/z): 560 [M+H]$^+$

Example 10

N-[1-({6-[({1-[(Difluoromethoxy)methyl]cyclopentyl}methyl)amino]-2-(pyrazolo[5,1-b][1,3]thiazol-7-yl)pyrimidin-4-yl}carbonyl)piperidin-4-yl]cyclopropanecarboxamide Analogous to the method in Example 8, the title compound was synthesized by using {1-[(difluoromethoxy)methyl]cyclopentyl}methanamine obtained in Reference Example 10 in place of {1-[(difluoromethoxy)methyl]cyclopropyl}methanamine.

MS (m/z): 574 [M+H]$^+$

Example 11

N-[1-({6-[({4-[(Difluoromethoxy)methyl]tetrahydro-2H-pyran-4-yl}methyl)amino]-2-(pyrazolo[5,1-b][1,3]thiazol-7-yl)pyrimidin-4-yl}carbonyl)piperidin-4-yl]cyclopropanecarboxamide Analogous to the method in Example 8, the title compound was synthesized by using {4-[(difluoromethoxy)methyl]tetrahydro-2H-pyran-4-yl}methanamine obtained in Reference Example 11 in place of {1-[(difluoromethoxy)methyl]cyclopropyl}methanamine.

MS (m/z): 590 [M+H]$^+$

Example 12

N-(1-{[6-{[(1S)-1-Cyclopropylethyl]amino}-5-methyl-2-(pyrazolo[5,1-b][1,3]thiazol-7-yl)pyrimidin-4-yl]carbonyl}piperidin-4-yl)cyclopropanecarboxamide To a solution of 6-{[(1S)-1-cyclopropylethyl]amino}-5-methyl-2-(pyrazolo[5,1-b][1,3]thiazol-7-yl)pyrimidine-4-carboxylic acid obtained in Reference Example 48 (20 mg) in DMF (1 mL) were added N-(piperidin-4-yl)cyclopropanecarboxamide (15 mg), DIPEA (20 µL) and HATU (33 mg), and the mixture was stirred at room temperature for 1 h. The reaction mixture was purified by silica gel column chromatography to give the title compound (21 mg).

MS (m/z): 494 [M+H]$^+$

Example 13

N-(1-{[6-{[(1S)-1-Cyclopropylethyl]amino}-5-methyl-2-(pyrazolo[5,1-b][1,3]thiazol-7-yl)pyrimidin-4-yl]carbonyl}piperidin-4-yl)acetamide Analogous to the method in Example 12, the title compound was synthesized by using N-(4-piperidyl)acetamide in place of N-(piperidin-4-yl)cyclopropanecarboxamide.
MS (m/z): 468 [M+H];

Example 14

N-(1-{[6-{[(1S,2S)-2-(Difluoromethoxy)cyclopentyl]amino}-2-(pyrazolo[5,1-b][1,3]thiazol-7-yl)pyrimidin-4-yl]carbonyl}piperidin-4-yl)cyclopropanecarboxamide To a solution of 6-{[(1S,2S)-2-(difluoromethoxy)cyclopentyl]amino}-2-(pyrazolo[5,1-b][1,3]thiazol-7-yl)pyrimidine-4-carboxylic acid obtained in Reference Example 42 (20 mg) in DMF (1 mL) were added N-(piperidin-4-yl)cyclopropanecarboxamide (13 mg), DIPEA (26 µL) and HATU (29 mg), and the mixture was stirred at room temperature for 1 h. The reaction mixture was purified by silica gel column chromatography to give the title compound (7 mg).
MS (m/z): 546 [M+H]$^+$

Example 15

N-[1-({6-[(2,2-Dimethylpropyl)amino]-2-(pyrazolo[5,1-b][1,3]thiazol-7-yl)pyrimidin-4-yl}carbonyl)piperidin-4-yl]cyclopropanecarboxamide To a solution of methyl 6-chloro-2-(pyrazolo[5,1-b][1,3]thiazol-7-yl)pyrimidine-4-carboxylate obtained in Reference Example 3 (30 mg) in DMF (0.1 mL) were added 2,2-dimethylpropan-1-amine (9.0 mg) and DIPEA (50 µL), and the mixture was stirred at 100° C. for 3 h. The reaction solution was concentrated under reduced pressure, and the resulting residue was purified by silica gel column chromatography to give a solid 1 (28 mg). To a solution of the obtained solid 1 (28 mg) in dioxane (5.0 mL) and water (1.0 mL) was added lithium hydroxide monohydrate (7 mg), and the mixture was stirred at 50° C. for 1 h. The mixture was neutralized with 2 M hydrochloric acid aqueous solution, and the reaction solution was concentrated under reduced pressure to give a solid 2. To a solution of the obtained solid 2 in DMF (1.5 mL) were added N-(piperidin-4-yl)cyclopropanecarboxamide, DIPEA (0.2 mL) and HATU (62 mg), and the mixture was stirred at room temperature for 3 h. The reaction mixture was concentrated under reduced pressure, and the resulting residue was purified by silica gel column chromatography to give the title compound (27 mg).
MS (m/z): 482 [M+H]$^+$

Example 16

N-(1-{[6-{[(2R)-3,3-Dimethylbutan-2-yl]amino}-2-(pyrazolo[5,1-b][1,3]thiazol-7-yl)pyrimidin-4-yl]carbonyl}piperidin-4-yl)cyclopropanecarboxamide Under argon atmosphere, to a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (550 mg) in tert-butanol (20 mL) was added TEA (534 µL) and (2R)-3,3-dimethylbutan-2-amine (258 mg), and the mixture was stirred at 90° C. overnight. The reaction mixture was concentrated under reduced pressure, and the resulting residue was purified by silica gel column chromatography to give the title compound (570 mg).
MS (m/z): 496 [M+H]$^+$
Specific rotation[α]$^D_{25}$=+14.0° (c=1.00, DMSO)

Example 17

N-(1-{[6-{[(2S)-1-(Difluoromethoxy)propan-2-yl]amino}-2-(pyrazolo[5,1-b][1,3]thiazol-7-yl)pyrimidin-4-yl]carbonyl}piperidin-4-yl)cyclopropanecarboxamide To a solution of 6-{[(2S)-1-(difluoromethoxy)propan-2-yl]amino}-2-(pyrazolo[5,1-b][1,3]thiazol-7-yl)pyrimidine-4-carboxylic acid obtained in Reference Example 37 (20 mg) in DMF (0.5 mL) were added N-(piperidin-4-yl)cyclopropanecarboxamide (11 mg), DIPEA (10 µL) and HATU (40 mg), and the mixture was stirred at room temperature for 3 h. The reaction mixture was concentrated under reduced pressure, and the resulting residue was purified by silica gel column chromatography to give the title compound (13 mg).
MS (m/z): 520 [M+H]$^+$

Example 18

N-(1-{[6-{[(1S)-1-Cyclopropylethyl]amino}-5-methyl-2-(pyrazolo[5,1-b][1,3]thiazol-7-yl)pyrimidin-4-yl]carbonyl}piperidin-4-yl)-2,2-difluoroacetamide Analogous to the method in Example 12, the title compound was synthesized by using 2,2-difluoro-N-(4-piperidyl)acetamide obtained in Reference Example 28 Step 1 in place of N-(piperidin-4-yl)cyclopropanecarboxamide.
MS (m/z): 504 [M+H]$^+$

Example 19

N-(1-{[6-{[(1S,2S)-2-Methoxycyclopentyl]amino}-2-(pyrazolo[5,1-b][1,3]thiazol-7-yl)pyrimidin-4-yl]carbonyl}piperidin-4-yl)cyclopropanecarboxamide To a solution of 6-{[(1S,2S)-2-methoxycyclopentyl]amino}-2-(pyrazolo[5,1-b][1,3]thiazol-7-yl)pyrimidine-4-carboxylic acid obtained in Reference Example 46 (20 mg) in DMF (1 mL) were added N-(piperidin-4-yl)cyclopropanecarboxamide (14 mg), DIPEA (29 µL) and HATU (32 mg), and the mixture was stirred at room temperature for 30 min. The reaction mixture was purified by silica gel column chromatography to give the title compound (13 mg).
MS (m/z): 510 [M+H]$^+$

Example 20

[6-{[(1S)-1-Cyclopropylethyl]amino}-2-(pyrazolo[5,1-b][1,3]thiazol-7-yl)pyrimidin-4-yl](4-hydroxypiperidin-1-yl)methanone hydrochloride To a solution of 6-{[(1S)-1-cyclopropylethyl]amino}-2-(pyrazolo[5,1-b][1,3]thiazol-7-yl)pyrimidine-4-carboxylic acid obtained in Reference Example 38 (420 mg) in DMF (5 mL) were added piperidin-4-ol (194 mg), DIPEA (662 µL) and HATU (727 mg), and the mixture was stirred at room temperature for 1 h. The reaction mixture was purified by silica gel column chromatography to give a solid (530 mg). To a solution of the obtained solid in ethyl acetate was added 4 M hydrogen chloride-ethyl acetate solution (0.6 mL). The reaction solution was concentrated under reduced pressure to give the title compound (560 mg).

MS (m/z): 413 [M−Cl]$^+$

Elemental analysis value (for $C_{19}H_{24}N_6O_2S \cdot HCl + 0.3 H_2O + 0.2 CH_3CO_2C_2H_5$).

Calculated value (%) C: 52.93, H: 5.81, N: 17.81.
Found value (%) C: 52.68, H: 5.78, N: 17.78.

Example 21

1-Fluoro-2-methylpropan-2-yl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate hydrochloride Analogous to the method in Example 20, the title compound was synthesized by using 1-fluoro-2-methylpropan-2-yl piperidin-4-ylcarbamate obtained in Reference Example 51 in place of piperidin-4-ol.

MS (m/z): 530 [M−Cl]$^+$

Example 22

Methyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 3, the title compound was synthesized by using methyl piperidin-4-ylcarbamate obtained in Reference Example 14 Step 1 in place of N-(piperidin-4-yl)cyclopropanecarboxamide.

MS (m/z): 486 [M+H]$^+$

Example 23

[6-{[(2S)-3,3-Dimethylbutan-2-yl]amino}-2-(pyrazolo[5,1-b][1,3]thiazol-7-yl)pyrimidin-4-yl](4-hydroxypiperidin-1-yl)methanone Analogous to the method in Example 3, the title compound was synthesized by using piperidin-4-ol in place of N-(piperidin-4-yl)cyclopropanecarboxamide.

MS (m/z): 429 [M+H]$^+$

Example 24

Methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate hydrochloride

[Step 1] Preparation of methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate Under argon atmosphere, to a solution of methyl(1-{[6-chloro-2-(pyrazolo[5,1-b][1,3]thiazol-7-yl)pyrimidin-4-yl]carbonyl}piperidin-4-yl)carbamate obtained in Reference Example 14 (20 mg) in DMF (1 mL) were added DIPEA (16 μL) and (2R)-3-methylbutan-2-amine (6 mg), and the mixture was stirred at 100° C. for 3 h 30 min. The reaction solution was diluted with ethyl acetate, separated by adding saturated aqueous sodium bicarbonate solution, and the aqueous layer was further extracted with ethyl acetate. The combined organic layer was washed with saturated aqueous sodium bicarbonate solution, dried over anhydrous magnesium sulfate, and concentrated under reduced pressure. The resulting residue was purified by silica gel column chromatography to give the title compound (19 mg).

MS (m/z): 472 [M+H]$^+$

[Step 2] Preparation of methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate hydrochloride To a solution of methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate obtained in Step 1 (56 mg) in ethyl acetate was added 4 M hydrogen chloride-ethyl acetate solution (0.1 mL). The reaction solution was concentrated under reduced pressure, and the resulting residue was washed with diethyl ether to give the title compound (50 mg).

MS (m/z): 472 [M−Cl]$^+$

Elemental analysis value (for $C_{22}H_{29}N_7O_3S \cdot HCl + 1.0 H_2O$).

Calculated value (%) C: 50.23, H: 6.13, N: 18.64.
Found value (%) C: 50.47, H: 6.08, N: 18.52.

Example 25

Methyl(1-{[6-{[(2S)-3-methylbutan-2-yl]amino}-2-(pyrazolo[5,1-b][1,3]thiazol-7-yl)pyrimidin-4-yl]carbonyl}piperidin-4-yl)carbamate hydrochloride Analogous to the method in Example 24 Steps 1 and 2, the title compound was synthesized by using (2S)-3-methylbutan-2-amine in place of (2R)-3-methylbutan-2-amine.

MS (m/z): 472 [M−Cl]$^+$

Elemental analysis value (for $C_{22}H_{29}N_7O_3S \cdot HCl + H_2O$).

Calculated value (%) C: 50.23, H: 6.13, N: 18.64.
Found value (%) C: 50.50, H: 6.10, N: 18.27.

Example 26

Methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 24 Step 1, the title compound was synthesized by using (1S)-1-cyclopropylethanamine in place of (2R)-3-methylbutan-2-amine.

MS (m/z): 470 [M+H]$^+$

Specific rotation[α]$^D_{25}$=−53.0° (c=1.00, DMSO)

Example 27

Methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate hydrochloride To a solution of methyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate obtained in Example 26 (2.26 g) in ethyl acetate (100 mL) was added 4 M hydrogen chloride-ethyl acetate solution (2.4 mL). The reaction solution was concentrated under reduced pressure to give the title compound (2.35 g).

MS (m/z): 470 [M−Cl]$^+$

Elemental analysis value (for $C_{22}H_{27}N_7O_3S \cdot HCl + H_2O$).
Calculated value (%) C: 50.42, H: 5.77, N: 18.71.
Found value (%) C: 50.53, H: 5.66, N: 18.97.

Example 28

Ethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 1 Step 1, the title compound was synthesized by using ethyl piperidin-4-ylcarbamate (which was prepared analogous to the method described in, for example, U.S. Pat. No. 4,918,073) in place of N-(piperidin-4-yl)cyclopropanecarboxamide.
MS (m/z): 484 [M+H]$^+$
Specific rotation[$\alpha$]$^D_{25}$=−44.2° (c=1.00, DMSO)

Example 29

Propan-2-yl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate To a solution of propan-2-yl(1-{[6-chloro-2-(pyrazolo[5,1-b][1,3]thiazol-7-yl)pyrimidin-4-yl]carbonyl}piperidin-4-yl)carbamate obtained in Reference Example 22 (200 mg) in DMF (3 mL) were added DIPEA (0.3 mL) and (2R)-3,3-dimethylbutan-2-amine (90 mg), and the mixture was stirred at 120° C. for 4 h in a sealed tube. The reaction solution was diluted with ethyl acetate, separated by using saturated aqueous sodium bicarbonate solution, and the aqueous layer was further extracted with ethyl acetate. The combined organic layer was washed with saturated aqueous sodium bicarbonate solution, dried over anhydrous magnesium sulfate, and concentrated under reduced pressure. The resulting residue was purified by silica gel column chromatography to give the title compound (160 mg).
MS (m/z): 514 [M+H]$^+$ Example 30

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)benzamide

[Step 1] Preparation of tert-butyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 1 Step 1, the title compound was synthesized by using tert-butyl N-(4-piperidyl)carbamate in place of N-(piperidin-4-yl)cyclopropanecarboxamide.
MS (m/z): 512 [M+H]$^+$

[Step 2] Preparation of (4-aminopiperidin-1-yl)[6-{[(1S)-1-cyclopropylethyl]amino}-2-(pyrazolo[5,1-b][1,3]thiazol-7-yl)pyrimidin-4-yl]methanone To a solution of tert-butyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate obtained in Step 1 (75 mg) in dichloromethane (2 mL) was added TFA (0.5 mL), and the mixture was stirred at room temperature for 1 h. The reaction mixture was purified by silica gel column chromatography to give the title compound (65 mg).
MS (m/z): 412 [M+H]$^+$

[Step 3] Preparation of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)benzamide To a solution of (4-aminopiperidin-1-yl)[6-{[(1S)-1-cyclopropylethyl]amino}-2-(pyrazolo[5,1-b][1,3]thiazol-7-yl)pyrimidin-4-yl]methanone obtained in Step 2 (20 mg) in dichloromethane (1 mL) were added DIPEA (25 μL) and benzoyl chloride (10 mg), and the mixture was stirred at room temperature for 30 min. The reaction mixture was purified by silica gel column chromatography to give the title compound (18 mg).
MS (m/z): 516 [M+H]$^+$ Example 31

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)pyridine-3-carboxamide Analogous to the method in Example 30 Step 3, the title compound was synthesized by using pyridine-3-carbonyl chloride hydrochloride in place of benzoyl chloride.
MS (m/z): 517 [M+H]$^+$ Example 32

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)thiophene-2-carboxamide Analogous to the method in Example 30 Step 3, the title compound was synthesized by using thiophene-2-carbonyl chloride in place of benzoyl chloride.
MS (m/z): 522 [M+H]$^+$ Example 33

N-(1-{[6-{[(1S)-1-Cyclopropylethyl](methyl)amino}-2-(pyrazolo[5,1-b][1,3]thiazol-7-yl)pyrimidin-4-yl]carbonyl}piperidin-4-yl)cyclopropanecarboxamide hydrochloride

[Step 1] Preparation of N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide To a solution of methyl 6-{[(1S)-1-cyclopropylethyl](methyl)amino}-2-(pyrazolo[5,1-b][1,3]thiazol-7-yl)pyrimidine-4-carboxylate obtained in Reference Example 43 (25 mg) in THF (3 mL) and water (1 mL) was added lithium hydroxide monohydrate (9 mg), and the mixture was stirred at room temperature for 30 min. The reaction solution was concentrated under reduced pressure, and to a solution of the obtained solid in DMF (2 mL) were added N-(piperidin-4-yl)cyclopropanecarboxamide (18 mg), DIPEA (74 μL) and HATU (40 mg), and the mixture was stirred at room temperature for 1 h. The reaction solution was diluted with chloroform, separated by adding water, and the aqueous layer was further extracted with chloroform. The organic layer was dried over anhydrous magnesium sulfate, and concentrated under reduced pressure. The resulting residue was purified by silica gel column chromatography to give the title compound (30 mg).
MS (m/z): 494 [M+H]$^+$

[Step 2] Preparation of N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide hydrochloride Analogous to the method in Example 27, the title compound was synthesized by using N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)cyclopropanecarboxamide obtained in Step 1.
MS (m/z): 494 [M−Cl]$^+$
Specific rotation[α]$^D_{25}$=−35.7° (c=0.42, DMSO)

Example 34

1-Cyclopropyl-3-(1-{[6-{[(1S)-1-cyclopropylethyl]amino}-2-(pyrazolo[5,1-b][1,3]thiazol-7-yl)pyrimidin-4-yl]carbonyl}piperidin-4-yl)urea Analogous to the method in Example 1 Step 1, the title compound was synthesized by using 1-cyclopropyl-3-piperidin-4-ylurea hydrochloride obtained in Reference Example 50 in place of N-(piperidin-4-yl)cyclopropanecarboxamide.
MS (m/z): 495 [M+H]$^+$ Example 35

[6-{[(1S)-1-Cyclopropylethyl](methyl)amino}-2-(pyrazolo[5,1-b][1,3]thiazol-7-yl)pyrimidin-4-yl][4-(pyrimidin-2-ylamino)piperidin-1-yl]methanone To a solution of methyl 6-{[(1S)-1-cyclopropylethyl](methyl)amino}-2-(pyrazolo[5,1-b][1,3]thiazol-7-yl)pyrimidine-4-carboxylate obtained in Reference Example 43 (665 mg) in THF (10 mL) and water (5 mL) was added lithium hydroxide monohydrate (234 mg), and the mixture was stirred at room temperature for 30 min. The reaction solution was concentrated under reduced pressure, to the resulting residue was added 1 M aqueous solution of hydrochloric acid to make the solution acidic, and the aqueous layer was extracted with a mixed solvent of chloroform and methanol. The organic layer was dried over anhydrous magnesium sulfate, and concentrated under reduced pressure to give a solid (600 mg). To a solution of the obtained solid (15 mg) in DMF (1 mL) were added N-(4-piperidyl)pyrimidin-2-amine (which was prepared analogous to the method described in, for example, WO 2005/105779) (12 mg), DIPEA (15 μL), HATU (25 mg), and the mixture was stirred at room temperature for 1 h 30 min. The reaction mixture was purified by silica gel column chromatography to give the title compound (14 mg).
MS (m/z): 504 [M+H]$^+$ Example 36

N-(1-{[6-(tert-Butylamino)-2-(pyrazolo[5,1-b][1,3]thiazol-7-yl)pyrimidin-4-yl]carbonyl}piperidin-4-yl)cyclopropanecarboxamide

[Step 1] Preparation of methyl 6-(tert-butylamino)-2-(pyrazolo[5,1-b][1,3]thiazol-7-yl)pyrimidine-4-carboxylate To a solution of methyl 6-chloro-2-(pyrazolo[5,1-b][1,3]thiazol-7-yl)pyrimidine-4-carboxylate obtained in Reference Example 3 (30 mg) in DMF (0.5 mL) were added DIPEA (50 μL) and tert-butylamine (7 mg), and the mixture was stirred at 100° C. for 3 h. The reaction solution was concentrated under reduced pressure, and the resulting residue was purified by silica gel column chromatography to give the title compound (15 mg).
MS (m/z): 332 [M+H]$^+$

[Step 2] Preparation of N-(1-{[6-(tert-butylamino)-2-(pyrazolo[5,1-b][1,3]thiazol-7-yl)pyrimidin-4-yl]carbonyl}piperidin-4-yl)cyclopropanecarboxamide To a solution of methyl 6-(tert-butylamino)-2-(pyrazolo[5,1-b][1,3]thiazol-7-yl)pyrimidine-4-carboxylate obtained in Step 1 (15 mg) in THF (5 mL) and water (1 mL) was added lithium hydroxide monohydrate (6 mg), and the mixture was stirred at 40° C. for 1 h. The mixture was neutralized with 2 M hydrochloric acid aqueous solution, and the reaction solution was concentrated under reduced pressure to give a solid. To a solution of the obtained solid in DMF (0.5 mL) were added N-(piperidin-4-yl)cyclopropanecarboxamide (11 mg), DIPEA (16 μL) and HATU (26 mg), and the mixture was stirred at room temperature for 3 h. The reaction mixture was concentrated under reduced pressure, and the resulting residue was purified by silica gel column chromatography to give the title compound (8 mg).
MS (m/z): 468 [M+H]$^+$ Example 37

N-[1-({6-[(1-Methylcyclopropyl)amino]-2-(pyrazolo[5,1-b][1,3]thiazol-7-yl)pyrimidin-4-yl}carbonyl)piperidin-4-yl]cyclopropanecarboxamide Analogous to the method in Example 36 Steps 1 and 2, the title compound was synthesized by using 1-methylcyclopropanamine hydrochloride in place of tert-butylamine.
MS (m/z): 466 [M+H]$^+$ Example 38

N-[1-({6-[(1-Methoxy-2-methylpropan-2-yl)amino]-2-(pyrazolo[5,1-b][1,3]thiazol-7-yl)pyrimidin-4-yl}carbonyl)piperidin-4-yl]cyclopropanecarboxamide Analogous to the method in Example 36 Steps 1 and 2, the title compound was synthesized by using 1-methoxy-2-methylpropan-2-amine hydrochloride (which was prepared analogous to the method described in, for example, WO 2011/087837) in place of tert-butylamine.
MS (m/z): 498 [M+H]$^+$ Example 39

Methyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 24 Step 1, the title compound was synthesized by using (2R)-3,3-dimethylbutan-2-amine in place of (2R)-3-methylbutan-2-amine.
MS (m/z): 486 [M+H]$^+$

Example 40

Ethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate To a solution of 6-{[(2R)-3,3-dimethylbutan-2-yl]amino}-2-(pyrazolo[5,1-b][1,3]thiazol-7-yl)pyrimidine-4-carboxylic acid obtained in Reference Example 41 (30 mg) in DMF (1 mL) were added ethyl piperidin-4-ylcarbamate (which was prepared analogous to the method described in U.S. Pat. No. 4,918,073) (19 mg), DIPEA (34 mg) and HATU (50 mg), and the mixture was stirred at room temperature for 1 h. The reaction mixture was diluted with ethyl acetate, separated by adding saturated aqueous sodium bicarbonate solution, and the aqueous layer was further extracted with ethyl acetate. The combined organic layer was washed with saturated aqueous sodium bicarbonate solution, dried over anhydrous magnesium sulfate, and concentrated under reduced pressure. The resulting residue was purified by silica gel column chromatography to give the title compound (41 mg).

MS (m/z): 500 [M+H]$^+$

Example 41

Propan-2-yl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 29, the title compound was synthesized by using (1S)-1-cyclopropylethanamine in place of (2R)-3,3-dimethylbutan-2-amine.

MS (m/z): 498 [M+H]$^+$

Specific rotation[α]$^D_{25}$=−35.4° (c=0.74, DMSO)

Example 42

N-(1-{[6-{[(1S)-1-Cyclopropylethyl](methyl)amino}-2-(pyrazolo[5,1-b][1,3]thiazol-7-yl)pyrimidin-4-yl]carbonyl}piperidin-4-yl)benzamide

[Step 1] Preparation of tert-butyl(1-{[(6-{[(1S)-1-cyclopropylethyl](methyl)amino}-2-(pyrazolo[5,1-b][1,3]thiazol-7-yl)pyrimidin-4-yl]carbonyl}piperidin-4-yl)carbamate Analogous to the method in Example 35, the title compound was synthesized by using tert-butyl N-(4-piperidyl)carbamate in place of N-(4-piperidyl)pyrimidin-2-amine.

MS (m/z): 526 [M+H]$^+$

[Step 2] Preparation of (4-aminopiperidin-1-yl)[6-{[(1S)-1-cyclopropylethyl](methyl)amino}-2-(pyrazolo[5,1-b][1,3]thiazol-7-yl)pyrimidin-4-yl]methanone To a solution of tert-butyl(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)carbamate obtained in Step 1 (150 mg) in dichloromethane (2 mL) was added TFA (1 mL), and the mixture was stirred at room temperature for 30 min. The reaction mixture was purified by silica gel column chromatography to give the title compound (117 mg).

MS (m/z): 426 [M+H]$^+$

[Step 3] Preparation of N-(1-{[6-{[(1S)-1-cyclopropylethyl](methyl)amino}-2-(pyrazolo[5,1-b][1,3]thiazol-7-yl)pyrimidin-4-yl]carbonyl}piperidin-4-yl)benzamide To a solution of (4-aminopiperidin-1-yl)[6-{[(1S)-1-cyclopropylethyl](methyl)amino}-2-(pyrazolo[5,1-b][1,3]thiazol-7-yl)pyrimidin-4-yl]methanone obtained in Step 2 (20 mg) in dichloromethane (1 mL) were added DIPEA (24 μL) and benzoyl chloride (10 mg), and the mixture was stirred at room temperature for 30 min. The reaction mixture was purified by silica gel column chromatography to give the title compound (13 mg).

MS (m/z): 530 [M+H]$^+$

Example 43

N-(1-{[6-(Cyclopropylmethoxy)-2-(pyrazolo[5,1-b][1,3]thiazol-7-yl)pyrimidin-4-yl]carbonyl}piperidin-4-yl)cyclopropanecarboxamide To a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (20 mg) and cyclopropylmethanol (33 mg) in THF (3.0 mL) was added 60% sodium hydride (2 mg) under ice cooling, and the mixture was stirred at 70° C. for 1 h. The reaction solution was diluted with ethyl acetate, separated by adding water, and the aqueous layer was further extracted with ethyl acetate. The combined organic layer was washed with saturated brine, dried over anhydrous sodium sulfate, and concentrated under reduced pressure. The resulting residue was purified by silica gel column chromatography to give the title compound (15 mg).

MS (m/z): 467 [M+H]$^+$

Example 44

N-[1-({6-[(3,3-Dimethylbutan-2-yl)oxy]-2-(pyrazolo[5,1-b][1,3]thiazol-7-yl)pyrimidin-4-yl}carbonyl)piperidin-4-yl]cyclopropanecarboxamide Analogous to the method in Example 43, the title compound was synthesized by using 3,3-dimethylbutan-2-ol in place of cyclopropylmethanol.

MS (m/z): 497 [M+H]$^+$

Example 45

N-(1-{[6-(Cyclobutyloxy)-2-(pyrazolo[5,1-b][1,3]thiazol-7-yl)pyrimidin-4-yl]carbonyl}piperidin-4-yl)cyclopropanecarboxamide Analogous to the method in Example 43, the title compound was synthesized by using cyclobutanol in place of cyclopropylmethanol.

MS (m/z): 467 [M+H]$^+$

Example 46

N-(1-{[6-{[(1R)-1-Cyclopropylethyl]amino}-2-(pyrazolo[5,1-b][1,3]thiazol-7-yl)pyrimidin-4-yl]carbonyl}piperidin-4-yl)cyclopropanecarboxamide Analogous to the method in Example 16, the title compound was synthesized by using (1R)-1-cyclopropylethanamine in place of (2R)-3,3-dimethylbutan-2-amine.

MS (m/z): 480 [M+H]$^+$

Example 47

N-(1-{[6-{[(1R)-1-Cyclopropylethyl]amino}-2-(pyrazolo[5,1-b][1,3]thiazol-7-yl)pyrimidin-4-yl]carbonyl}piperidin-4-yl)cyclopropanecarboxamide hydrochloride To a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (50 mg) in DMF (1 mL) were added DIPEA (60 µL) and (1R)-1-cyclopropylethanamine (12 mg), and the mixture was stirred at 70° C. for 1 h 40 min. Then, (1R)-1-cyclopropylethanamine (11 mg) was added thereto, and the mixture was stirred at 70° C. for 4 h. The reaction solution was diluted with ethyl acetate, separated by adding water, and the aqueous layer was further extracted with ethyl acetate. The combined organic layer was dried over anhydrous magnesium sulfate, and concentrated under reduced pressure. The resulting residue was purified by silica gel column chromatography to give a solid (50 mg). To a solution of the obtained solid in ethyl acetate was added 4 M hydrogen chloride-ethyl acetate solution (52 µL). The reaction solution was concentrated under reduced pressure, and the resulting residue was washed with diethyl ether to give the title compound (35 mg).

MS (m/z): 481 [M−Cl]

Example 48

N-[1-({6-[(1-Hydroxy-2-methylpropan-2-yl)amino]-2-(pyrazolo[5,1-b][1,3]thiazol-7-yl)pyrimidin-4-yl}carbonyl)piperidin-4-yl]cyclopropanecarboxamide To a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (20 mg) in NMP (1 mL) were added DIPEA (16 µL) and 2-amino-2-methylpropan-1-ol (6 mg), and the mixture was stirred at 100° C. for 2 h. An additional 2-amino-2-methylpropan-1-ol (6 mg) was added thereto, and the mixture was stirred at 110° C. for 2 h. The reaction mixture was purified by silica gel column chromatography to give the title compound (8 mg).

MS (m/z): 484 [M+H]$^+$

Example 49

[6-{[(1S)-1-Cyclopropylethyl]amino}-2-(pyrazolo[5,1-b][1,3]thiazol-7-yl)pyrimidin-4-yl][4-(1,2-oxazol-3-ylamino)piperidin-1-yl]methanone Under argon atmosphere, to a solution of tert-butyl 4-oxopiperidine-1-carboxylate (250 mg) and isoxazole-3-amine (106 mg) in methanol (5 mL) were added acetic acid (75 mg) and 2-picoline borane complex (134 mg), and the mixture was stirred at room temperature for 3 h. To the reaction mixture was added saturated aqueous sodium bicarbonate solution, and the solution was extracted with ethyl acetate. The organic layer was dried over anhydrous magnesium sulfate, and concentrated under reduced pressure. The resulting residue was purified by silica gel column chromatography to give an oil (109 mg). The resulting oil was dissolved in 2 M hydrogen chloride-methanol solution (5 mL), and the mixture was stirred at room temperature overnight. The reaction mixture was concentrated under reduced pressure, and the resulting residue was washed with diethyl ether, and dried to give a solid (90 mg). To a solution of the obtained solid (9 mg) and 6-{[(1S)-1-cyclopropylethyl]amino}-2-(pyrazolo[5,1-b][1,3]thiazol-7-yl)pyrimidine-4-carboxylic acid obtained in Reference Example 38 (10 mg) in DMF (1 mL) were added DIPEA (11 µL) and HATU (17 mg), and the mixture was stirred at room temperature for 1 h 30 min. The reaction mixture was concentrated under reduced pressure, and the resulting residue was purified by silica gel column chromatography to give the title compound (14 mg).

MS (m/z): 479 [M+H]$^+$

Example 50

[6-{[(1S)-1-Cyclopropylethyl]amino}-2-(pyrazolo[5,1-b][1,3]thiazol-7-yl)pyrimidin-4-yl][4-(1,3-thiazol-2-ylamino)piperidin-1-yl]methanone Analogous to the method in Example 49, the title compound was synthesized by using thiazole-2-amine in place of isoxazole-3-amine.

MS (m/z): 495 [M+H]$^+$

Example 51

[6-{[(1S)-1-Cyclopropylethyl]amino}-2-(pyrazolo[5,1-b][1,3]thiazol-7-yl)pyrimidin-4-yl]{4-[(3-methyl-1,2-oxazol-5-yl)amino]piperidin-1-yl}methanone Analogous to the method in Example 49, the title compound was synthesized by using 3-methylisoxazole-5-amine in place of isoxazole-3-amine.

MS (m/z): 493 [M+H]$^+$

Example 52

N-(1-{[6-{[(1R)-1-(4-Methoxyphenyl)ethyl]amino}-2-(pyrazolo[5,1-b][1,3]thiazol-7-yl)pyrimidin-4-yl]carbonyl}piperidin-4-yl)cyclopropanecarboxamide To a solution of 6-{[(1R)-1-(4-methoxyphenyl)ethyl]amino}-2-(pyrazolo[5,1-b][1,3]thiazol-7-yl)pyrimidine-4-carboxylic acid obtained in Reference Example 44 (20 mg) in DMF (1 mL) were added N-(piperidin-4-yl)cyclopropanecarboxamide (12 mg), DIPEA (26 µL) and HATU (29 mg), and the mixture was stirred at room temperature for 1 h. The reaction mixture was purified by silica gel column chromatography to give the title compound (16 mg).

MS (m/z): 546 [M+H]$^+$

Example 53

Methyl(1-{[6-{[(1R)-1-(4-methoxyphenyl)ethyl]amino}-2-(pyrazolo[5,1-b][1,3]thiazol-7-yl)pyrimidin-4-yl]carbonyl}piperidin-4-yl)carbamate Analogous to the method in Example 52, the title compound was synthesized by using methyl piperidin-4-ylcarbamate obtained in Reference Example 14 Step 1 in place of N-(piperidin-4-yl)cyclopropanecarboxamide.

MS (m/z): 536 [M+H]$^+$

Example 54

N-(1-{[6-{[(1R)-1-(4-Methoxyphenyl)ethyl]amino}-2-(pyrazolo[5,1-b][1,3]thiazol-7-yl)pyrimidin-4-yl]carbonyl}piperidin-4-yl)benzamide Analogous to the method in Example 52, the title compound was synthesized by using N-(4-piperidyl)benzamide in place of N-(piperidin-4-yl)cyclopropanecarboxamide.
MS (m/z): 582 [M+H]$^+$

Example 55

N-(1-{[6-{[(2S)-1-Hydroxy-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide Analogous to the method in Example 48, the title compound was synthesized by using (2S)-2-amino-3,3-dimethylbutan-1-ol in place of 2-amino-2-methylpropan-1-ol.
MS (m/z): 512 [M+H]$^+$

Example 56

(4-Hydroxypiperidin-1-yl)[6-{[(1R)-1-(4-methoxyphenyl)ethyl]amino}-2-(pyrazolo[5,1-b][1,3]thiazol-7-yl)pyrimidin-4-yl]methanone Analogous to the method in Example 52, the title compound was synthesized by using piperidin-4-ol in place of N-(piperidin-4-yl)cyclopropanecarboxamide.
MS (m/z): 479 [M+H]$^+$

Example 57

1-Fluoro-2-methylpropan-2-yl(1-{[6-{[(1R)-1-(4-methoxyphenyl)ethyl]amino}-2-(pyrazolo[5,1-b][1,3]thiazol-7-yl)pyrimidin-4-yl]carbonyl}piperidin-4-yl)carbamate Analogous to the method in Example 52, the title compound was synthesized by using 1-fluoro-2-methylpropan-2-yl piperidin-4-ylcarbamate obtained in Reference Example 51 in place of N-(piperidin-4-yl)cyclopropanecarboxamide.
MS (m/z): 596 [M+H]$^+$

Example 58

[6-(tert-Butylamino)-2-(pyrazolo[5,1-b][1,3]thiazol-7-yl)pyrimidin-4-yl](4-hydroxypiperidin-1-yl)methanone To a solution of [6-chloro-2-(pyrazolo[5,1-b][1,3]thiazol-7-yl)pyrimidin-4-yl](4-hydroxypiperidin-1-yl)methanone obtained in Reference Example 29 (2.2 g) in tert-butanol (10 mL) was added tert-butylamine (1.3 g), and the mixture was stirred at 130° C. for 10 h in a sealed tube. The reaction solution was concentrated under reduced pressure, and the resulting residue was purified by silica gel column chromatography to give the title compound (2.1 g).
MS (m/z): 401 [M+H]$^+$

Example 59

Methyl(1-{[6-(tert-butylamino)-2-(pyrazolo[5,1-b][1,3]thiazol-7-yl)pyrimidin-4-yl]carbonyl}piperidin-4-yl)carbamate Analogous to the method in Example 24 Step 1, the title compound was synthesized by using tert-butylamine in place of (2R)-3-methylbutan-2-amine.
MS (m/z): 458 [M+H]$^+$

Example 60

Propan-2-yl(1-{[6-(tert-butylamino)-2-(pyrazolo[5,1-b][1,3]thiazol-7-yl)pyrimidin-4-yl]carbonyl}piperidin-4-yl)carbamate Analogous to the method in Example 29, the title compound was synthesized by using tert-butylamine in place of (2R)-3,3-dimethylbutan-2-amine.
MS (m/z): 486 [M+H]$^+$

Example 61

Methyl[1-({6-[(1-hydroxy-2-methylpropan-2-yl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using 2-amino-2-methylpropan-1-ol in place of (2R)-3-methylbutan-2-amine.
MS (m/z): 474 [M+H]$^+$

Example 62

[6-{[(2R)-3,3-Dimethylbutan-2-yl]amino}-2-(pyrazolo[5,1-b][1,3]thiazol-7-yl)pyrimidin-4-yl](4-hydroxypiperidin-1-yl)methanone hydrochloride

[Step 1] Preparation of [6-{[(2R)-3,3-dimethylbutan-2-yl]amino}-2-(pyrazolo[5,1-b][1,3]thiazol-7-yl)pyrimidin-4-yl](4-hydroxypiperidin-1-yl)methanone To a solution of [6-chloro-2-(pyrazolo[5,1-b][1,3]thiazol-7-yl)pyrimidin-4-yl](4-hydroxypiperidin-1-yl)methanone obtained in Reference Example 29 (5 g) in 2-propanol (50 mL) were added DIPEA (9.5 mL) and (2R)-3,3-dimethylbutan-2-amine (2.8 g), and the mixture was stirred at 100° C. overnight. The reaction solution was concentrated under reduced pressure, and the resulting residue was purified by silica gel column chromatography to give the title compound (6.0 g).
MS (m/z): 429 [M+H]$^+$

[Step 2] Preparation of [6-{[(2R)-3,3-dimethylbutan-2-yl]amino}-2-(pyrazolo[5,1-b][1,3]thiazol-7-yl)pyrimidin-4-yl](4-hydroxypiperidin-1-yl)methanone hydrochloride Analogous to the method in Example 27, the title compound was synthesized by using [6-{[(2R)-3,3-dimethylbutan-2-yl]amino}-2-(pyrazolo[5,1-b][1,3]thiazol-7-yl)pyrimidin-4-yl](4-hydroxypiperidin-1-yl)methanone obtained in Step 1.

MS (m/z): 429 [M−Cl]$^+$
Elemental analysis value (for $C_{21}H_{28}N_6O_2S \cdot HCl + 0.5H_2O$).
Calculated value (%) C: 52.22, H: 6.14, N: 18.27.
Found value (%) C: 52.09, H: 6.06, N: 18.26.

Example 63

Methyl(1-{[6-{[(2S)-1-hydroxy-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 24 Step 1, the title compound was synthesized by using (2S)-2-amino-3,3-dimethylbutan-1-ol in place of (2R)-3-methylbutan-2-amine.
MS (m/z): 502 [M+H]$^+$

Example 64

Methyl[1-({6-[(3,3-dimethylbutan-2-yl)oxy]-2-(pyrazolo[5,1-b][1,3]thiazol-7-yl)pyrimidin-4-yl}carbonyl)piperidin-4-yl]carbamate To a solution of methyl(1-{[6-chloro-2-(pyrazolo[5,1-b][1,3]thiazol-7-yl)pyrimidin-4-yl]carbonyl}piperidin-4-yl)carbamate obtained in Reference Example 14 (25 mg) and 3,3-dimethylbutan-2-ol (61 mg) in THF (2 mL) was added 60% sodium hydride (4 mg) under ice cooling, and the mixture was stirred at room temperature overnight. The reaction solution was diluted with ethyl acetate, separated by adding water, and the aqueous layer was further extracted with ethyl acetate. The combined organic layer was dried over anhydrous sodium sulfate, and concentrated under reduced pressure. The resulting residue was purified by silica gel column chromatography to give the title compound (6 mg).
MS (m/z): 487 [M+H]$^+$

Example 65

Methyl(1-{[6-(cyclobutyloxy)-2-(pyrazolo[5,1-b][1,3]thiazol-7-yl)pyrimidin-4-yl]carbonyl}piperidin-4-yl)carbamate Analogous to the method in Example 64, the title compound was synthesized by using cyclobutanol in place of 3,3-dimethylbutan-2-ol.
MS (m/z): 457 [M+H]$^+$

Example 66

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)methanesulfonamide Analogous to the method in Example 30 Step 3, the title compound was synthesized by using methanesulfonyl chloride in place of benzoyl chloride.
MS (m/z): 490 [M+H]$^+$

Example 67

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)cyclopropanesulfonamide Analogous to the method in Example 30 Step 3, the title compound was synthesized by using cyclopropanesulfonyl chloride in place of benzoyl chloride.
MS (m/z): 516 [M+H]$^+$

Example 68

N-(1-{[6-{[(1S)-1-Cyclopropylethyl]amino}-2-(pyrazolo[5,1-b][1,3]thiazol-7-yl)pyrimidin-4-yl]carbonyl}piperidin-4-yl)ethanesulfonamide Analogous to the method in Example 30 Step 3, the title compound was synthesized by using ethanesulfonyl chloride in place of benzoyl chloride.
MS (m/z): 504 [M+H]$^+$

Example 69

N-(1-{[6-(tert-Butylamino)-2-(pyrazolo[5,1-b][1,3]thiazol-7-yl)pyrimidin-4-yl]carbonyl}piperidin-4-yl)-2-methylpropanamide To a solution of methyl 6-(tert-butylamino)-2-(pyrazolo[5,1-b][1,3]thiazol-7-yl)pyrimidine-4-carboxylate obtained in Example 36 Step 1 (280 mg) in 1,4-dioxane (3 mL) was added 2 M sodium hydroxide aqueous solution (1.27 mL), and the mixture was stirred at 50° C. for 1 h. The mixture was neutralized with 2 M hydrochloric acid aqueous solution, and the reaction solution was concentrated under reduced pressure to give a solid (50 mg). To a solution of the obtained solid in DMF (0.3 mL) were added DIPEA (41 mg), 2-methyl-N-(4-piperidyl)propanamide (which was prepared analogous to the method described in, for example, Bioorganic and Medicinal Chemistry Letters, 2012, 22, 3157-3162) (52 mg) and HATU (87 mg), and the mixture was stirred at room temperature for 1 h. The reaction mixture was concentrated under reduced pressure, and the residue was diluted with chloroform and purified by silica gel column chromatography to give the title compound (28 mg).
MS (m/z): 470 [M+H]$^+$

Example 70

N-(1-{[6-(tert-Butylamino)-2-(pyrazolo[5,1-b][1,3]thiazol-7-yl)pyrimidin-4-yl]carbonyl}piperidin-4-yl)-2,2-difluoroacetamide Analogous to the method in Example 69, the title compound was synthesized by using 2,2-difluoro-N-(4-piperidyl)acetamide obtained in Example 28 Step 1 in place of 2-methyl-N-(4-piperidyl)propanamide.
MS (m/z): 478 [M+H]$^+$

Example 71

Ethyl(1-{[6-(tert-butylamino)-2-(pyrazolo[5,1-b][1,3]thiazol-7-yl)pyrimidin-4-yl]carbonyl}piperidin-4-yl)carbamate Analogous to the method in Example 69, the title compound was synthesized by using ethyl piperidin-4-ylcarbamate (which was prepared analogous to the method described in, for example, U.S. Pat. No. 4,918,073) in place of 2-methyl-N-(4-piperidyl)propanamide.
MS (m/z): 472 [M+H]$^+$

Example 72

[6-(tert-Butylamino)-2-(pyrazolo[5,1-b][1,3]thiazol-7-yl)pyrimidin-4-yl][4-(pyridin-2-ylamino)piperidin-1-yl]methanone To a solution of [6-chloro-2-(pyrazolo[5,1-b][1,3]thiazol-7-yl)pyrimidin-4-yl][4-(pyridin-2-ylamino)piperidin-1-yl]methanone obtained in Reference Example 18 (25 mg) in NMP (0.5 mL) were added DIPEA (20 μL) and tert-butylamine (8 mg), and the mixture was stirred at 120° C. for 2 h. An additional tert-butylamine (8 mg) was added thereto, and the mixture was stirred at 120° C. for an additional hour. The reaction mixture was purified by silica gel column chromatography to give the title compound (8 mg).

MS (m/z): 477 [M+H]$^+$

Example 73

Ethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate To a solution of 6-{[(1R)-1-cyclopropylethyl]amino}-2-(pyrazolo[5,1-b][1,3]thiazol-7-yl)pyrimidine-4-carboxylic acid obtained in Reference Example 39 (50 mg) in DMF (0.3 mL) were added ethyl piperidin-4-ylcarbamate (which was prepared analogous to the method described in, for example, U.S. Pat. No. 4,918,073) (52 mg), DIPEA (59 mg) and HATU (87 mg), and the mixture was stirred at room temperature for 3 h. The reaction mixture was concentrated under reduced pressure, and the resulting residue was purified by silica gel column chromatography to give the title compound (30 mg).

MS (m/z): 484 [M+H]$^+$

Example 74

Ethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate hydrochloride Analogous to the method in Example 27, the title compound was synthesized by using ethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate obtained in Example 73.

MS (m/z): 484 [M−Cl]$^+$

Elemental analysis value (for $C_{23}H_{29}N_7O_3S \cdot HCl + 1.1H_2O$).

Calculated value (%) C: 51.17, H: 6.01, N: 18.16.
Found value (%) C: 50.92, H: 6.12, N: 17.95.

Example 75

[6-(tert-Butylamino)-2-(pyrazolo[5,1-b][1,3]thiazol-7-yl)pyrimidin-4-yl][4-(1,3-thiazol-2-ylamino)piperidin-1-yl]methanone Analogous to the method in Example 72, the title compound was synthesized by using [6-chloro-2-(pyrazolo[5,1-b][1,3]thiazol-7-yl)pyrimidin-4-yl][4-(1,3-thiazol-2-ylamino)piperidin-1-yl]methanone obtained in Reference Example 19 in place of [6-chloro-2-(pyrazolo[5,1-b][1,3]thiazol-7-yl)pyrimidin-4-yl][4-(pyridin-2-ylamino)piperidin-1-yl]methanone.

MS (m/z): 483 [M+H]$^+$

Example 76

[6-(tert-Butylamino)-2-(pyrazolo[5,1-b][1,3]thiazol-7-yl)pyrimidin-4-yl][4-(pyrimidin-2-ylamino)piperidin-1-yl]methanone Analogous to the method in Example 72, the title compound was synthesized by using [6-chloro-2-(pyrazolo[5,1-b][1,3]thiazol-7-yl)pyrimidin-4-yl][4-(pyrimidin-2-ylamino)piperidin-1-yl]methanone obtained in Reference Example 20 in place of [6-chloro-2-(pyrazolo[5,1-b][1,3]thiazol-7-yl)pyrimidin-4-yl][4-(pyridin-2-ylamino)piperidin-1-yl]methanone.

MS (m/z): 478 [M+H]$^+$

Example 77

Methyl(1-{[6-{[(1R)-1-(4-fluorophenyl)ethyl]amino}-2-(pyrazolo[5,1-b][1,3]thiazol-7-yl)pyrimidin-4-yl]carbonyl}piperidin-4-yl)carbamate Under argon atmosphere, to a solution of methyl(1-{[6-chloro-2-(pyrazolo[5,1-b][1,3]thiazol-7-yl)pyrimidin-4-yl]carbonyl}piperidin-4-yl)carbamate obtained in Reference Example 14 (20 mg) in DMF (1 mL) were added DIPEA (25 μL) and (1R)-1-(4-fluorophenyl)ethanamine (18 μL), and the mixture was stirred at 80° C. for 4 h. The reaction solution was diluted with ethyl acetate, separated by adding saturated aqueous sodium bicarbonate solution, and the aqueous layer was further extracted with ethyl acetate. The combined organic layer was washed with saturated aqueous sodium bicarbonate solution, dried over anhydrous magnesium sulfate, and concentrated under reduced pressure. The resulting residue was purified by silica gel column chromatography to give the title compound (24 mg).

MS (m/z): 524 [M+H]$^+$

Example 78

N-[1-({6-[(Azetidin-3-ylmethyl)amino]-2-(pyrazolo[5,1-b][1,3]thiazol-7-yl)pyrimidin-4-yl}carbonyl)piperidin-4-yl]cyclopropanecarboxamide To a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (30 mg) in DMF (1 mL) were added DIPEA (48 μL) and 3-(aminomethyl)azetidine-1-carboxylic acid tert-butyl(19 mg), and the mixture was stirred at 120° C. for 2 h. The reaction solution was diluted with ethyl acetate, separated by adding saturated aqueous sodium bicarbonate solution, and the aqueous layer was further extracted with ethyl acetate. The combined organic layer was washed with saturated aqueous sodium bicarbonate solution, dried over anhydrous magnesium sulfate, and concentrated under reduced pressure. The resulting residue was purified by silica gel column chromatography to give a solid (40 mg). To a solution of the obtained solid (35 mg) in dichloromethane (1 mL) was added TFA (1 mL), and the mixture was stirred at room temperature for 1 h. The reaction mixture was purified by silica gel column chromatography to give the title compound (29 mg).
MS (m/z): 481 [M+H]$^+$

Example 79

N-(1-{[6-{[(1R)-1-(4-Fluorophenyl)ethyl]amino}-2-(pyrazolo[5,1-b][1,3]thiazol-7-yl)pyrimidin-4-yl]carbonyl}piperidin-4-yl)-2-methylpropanamide Analogous to the method in Example 77, the title compound was synthesized by using N-(1-{[6-chloro-2-(pyrazolo[5,1-b][1,3]thiazol-7-yl)pyrimidin-4-yl]carbonyl}piperidin-4-yl)-2-methylpropanamide obtained in Reference Example 16 in place of methyl(1-{[6-chloro-2-(pyrazolo[5,1-b][1,3]thiazol-7-yl)pyrimidin-4-yl]carbonyl}piperidin-4-yl)carbamate.
MS (m/z): 536 [M+H]$^+$

Example 80

Methyl[1-({6-[(2-methylbutan-2-yl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using 2-methylbutan-2-amine in place of (2R)-3-methylbutan-2-amine.
MS (m/z): 472 [M+H]$^+$

Example 81

(4-Hydroxypiperidin-1-yl)[6-(pentan-3-ylamino)-2-(pyrazolo[5,1-b][1,3]thiazol-7-yl)pyrimidin-4-yl]methanone hydrochloride

[Step 1] Preparation of (4-hydroxypiperidin-1-yl)[6-(pentan-3-ylamino)-2-(pyrazolo[5,1-b][1,3]thiazol-7-yl)pyrimidin-4-yl]methanone To a solution of (4-{[tert-butyl(dimethyl)silyl]oxy}piperidin-1-yl)[6-chloro-2-(pyrazolo[5,1-b][1,3]thiazol-7-yl)pyrimidin-4-yl]methanone obtained in Reference Example 30 (840 mg) in 1-butanol (10 mL) were added DIPEA (1.2 mL) and pentan-3-amine (459 mg), and the mixture was stirred at 80° C. for 4 h. The reaction solution was concentrated under reduced pressure, and the resulting residue was purified by silica gel column chromatography to give a solid (792 mg). To a solution of the obtained solid (790 mg) in THF (5 mL) was added 1 M tetrabutylammonium fluoride (THF solution, 6.0 mL), and the mixture was stirred at room temperature for 3 h. To the reaction solution was added saturated aqueous ammonium chloride solution, the solution was extracted with chloroform, and the organic layer was dried over anhydrous magnesium sulfate, and concentrated under reduced pressure. The resulting residue was purified by silica gel column chromatography to give the title compound (474 mg).
MS (m/z): 415 [M+H]$^+$

[Step 2] Preparation of (4-hydroxypiperidin-1-yl)[6-(pentan-3-ylamino)-2-(pyrazolo[5,1-b][1,3]thiazol-7-yl)pyrimidin-4-yl]methanone hydrochloride To a solution of (4-hydroxypiperidin-1-yl)[6-(pentan-3-ylamino)-2-(pyrazolo[5,1-b][1,3]thiazol-7-yl)pyrimidin-4-yl]methanone obtained in Step 1 (474 mg) in ethyl acetate (10 mL) was added 4 M hydrogen chloride-ethyl acetate solution (0.57 mL). The reaction solution was concentrated under reduced pressure to give the title compound (517 mg).
MS (m/z): 415 [M−Cl]$^+$
Elemental analysis value (for $C_{20}H_{26}N_6O_2S.HCl+0.5H_2O$).
Calculated value (%) C: 52.22, H: 6.14, N: 18.27.
Found value (%) C: 52.09, H: 6.06, N: 18.26.

Example 82

Propyl(1-{[6-(tert-butylamino)-2-(pyrazolo[5,1-b][1,3]thiazol-7-yl)pyrimidin-4-yl]carbonyl}piperidin-4-yl)carbamate Propyl(1-{[6-chloro-2-(pyrazolo[5,1-b][1,3]thiazol-7-yl)pyrimidin-4-yl]carbonyl}piperidin-4-yl)carbamate obtained in Reference Example 23 (30 mg) was dissolved in NMP (0.5 mL), to the mixture were added DIPEA (17 mg) and tert-butylamine (14 mg), and the mixture was stirred at 130° C. for 3 h in a sealed tube. The reaction solution was concentrated under reduced pressure, and the resulting residue was purified by silica gel column chromatography to give the title compound (25 mg).
MS (m/z): 486 [M+H]$^+$

Example 83

Propyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 82, the title compound was synthesized by using (1R)-1-cyclopropylethanamine in place of tert-butylamine.
MS (m/z): 498 [M+H]$^+$

Example 84

Propyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 82, the title compound was synthesized by using (1S)-1-cyclopropylethanamine in place of .tert-butylamine
MS (m/z): 498 [M+H]$^+$

Example 85

Propyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 82, the title compound was synthesized by using (2R)-3,3-dimethylbutan-2-amine in place of tert-butylamine.
MS (m/z): 514 [M+H]$^+$

Example 86

Propyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 82, the title compound was synthesized by using (2S)-3,3-dimethylbutan-2-amine in place of tert-butylamine.
MS (m/z): 514 [M+H]$^+$

Example 87

Methyl[1-({6-[(2,2-dimethylpropyl)amino]-2-(pyrazolo[5,1-b][1,3]thiazol-7-yl)pyrimidin-4-yl}carbonyl)piperidin-4-yl]carbamate hydrochloride

[Step 1] Preparation of methyl[1-({6-[(2,2-dimethylpropyl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using 2,2-dimethylpropan-1-amine in place of (2R)-3-methylbutan-2-amine.
MS (m/z): 472 [M+H]$^+$

[Step 2] Preparation of methyl[1-({6-[(2,2-dimethylpropyl)amino]-2-(pyrazolo[5,1-b][1,3]thiazol-7-yl)pyrimidin-4-yl}carbonyl)piperidin-4-yl]carbamate hydrochloride To a solution of methyl[1-({6-[(2,2-dimethylpropyl)amino]-2-(pyrazolo[5,1-b][1,3]thiazol-7-yl)pyrimidin-4-yl}carbonyl)piperidin-4-yl]carbamate obtained in Step 1 (48 mg) in ethyl acetate (3 mL) was added 4 M hydrogen chloride-ethyl acetate solution (50 µL). The reaction solution was concentrated under reduced pressure, and dried to give the title compound (51 mg).
MS (m/z): 472 [M–Cl]$^+$
Elemental analysis value (for $C_{22}H_{29}N_7O_3S \cdot HCl + 1.6H_2O$).
Calculated value (%) C: 49.22, H: 6.23, N: 18.26.
Found value (%) C: 49.03, H: 6.03, N: 18.35.

Example 88

2-Methoxyethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate To a solution of 2-methoxyethyl(1-{[6-chloro-2-(pyrazolo[5,1-b][1,3]thiazol-7-yl)pyrimidin-4-yl]carbonyl}piperidin-4-yl)carbamate obtained in Reference Example 24 (20 mg) in ethanol (1 mL) were added DIPEA (30 µL) and (1R)-1-cyclopropylethanamine (14 µL), and the mixture was stirred at 80° C. overnight. The reaction mixture was purified by silica gel column chromatography to give the title compound (15 mg).
MS (m/z): 514 [M+H]$^+$

Example 89

2-Methoxyethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 88, the title compound was synthesized by using (1S)-1-cyclopropylethanamine in place of (1R)-1-cyclopropylethanamine.
MS (m/z): 514 [M+H]$^+$

Example 90

2-Methoxyethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 88, the title compound was synthesized by using (2R)-3,3-dimethylbutan-2-amine in place of (1R)-1-cyclopropylethanamine.
MS (m/z): 530 [M+H]$^+$

Example 91

2-Methoxyethyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 88, the title compound was synthesized by using (2S)-3,3-dimethylbutan-2-amine in place of (1R)-1-cyclopropylethanamine.
MS (m/z): 530 [M+H]$^+$

Example 92

N-(1-{[6-{[(1R)-1-Cyclopropylethyl]amino}-2-(pyrazolo[5,1-b][1,3]thiazol-7-yl)pyrimidin-4-yl]carbonyl}piperidin-4-yl)-2-methoxyacetamide To a solution of N-(1-{[6-chloro-2-(pyrazolo[5,1-b][1,3]thiazol-7-yl)pyrimidin-4-yl]carbonyl}piperidin-4-yl)-2-methoxyacetamide obtained in Reference Example 27 (50 mg) in 2-propanol (1 mL) were added DIPEA (60 µL) and (1R)-1-cyclopropylethanamine (49 mg), and the mixture was stirred at 90° C. for 3 h. The reaction solution was concentrated under reduced pressure, and the resulting residue was purified by silica gel column chromatography to give the title compound (42 mg).
MS (m/z): 484 [M+H]$^+$

Example 93

N-(1-{[6-{[(2R)-3,3-Dimethylbutan-2-yl]amino}-2-(pyrazolo[5,1-b][1,3]thiazol-7-yl)pyrimidin-4-yl]carbonyl}piperidin-4-yl)-2-methoxyacetamide Analogous to the method in Example 92, the title compound was synthesized by using (2R)-3,3-dimethylbutan-2-amine in place of (1R)-1-cyclopropylethanamine.
MS (m/z): 500 [M+H]$^+$

Example 94

{6-[(2,2-Dimethylpropyl)amino]-2-(pyrazolo[5,1-b][1,3]thiazol-7-yl)pyrimidin-4-yl}(4-hydroxypiperidin-1-yl)methanone To a solution of 6-[(2,2-dimethylpropyl)amino]-2-(pyrazolo[5,1-b][1,3]thiazol-7-yl)pyrimidine-4-carboxylic acid obtained in Reference Example 49 (27 mg) in DMF (0.5 mL) were added piperidin-4-ol (16 mg), DIPEA (28 µL) and HATU (62 mg), and the mixture was stirred at room temperature overnight. Then, HATU (15 mg) was added thereto, and the mixture was stirred at room temperature for 3 h. The reaction mixture was purified by silica gel column chromatography to give the title compound (16 mg).
MS (m/z): 415 [M+H]$^+$

Example 95

Methyl[1-({6-[{[1-(methoxymethyl)cyclopropyl]methyl}(methyl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using 1-(1-(methoxymethyl)

cyclopropyl)-N-methylmethanamine hydrochloride obtained in Reference Example 13 in place of (2R)-3-methylbutan-2-amine.

MS (m/z): 514 [M+H]+

Example 96

2,2-Difluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate hydrochloride

[Step 1] Preparation of 2,2-difluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate To a solution of 2,2-difluoroethyl(1-{[6-chloro-2-(pyrazolo[5,1-b][1,3]thiazol-7-yl)pyrimidin-4-yl]carbonyl}piperidin-4-yl)carbamate obtained in Reference Example 25 (20 mg) in ethanol (1 mL) were added DIPEA (29 μL) and (1R)-1-cyclopropylethanamine (14 μL), and the mixture was stirred at 80° C. overnight. The reaction mixture was purified by silica gel column chromatography to give the title compound (14 mg).

MS (m/z): 520 [M+H]+

[Step 2] Preparation of 2,2-difluoroethyl(1-{[(6-{[(1R)-1-cyclopropylethyl]amino}-2-(pyrazolo[5,1-b][1,3]thiazol-7-yl)pyrimidin-4-yl]carbonyl}piperidin-4-yl)carbamate hydrochloride To a solution of 2,2-difluoroethyl(1-{[6-{[(1R)-1-cyclopropylethyl]amino}-2-(pyrazolo[5,1-b][1,3]thiazol-7-yl)pyrimidin-4-yl]carbonyl}piperidin-4-yl)carbamate obtained in Step 1 (490 mg) in ethyl acetate was added 4 M hydrogen chloride-ethyl acetate solution (0.47 mL). The reaction solution was concentrated under reduced pressure, and the resulting residue was washed with diethyl ether to give the title compound (455 mg).

MS (m/z): 520 [M−Cl]+

Elemental analysis value (for $C_{23}H_{27}F_2N_7O_3S \cdot HCl + 2.5H_2O$).

Calculated value (%) C: 45.96, H: 5.53, N: 16.31.

Found value (%) C: 46.19, H: 5.34, N: 16.08.

Example 97

2,2-Difluoroethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate hydrochloride Analogous to the method in Example 96 Steps 1 and 2, the title compound was synthesized by using (2R)-3,3-dimethylbutan-2-amine in place of (1R)-1-cyclopropylethanamine.

MS (m/z): 536 [M−Cl]+

Elemental analysis value (for $C_{24}H_{31}F_2N_7O_3S \cdot HCl + 1.1H_2O$).

Calculated value (%) C: 48.70, H: 5.82, N: 16.56.

Found value (%) C: 48.50, H: 5.69, N: 16.49.

Example 98

2,2-Difluoroethyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Analogous to the method in Example 96 Step 1, the title compound was synthesized by using (1S)-1-cyclopropylethanamine in place of (1R)-1-cyclopropylethanamine.

MS (m/z): 520 [M+H]+

Example 99

2,2-Difluoroethyl(1-{[6-{[(2S)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 96 Step 1, the title compound was synthesized by using (2S)-3,3-dimethylbutan-2-amine in place of (1R)-1-cyclopropylethanamine.

MS (m/z): 536 [M+H]+

Example 100 tert-Butyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate To a solution of tert-butyl(1-{[6-chloro-2-(pyrazolo[5,1-b][1,3]thiazol-7-yl)pyrimidin-4-yl]carbonyl}piperidin-4-yl)carbamate obtained in Reference Example 17 (200 mg) in 1-butanol (1 mL) were added (2R)-3,3-dimethylbutan-2-amine (131 mg) and DIPEA (0.3 mL), and the mixture was stirred at 80° C. for 4 h. The reaction solution was concentrated under reduced pressure, and the resulting residue was purified by silica gel column chromatography to give the title compound (183 mg).

MS (m/z): 528 [M+H]+

Example 101

2-Methoxyethyl(1-{[6-(tert-butylamino)-2-(pyrazolo[5,1-b][1,3]thiazol-7-yl)pyrimidin-4-yl]carbonyl}piperidin-4-yl)carbamate To a solution of 2-methoxyethyl(1-{[6-chloro-2-(pyrazolo[5,1-b][1,3]thiazol-7-yl)pyrimidin-4-yl]carbonyl}piperidin-4-yl)carbamate obtained in Reference Example 24 (20 mg) in ethanol (0.5 mL) were added DIPEA (45 μL) and tert-butylamine (23 μL), and the mixture was stirred at 130° C. for 4 h in a sealed tube. The reaction mixture was purified by silica gel column chromatography to give the title compound (2.4 mg).

MS (m/z): 502 [M+H]+

Example 102

2-(Dimethylamino)ethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 40, the title compound was synthesized by using 2-(dimethylamino)ethyl piperidin-4-ylcarbamate obtained in Reference Example 52 in place of ethyl piperidin-4-ylcarbamate.
MS (m/z): 543 [M+H]⁺

Example 103

2,2,2-Trifluoroethyl(1-{[6-{[(1R)-1-cyclopropyl-ethyl]amino}-2-(pyrazolo[5,1-b][1,3]thiazol-7-yl)pyrimidin-4-yl]carbonyl}piperidin-4-yl)carbamate To a solution of 2,2,2-trifluoroethyl(1-{[6-chloro-2-(pyrazolo[5,1-b][1,3]thiazol-7-yl)pyrimidin-4-yl]carbonyl}piperidin-4-yl)carbamate obtained in Reference Example 26 (15 mg) in DMF (1 mL) were added DIPEA (21 µL) and (1R)-1-cyclopropylethanamine (10 µL), and the mixture was stirred at 90° C. for 3 h. The reaction mixture was purified by silica gel column chromatography to give the title compound (5 mg).
MS (m/z): 538 [M+H]⁺

Example 104

2,2,2-Trifluoroethyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate Analogous to the method in Example 103, the title compound was synthesized by using (2R)-3,3-dimethylbutan-2-amine in place of (1R)-1-cyclopropylethanamine.
MS (m/z): 554 [M+H]⁺

Example 105

N-(1-{[6-(Cyclopentyloxy)-2-(pyrazolo[5,1-b][1,3]thiazol-7-yl)pyrimidin-4-yl]carbonyl}piperidin-4-yl)cyclopropanecarboxamide Analogous to the method in Example 43, the title compound was synthesized by using cyclopentanol in place of cyclopropylmethanol.
MS (m/z): 481 [M+H]⁺

Example 106

2-Methoxy-N-(1-{[6-(pentan-3-ylamino)-2-(pyrazolo[5,1-b][1,3]thiazol-7-yl)pyrimidin-4-yl]carbonyl}piperidin-4-yl)acetamide Analogous to the method in Example 92, the title compound was synthesized by using pentan-3-amine in place of (1R)-1-cyclopropylethanamine.
MS (m/z): 486 [M+H]⁺

Example 107

N-(1-{[6-(2-Ethylbutoxy)-2-(pyrazolo[5,1-b][1,3]thiazol-7-yl)pyrimidin-4-yl]carbonyl}piperidin-4-yl)cyclopropanecarboxamide Under argon atmosphere, to a suspension of 60% sodium hydride (4 mg) in THF (1.0 mL) were added 2-ethylbutan-1-ol (29 µL) and N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (20 mg) in this sequence, and the mixture was stirred at room temperature overnight. To the reaction mixture was added water, the solution was extracted with ethyl acetate, and the organic layer was washed with saturated aqueous sodium bicarbonate solution, dried over anhydrous magnesium sulfate, and concentrated under reduced pressure. The resulting residue was purified by silica gel column chromatography to give the title compound (16 mg).
MS (m/z): 496 [M+H]⁺

Example 108

Methyl(1-{[6-(pentan-3-yloxy)-2-(pyrazolo[5,1-b][1,3]thiazol-7-yl)pyrimidin-4-yl]carbonyl}piperidin-4-yl)carbamate Under argon atmosphere, to a suspension of 60% sodium hydride (4 mg) in THF (1 mL) were added pentan-3-ol (29 µL) and methyl(1-{[6-chloro-2-(pyrazolo[5,1-b][1,3]thiazol-7-yl)pyrimidin-4-yl]carbonyl}piperidin-4-yl)carbamate obtained in Reference Example 14 (20 mg) in this sequence, and the mixture was stirred at room temperature for 3 h. An additional 60% sodium hydride (4 mg) was added thereto, and the mixture was stirred further at room temperature overnight. To the reaction mixture was added water, and the solution was extracted with ethyl acetate. The organic layer was washed with saturated aqueous sodium bicarbonate solution, dried over anhydrous magnesium sulfate, and concentrated under reduced pressure. The resulting residue was purified by silica gel column chromatography to give the title compound (15 mg).
MS (m/z): 473 [M+H]⁺

Example 109

Methyl(1-{[6-(pentan-3-ylamino)-2-(pyrazolo[5,1-b][1,3]thiazol-7-yl)pyrimidin-4-yl]carbonyl}piperidin-4-yl)carbamate Analogous to the method in Example 24 Step 1, the title compound was synthesized by using pentan-3-amine in place of (2R)-3-methylbutan-2-amine.
MS (m/z): 472 [M+H]⁺

Example 110

N-[1-({6-[(2-Ethylbutyl)amino]-2-(pyrazolo[5,1-b][1,3]thiazol-7-yl)pyrimidin-4-yl}carbonyl)piperidin-4-yl]cyclopropanecarboxamide Analogous to the method in Example 16, the title compound was synthesized by using 2-ethylbutan-1-amine in place of (2R)-3,3-dimethylbutan-2-amine.
MS (m/z): 496 [M+H]⁺

Example 111

N-(1-{[6-(Pentan-3-yloxy)-2-(pyrazolo[5,1-b][1,3]thiazol-7-yl)pyrimidin-4-yl]carbonyl}piperidin-4-yl)cyclopropanecarboxamide Analogous to the method in Example 107, the title compound was synthesized by using pentan-3-ol in place of 2-ethylbutan-1-ol.
MS (m/z): 483 [M+H]⁺

Example 112

Methyl[1-({6-[methyl(pentan-3-yl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using N-methylpentan-3-amine hydrochloride in place of (2R)-3-methylbutan-2-amine.

MS (m/z): 486 [M+H]$^+$

Example 113

Methyl(1-{[6-{[(2R)-3,3-dimethylbutan-2-yl](methyl)amino}-2-(pyrazolo[5,1-b][1,3]thiazol-7-yl)pyrimidin-4-yl]carbonyl}piperidin-4-yl)carbamate Analogous to the method in Example 24, the title compound was synthesized by using (2R)—N,3,3-trimethylbutan-2-amine hydrochloride obtained in Reference Example 12 in place of (2R)-3-methylbutan-2-amine.

MS (m/z): 500 [M+H]$^+$

Example 114

N-(1-{[6-(2-Ethylbutoxy)-2-(pyrazolo[5,1-b][1,3]thiazol-7-yl)pyrimidin-4-yl]carbonyl}piperidin-4-yl)propanamide Under argon atmosphere, to a suspension of 60% sodium hydride (8.0 mg) in THF (1.0 mL) was added 2-ethylbutan-1-ol (49 mg) under ice cooling, and the mixture was stirred at room temperature for 5 min. Then, N-(1-{[6-chloro-2-(pyrazolo[5,1-b][1,3]thiazol-7-yl)pyrimidin-4-yl]carbonyl}piperidin-4-yl)propanamide obtained in Reference Example 31 (40 mg) was added thereto, and the mixture was stirred at room temperature overnight. To the reaction mixture was added water, and the solution was separated by ethyl acetate. The organic layer was washed with saturated aqueous sodium bicarbonate solution, dried over anhydrous magnesium sulfate, and concentrated under reduced pressure. The resulting residue was purified by silica gel column chromatography to give the title compound (33 mg).

MS (m/z): 485 [M+H]$^+$

Example 115

N-(1-{[6-{[(2R)-3,3-Dimethylbutan-2-yl](methyl)amino}-2-(pyrazolo[5,1-b][1,3]thiazol-7-yl)pyrimidin-4-yl]carbonyl}piperidin-4-yl)propanamide To a solution of N-(1-{[6-chloro-2-(pyrazolo[5,1-b][1,3]thiazol-7-yl)pyrimidin-4-yl]carbonyl}piperidin-4-yl)propanamide obtained in Reference Example 31 (20 mg) in 1-butanol (1 mL) were added DIPEA (50 µL) and (2R)—N,3,3-trimethylbutan-2-amine hydrochloride obtained in Reference Example 12 (14 mg), and the mixture was stirred at 80° C. for 7 h. The reaction mixture was purified by silica gel column chromatography to give the title compound (9 mg).

MS (m/z): 498 [M+H]$^+$

Example 116

N-[1-({6-[Methyl(pentan-3-yl)amino]-2-(pyrazolo[5,1-b][1,3]thiazol-7-yl)pyrimidin-4-yl}carbonyl)piperidin-4-yl]propanamide Analogous to the method in Example 115, the title compound was synthesized by using N-methylpentan-3-amine hydrochloride in place of (2R)—N,3,3-trimethylbutan-2-amine hydrochloride.

MS (m/z): 484 [M+H]$^+$

Example 117

1-({6-[(4-Hydroxypiperidin-1-yl)carbonyl]-2-(pyrazolo[5,1-b][1,3]thiazol-7-yl)pyrimidin-4-yl}amino)cyclopropanecarbonitrile hydrochloride To a solution of [6-chloro-2-(pyrazolo[5,1-b][1,3]thiazol-7-yl)pyrimidin-4-yl](4-hydroxypiperidin-1-yl)methanone obtained in Reference Example 29 (20 mg) in ethanol (0.2 mL) were added DIPEA (12 µL) and 1-aminocyclopropanecarbonitrile hydrochloride (65 mg), and the mixture was reacted in a microwave reactor at 130° C. for 1 h. The reaction mixture was purified by silica gel column chromatography to give a solid (16 mg). To a solution of the obtained solid (16 mg) in ethyl acetate (0.5 mL) was added 4 M hydrogen chloride-ethyl acetate solution (16 µL), and the solvent was distilled off under reduced pressure. The residue was triturated with ethyl acetate and hexane, and the powder was collected on a filter, and dried to give the title compound (12 mg).

MS (m/z): 410 [M−Cl]$^+$

Example 118

[6-{[(2R)-3,3-Dimethylbutan-2-yl]amino}-2-(pyrazolo[5,1-b][1,3]thiazol-7-yl)pyrimidin-4-yl]{4-[(3-fluoropyridin-2-yl)amino]piperidin-1-yl}methanone To a solution of [6-chloro-2-(pyrazolo[5,1-b][1,3]thiazol-7-yl)pyrimidin-4-yl](4-[(3-fluoropyridin-2-yl)amino]piperidin-1-yl)methanone obtained in Reference Example 32 (10 mg) in 1-butanol (1 mL) were added DIPEA (15 µL) and (2R)-3,3-dimethylbutan-2-amine (7 mg), and the mixture was stirred at 80° C. for 5 h. The reaction solution was concentrated under reduced pressure, and the resulting residue was purified by silica gel column chromatography to give the title compound (11 mg).

MS (m/z): 523 [M+H]$^+$

Example 119

N-[1-({6-[(2-Methoxy-2-methylpropyl)amino]-2-(pyrazolo[5,1-b][1,3]thiazol-7-yl)pyrimidin-4-yl}carbonyl)piperidin-4-yl]propanamide Analogous to the method in Example 115, the title compound was synthesized by using 2-methoxy-2-methylpropan-1-amine in place of (2R)—N,3,3-trimethylbutan-2-amine hydrochloride.

MS (m/z): 486 [M+H]$^+$

Example 120

(4-Hydroxypiperidin-1-yl){6-[methyl(pentan-3-yl)amino]-2-(pyrazolo[5,1-b][1,3]thiazol-7-yl)pyrimidin-4-yl}methanone hydrochloride Analogous to the method in Example 117, the title compound was synthesized by using N-methylpentan-3-amine hydrochloride in place of 1-amino-cyclopropanecarbonitrile hydrochloride.
MS (m/z): 429 [M−Cl]$^+$

Example 121

N-(1-{[6-{[(2R)-3-Methylbutan-2-yl]amino}-2-(pyrazolo[5,1-b][1,3]thiazol-7-yl)pyrimidin-4-yl]carbonyl}piperidin-4-yl)propanamide Analogous to the method in Example 115, the title compound was synthesized by using (2R)-3-methylbutan-2-amine in place of (2R)—N,3,3-trimethylbutan-2-amine hydrochloride.
MS (m/z): 470 [M+H])

Example 122

N-(1-{[6-{[(2R)-3-Methylbutan-2-yl]amino}-2-(pyrazolo[5,1-b][1,3]thiazol-7-yl)pyrimidin-4-yl]carbonyl}piperidin-4-yl)cyclopropanecarboxamide Analogous to the method in Example 16, the title compound was synthesized by using (2R)-3-methylbutan-2-amine in place of (2R)-3,3-dimethylbutan-2-amine.
MS (m/z): 482 [M+H]$^+$

Example 123

N-(1-{[6-{[(2S)-3-Methylbutan-2-yl]amino}-2-(pyrazolo[5,1-b][1,3]thiazol-7-yl)pyrimidin-4-yl]carbonyl}piperidin-4-yl)cyclopropanecarboxamide Analogous to the method in Example 16, the title compound was synthesized by using (2S)-3-methylbutan-2-amine in place of (2R)-3,3-dimethylbutan-2-amine.
MS (m/z): 482 [M+H]$^+$

Example 124

N-(1-{[6-(Pentan-3-ylamino)-2-(pyrazolo[5,1-b][1,3]thiazol-7-yl)pyrimidin-4-yl]carbonyl}piperidin-4-yl)cyclopropanecarboxamide Analogous to the method in Example 16, the title compound was synthesized by using pentan-3-amine in place of (2R)-3,3-dimethylbutan-2-amine.
MS (m/z): 482 [M+H]$^+$

Example 125

Methyl[1-({6-[(2S)-butan-2-ylamino]-2-(pyrazolo[5,1-b][1,3]thiazol-7-yl)pyrimidin-4-yl}carbonyl)piperidin-4-yl]carbamate hydrochloride Analogous to the method in Example 24 Steps 1 and 2, the title compound was synthesized by using (2S)-butan-2-amine in place of (2R)-3-methylbutan-2-amine.
MS (m/z): 458 [M−Cl]$^+$
Elemental analysis value (for $C_{21}H_{27}N_7O_3S \cdot HCl$).
Calculated value (%) C: 51.06, H: 5.71, N: 19.85.
Found value (%) C: 51.00, H: 5.73, N: 19.74. Specific rotation$[\alpha]^D_{25}$=2.2° (c=2.00, DMSO).

Example 126

Methyl[1-({6-[(2R)-butan-2-ylamino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using (2R)-butan-2-amine in place of (2R)-3-methylbutan-2-amine.
MS (m/z): 458 [M−H]$^+$

Example 127

Methyl[1-({6-[(2R)-butan-2-ylamino]-2-(pyrazolo[5,1-b][1,3]thiazol-7-yl)pyrimidin-4-yl}carbonyl)piperidin-4-yl]carbamate hydrochloride Analogous to the method in Example 24 Step 2, the title compound was synthesized by using methyl[1-({6-[(2R)-butan-2-ylamino]-2-(pyrazolo[5,1-b][1,3]thiazol-7-yl)pyrimidin-4-yl}carbonyl)piperidin-4-yl]carbamate obtained in Example 126 in place of methyl(1-{[6-{[(2R)-3-methylbutan-2-yl]amino}-2-(pyrazolo[5,1-b][1,3]thiazol-7-yl)pyrimidin-4-yl]carbonyl}piperidin-4-yl)carbamate.
MS (m/z): 458 [M−Cl]
Elemental analysis value (for $C_{21}H_{27}N_7O_3S \cdot HCl + 0.7H_2O$).
Calculated value (%) C: 49.79, H: 5.85, N: 19.35.
Found value (%) C: 49.73, H: 5.75, N: 19.44. Specific rotation$[\alpha]^D_{25}$=−1.8° (c=2.00, DMSO).

Example 128

N-[1-({6-[(1-Methylcyclopropyl)amino]-2-(pyrazolo[5,1-b][1,3]thiazol-7-yl)pyrimidin-4-yl}carbonyl)piperidin-4-yl]propanamide Analogous to the method in Example 115, the title compound was synthesized by using 1-methylcyclopropanamine hydrochloride (which was prepared analogous to the method described in, for example, Chemische Berichte, 1986, 119, 3672-3693) in place of (2R)—N,3,3-trimethylbutan-2-amine hydrochloride.
MS (m/z): 454 [M+H]$^+$

Example 129

[6-{[(2R)-3,3-Dimethylbutan-2-yl]amino}-2-(pyrazolo[5,1-b][1,3]thiazol-7-yl)pyrimidin-4-yl]{4-[(5-fluoropyridin-2-yl)amino]piperidin-1-yl}methanone Analogous to the method in Example 118, the title compound was synthesized by using [6-chloro-2-(pyrazolo[5,1-b][1,3]thiazol-7-yl)pyrimidin-4-yl]{4-[(5-fluoropyridin-2-yl)amino]piperidin-1-yl}methanone obtained in Reference Example 34 in place of [6-chloro-2-(pyrazolo[5,1-b][1,3]thiazol-7-yl)pyrimidin-4-yl]{4-[(3-fluoropyridin-2-yl)amino]piperidin-1-yl}methanone.
MS (m/z): 523 [M+H]$^+$

Example 130

2-Methyl-N-[1-({6-[(2-methylbutan-2-yl)amino]-1-(pyrazolo[5,1-b][1,3]thiazol-7-yl)pyrimidin-4-yl}carbonyl)piperidin-4-yl]propanamide To a solution of N-(1-{[6-chloro-2-(pyrazolo[5,1-b][1,3]thiazol-7-yl)pyrimidin-4-yl]carbonyl}piperidin-4-yl)-2-methylpropanamide obtained in Reference Example 16 (25 mg) in DMF (1 mL) were added DIPEA (50 µL) and 2-methylbutan-2-amine (25 mg), and the mixture was stirred at 120° C. for 1 h. Then, an additional 2-methylbutan-2-amine (25 mg) was added thereto, and the mixture was stirred at 120° C. for 1 h. To the reaction solution was added water, and the mixture was extracted with ethyl acetate. The organic layer was washed with saturated aqueous sodium bicarbonate solution, dried over anhydrous magnesium sulfate, and concentrated under reduced pressure. The reaction mixture was purified by silica gel column chromatography to give the title compound (12 mg).
MS (m/z): 484 [M+H]$^+$

Example 131

N-[1-({6-[(2S)-Butan-2-ylamino]-2-(pyrazolo[5,1-b][1,3]thiazol-7-yl)pyrimidin-4-yl}carbonyl)piperidin-4-yl]propanamide Analogous to the method in Example 115, the title compound was synthesized by using (2S)-butan-2-amine in place of (2R)—N,3,3-trimethylbutan-2-amine hydrochloride.
MS (m/z): 456 [M+H]$^+$

Example 132

Methyl[1-({6-[tert-butyl(methyl)amino]-2-(pyrazolo[5,1-b][1,3]thiazol-7-yl)pyrimidin-4-yl}carbonyl)piperidin-4-yl]carbamate hydrochloride To a solution of methyl(1-{[6-chloro-2-(pyrazolo[5,1-b][1,3]thiazol-7-yl)pyrimidin-4-yl]carbonyl}piperidin-4-yl)carbamate obtained in Reference Example 14 (50 mg) in NMP (0.1 mL) were added DIPEA (103 µL) and N,2-dimethylpropan-2-amine (31 mg), and the mixture was stirred at 150° C. for 2 h in a sealed tube. The reaction mixture was purified by silica gel column chromatography to give a solid (20 mg). To a solution of the obtained solid (20 mg) in ethyl acetate (2 mL) was added 4 M hydrogen chloride-ethyl acetate solution (15 µL). The reaction mixture was concentrated under reduced pressure to give the title compound (18 mg).
MS (m/z): 472 [M–Cl]$^+$

Example 133

{6-[tert-Butyl(ethyl)amino]-2-(pyrazolo[5,1-b][1,3]thiazol-7-yl)pyrimidin-4-yl}(4-hydroxypiperidin-1-yl)methanone

[Step 1] Preparation of (4-{[tert-butyl(dimethyl)silyl]oxy}piperidin-1-yl){6-[tert-butyl(ethyl)amino]-2-(pyrazolo[5,1-b][1,3]thiazol-7-yl)pyrimidin-4-yl}methanone To a solution of (4-{[tert-butyl(dimethyl)silyl]oxy}piperidin-1-yl)[6-chloro-2-(pyrazolo[5,1-b][1,3]thiazol-7-yl)pyrimidin-4-yl]methanone obtained in Reference Example 30 (150 mg) in ethanol (1 mL) were added DIPEA (706 µL) and tert-butylamine (333 µL), and the mixture was stirred in a microwave reactor at 150° C. for 1 h. An additional tert-butylamine (333 µL) was added thereto, and the mixture was further stirred in a microwave reactor at 150° C. for an additional hour. The reaction mixture was purified by silica gel column chromatography to give a solid (111 mg). To a solution of the obtained solid (30 mg) in DMF (0.6 mL) was added 60% sodium hydride (12 mg) under ice cooling, and the mixture was stirred at room temperature for 15 min. To the mixture was added iodoethane (28 µL), and the mixture was stirred at room temperature overnight. To the reaction solution was added water, and the mixture was extracted with ethyl acetate. The organic layer was washed with saturated brine, dried over anhydrous magnesium sulfate, and concentrated under reduced pressure. The resulting residue was purified by silica gel column chromatography to give the title compound (28 mg).

$^1$H-NMR (CDCl$_3$) δ: 0.06 (3H, s), 0.08 (3H, s), 0.90 (9H, s), 1.22-1.26 (4H, m), 1.57-1.63 (1H, m), 1.68 (9H, s), 1.82-1.90 (2H, m), 3.51-3.59 (1H, m), 3.63 (2H, q), 3.72-3.90 (3H, m), 4.01-4.09 (1H, m), 6.55 (1H, s), 6.97 (1H, s), 7.82 (1H, s), 8.41 (1H, s)

[Step 2] Preparation of {6-[tert-butyl(ethyl)amino]-2-(pyrazolo[5,1-b][1,3]thiazol-7-yl)pyrimidin-4-yl}(4-hydroxypiperidin-1-yl)methanone To a solution of (4-{[tert-butyl(dimethyl)silyl]oxy}piperidin-1-yl){6-[tert-butyl(ethyl)amino]-2-(pyrazolo[5,1-b][1,3]thiazol-7-yl)pyrimidin-4-yl}methanone obtained in Step 1 (28 mg) in THF (0.5 mL) was added 1 M tetrabutylammonium fluoride (THF solution, 152 µL), and the mixture was stirred at room temperature overnight. To the reaction solution was added water, and the aqueous layer was extracted with ethyl acetate. The organic layer was washed with saturated brine, dried over anhydrous magnesium sulfate, and concentrated under reduced pressure. The resulting residue was purified by silica gel column chromatography to give the title compound (20 mg).
MS (m/z): 429 [M+H]$^+$

Example 134

Cyclopropyl(1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate To a solution of cyclopropyl(1-{[6-chloro-2-(pyrazolo[5,1-b][1,3]thiazol-7-yl)pyrimidin-4-yl]carbonyl}piperidin-4-yl)carbamate obtained in Reference Example 21 (25 mg) in DMF (1 mL) were added DIPEA (19 µL) and (1S)-1-cyclopropylethanamine (7 mg), and the mixture was stirred at 100° C. for 1 h. The reaction solution was diluted with ethyl acetate, separated by adding saturated aqueous sodium bicarbonate solution, the aqueous layer was further extracted with ethyl acetate, and the combined organic layer was dried over anhydrous magnesium sulfate, and concentrated under reduced pressure. The resulting residue was purified by silica gel column chromatography to give the title compound (23 mg).
MS (m/z): 496 [M+H]+

Example 135

Cyclopropyl(1-{[6-(tert-butylamino)-2-(pyrazolo[5,1-b][1,3]thiazol-7-yl)pyrimidin-4-yl]carbonyl}piperidin-4-yl)carbamate Analogous to the method in Example 134, the title compound was synthesized by using tert-butylamine in place of (1S)-1-cyclopropylethanamine.
MS (m/z): 484 [M+H]+

Example 136

2,2-Difluoro-N-(1-{[6-{[(2R)-3-methylbutan-2-yl]amino}-2-(pyrazolo[5,1-b][1,3]thiazol-7-yl)pyrimidin-4-yl]carbonyl}piperidin-4-yl)acetamide To a solution of N-(1-{[6-chloro-2-(pyrazolo[5,1-b][1,3]thiazol-7-yl)pyrimidin-4-yl]carbonyl}piperidin-4-yl)-2,2-difluoroacetamide obtained in Reference Example 28 (30 mg) in 2-propanol (2 mL) were added DIPEA (47 μL) and (2R)-3-methylbutan-2-amine (18 mg), and the mixture was stirred at 80° C. for 3 h. The reaction solution was concentrated under reduced pressure, and the resulting residue was purified by silica gel column chromatography to give the title compound (32 mg).
MS (m/z): 492 [M+H]+

Example 137

3-[1-({6-[(2,2-Dimethylpropyl)amino]-2-(pyrazolo[5,1-b][1,3]thiazol-7-yl)pyrimidin-4-yl}carbonyl)piperidin-4-yl]-1,1-dimethylurea To a solution of 3-(1-{[6-chloro-2-(pyrazolo[5,1-b][1,3]thiazol-7-yl)pyrimidin-4-yl]carbonyl}piperidin-4-yl)-1,1-dimethylurea obtained in Reference Example 33 (20 mg) in DMF (1 mL) were added DIPEA (32 μL) and 2,2-dimethylpropan-1-amine (12 mg), and the mixture was stirred at 60° C. for 4 h. The reaction mixture was concentrated under reduced pressure, and the resulting residue was purified by silica gel column chromatography to give the title compound (21 mg).
MS (m/z): 485 [M+H]+

Example 138

3-(1-{[6-{[(1R)-1-Cyclopropylethyl]amino}-2-(pyrazolo[5,1-b][1,3]thiazol-7-yl)pyrimidin-4-yl]carbonyl}piperidin-4-yl)-1,1-dimethylurea Analogous to the method in Example 137, the title compound was synthesized by using (1R)-1-cyclopropylethanamine in place of 2,2-dimethylpropan-1-amine.
MS (m/z): 483 [M+H]+

Example 139

Propan-2-yl[1-({6-[(3-methyloxetan-3-yl)amino]-2-(pyrazolo[5,1-b][1,3]thiazol-7-yl)pyrimidin-4-yl}carbonyl)piperidin-4-yl]carbamate Analogous to the method in Example 29, the title compound was synthesized by using 3-methyloxetan-3-amine hydrochloride in place of (2R)-3,3-dimethylbutan-2-amine.
MS (m/z): 500 [M+H]+

Example 140

Methyl[1-({6-[(dicyclopropylmethyl)amino]-2-(pyrazolo[5,1-b][1,3]thiazol-7-yl)pyrimidin-4-yl}carbonyl)piperidin-4-yl]carbamate Analogous to the method in Example 24 Step 1, the title compound was synthesized by using dicyclopropylmethanamine in place of (2R)-3-methylbutan-2-amine.
MS (m/z): 496 [M+H]+

Example 141

Methyl(1-{[6-phenoxy-2-(pyrazolo[5,1-b][1,3]thiazol-7-yl)pyrimidin-4-yl]carbonyl}piperidin-4-yl)carbamate To a solution of phenol (34 mg) in THF (3 mL) was added 60% sodium hydride (6 mg) under ice cooling, and the mixture was stirred for 5 min. Then, methyl(1-{[6-chloro-2-(pyrazolo[5,1-b][1,3]thiazol-7-yl)pyrimidin-4-yl]carbonyl}piperidin-4-yl)carbamate obtained in Reference Example 14 (30 mg) was added thereto and the mixture was stirred at 70° C. overnight. To the reaction solution was added water, and the mixture was extracted with ethyl acetate. The organic layer was washed with saturated brine, dried over anhydrous magnesium sulfate, and concentrated under reduced pressure. The resulting residue was purified by silica gel column chromatography to give the title compound (19 mg).
MS (m/z): 479 [M+H]+

Example 142 tert-Butyl 4-{[6-({4-[(methoxycarbonyl)amino]piperidin-1-yl}carbonyl)-2-(pyrazolo[5,1-b][1,3]thiazol-7-yl)pyrimidin-4-yl]amino}piperidine-1-carboxylate To a solution of methyl(1-{[6-chloro-2-(pyrazolo[5,1-b][1,3]thiazol-7-yl)pyrimidin-4-yl]carbonyl}piperidin-4-yl)carbamate obtained in Reference Example 14 (100 mg) in 2-propanol (2.0 mL) were added DIPEA (144 μL) and tert-butyl 4-aminopiperidine-1-carboxylate (143 mg), and the mixture was reacted in a microwave reactor at 150° C. for 1 h. The reaction mixture was purified by silica gel column chromatography to give the title compound (105 mg).
MS (m/z): 585 [M+H]+

Example 143

Methyl(1-{[6-(piperidin-4-ylamino)-2-(pyrazolo[5,1-b][1,3]thiazol-7-yl)pyrimidin-4-yl]carbonyl}piperidin-4-yl)carbamate dihydrochloride To tert-butyl 4-{[6-({4-[(methoxycarbonyl)amino]piperidin-1-yl}carbonyl)-2-(pyrazolo[5,1-b][1,3]thiazol-7-yl)pyrimidin-4-yl]amino}piperidine-1-carboxylate obtained in Example 142 (98 mg) was added 2 M hydrogen chloride-methanol solution, and the mixture was stirred at room temperature overnight. The reaction solution was concentrated under reduced pressure, the resulting residue was triturated with ethyl acetate, and the powder was collected on a filter, and dried to give the title compound (91 mg).
MS (m/z): 485[M−2Cl−H]+

Example 144

Methyl[1-({6-[(1-cyanocyclopropyl)amino]-2-(pyrazolo[5,1-b][1,3]thiazol-7-yl)pyrimidin-4-yl}carbonyl)piperidin-4-yl]carbamate Analogous to the method in Example 142, the title compound was synthesized by using 1-aminocyclopropanecarbonitrile hydrochloride in place of tert-butyl 4-aminopiperidine-1-carboxylate.
MS (m/z): 467 [M+H]$^+$

Example 145

Methyl(1-{[6-{[(1S)-1-cyclopropylethyl]amino}-5-methoxy-2-(pyrazolo[5,1-b][1,3]thiazol-7-yl)pyrimidin-4-yl]carbonyl}piperidin-4-yl)carbamate Under argon atmosphere, to a solution of methyl(1-{[6-chloro-5-methoxy-2-(pyrazolo[5,1-b][1,3]thiazol-7-yl)pyrimidin-4-yl]carbonyl}piperidin-4-yl)carbamate obtained in Reference Example 35 (15 mg) in 2-propanol (1 mL) were added TEA (19 µL) and (1S)-1-cyclopropylethanamine (6 mg), and the mixture was stirred at 100° C. overnight. The reaction solution was concentrated under reduced pressure, and the resulting residue was purified by silica gel column chromatography to give the title compound (16 mg).
MS (m/z): 500 [M+H]$^4$

Example 146

Methyl(1-{[6-{[(2R)-3,3-dimethylbutan-2-yl]amino}-5-methoxy-2-(pyrazolo[5,1-b][1,3]thiazol-7-yl)pyrimidin-4-yl]carbonyl}piperidin-4-yl)carbamate Analogous to the method in Example 145, the title compound was synthesized by using (2R)-3,3-dimethylbutan-2-amine in place of (1S)-1-cyclopropylethanamine.
MS (m/z): 516 [M+H]$^+$

Example 147 tert-Butyl(3S)-3-{[6-({4-[(methoxycarbonyl)amino]piperidin-1-yl}carbonyl)-2-(pyrazolo[5,1-b][1,3]thiazol-7-yl)pyrimidin-4-yl]amino}pyrrolidine-1-carboxylate Analogous to the method in Example 142, the title compound was synthesized by using (S)-3-aminopyrrolidine-1-carboxylic acid tert-butyl in place of tert-butyl 4-aminopiperidine-1-carboxylate.
MS (m/z): 571 [M+H]$^+$

Example 148 tert-Butyl(3R)-3-{[6-({4-[(methoxycarbonyl)amino]piperidin-1-yl}carbonyl)-2-(pyrazolo[5,1-b][1,3]thiazol-7-yl)pyrimidin-4-yl]amino}pyrrolidine-1-carboxylate Analogous to the method in Example 142, the title compound was synthesized by using tert-butyl(R)-3-aminopyrrolidine-1-carboxylic acid in place of tert-butyl 4-aminopiperidine-1-carboxylate.
MS (m/z): 571 [M+H]$^+$

Example 149

Methyl[1-({2-(pyrazolo[5,1-b][1,3]thiazol-7-yl)-6-[(3S)-pyrrolidin-3-ylamino]pyrimidin-4-yl}carbonyl)piperidin-4-yl]carbamate dihydrochloride Analogous to the method in Example 143, the title compound was synthesized by using tert-butyl(3S)-3-{[6-({4-[(methoxycarbonyl)amino]piperidin-1-yl}carbonyl)-2-(pyrazolo[5,1-b][1,3]thiazol-7-yl)pyrimidin-4-yl]amino}pyrrolidine-1-carboxylate obtained in Example 147.
MS (m/z): 471[M−2Cl−H]$^+$

Example 150

Methyl[1-({2-(pyrazolo[5,1-b][1,3]thiazol-7-yl)-6-[(3R)-pyrrolidin-3-ylamino]pyrimidin-4-yl}carbonyl)piperidin-4-yl]carbamate dihydrochloride Analogous to the method in Example 143, the title compound was synthesized by using tert-butyl(3R)-3-{[6-({4-[(methoxycarbonyl)amino]piperidin-1-yl}carbonyl)-2-(pyrazolo[5,1-b][1,3]thiazol-7-yl)pyrimidin-4-yl]amino}pyrrolidine-1-carboxylate obtained in Example 148.
MS (m/z): 471[M−2Cl−H]$^+$

Example 151

Methyl(1-{[6-{[(3R)-1-methylpyrrolidin-3-yl]amino}-2-(pyrazolo[5,1-b][1,3]thiazol-7-yl)pyrimidin-4-yl]carbonyl}piperidin-4-yl)carbamate To a solution of methyl[1-({2-(pyrazolo[5,1-b][1,3]thiazol-7-yl)-6-[(3R)-pyrrolidin-3-ylamino]pyrimidin-4-yl}carbonyl)piperidin-4-yl]carbamate dihydrochloride obtained in Example 150 (20 mg) in methanol (0.2 mL) were added 2-picoline borane complex (40 mg), 37% formaldehyde aqueous solution (30 µL) and acetic acid (20 µL), and the mixture was stirred at room temperature overnight. The reaction mixture was purified by silica gel column chromatography to give the title compound (7 mg).
MS (m/z): 485 [M+H]$^+$

Example 152

Methyl(1-{[6-{[(3R)-1-acetylpyrrolidin-3-yl]amino}-2-(pyrazolo[5,1-b][1,3]thiazol-7-yl)pyrimidin-4-yl]carbonyl}piperidin-4-yl)carbamate To a solution of methyl[1-({2-(pyrazolo[5,1-b][1,3]thiazol-7-yl)-6-[(3R)-pyrrolidin-3-ylamino]pyrimidin-4-yl}carbonyl)piperidin-4-yl]carbamate dihydrochloride obtained in Example 150 (20 mg) in THF (0.5 mL) were added triethylamine (51 µL) and acetyl chloride (26 µL) under ice cooling, and the mixture was stirred at room temperature for 3 h. The reaction mixture was purified by silica gel column chromatography to give the title compound (8 mg).
MS (m/z): 513 [M+H]$^+$

Example 153

Methyl[1-({6-[(2S)-butan-2-ylamino]-5-methoxy-2-(pyrazolo[5,1-b][1,3]thiazol-7-yl)pyrimidin-4-yl}carbonyl)piperidin-4-yl]carbamate Analogous to the method in Example 145, the title compound was synthesized by using (2S)-butan-2-amine in place of (1S)-1-cyclopropylethanamine.
MS (m/z): 488 [M+H]$^+$

Example 154

Methyl(1-{[6-{[(1S)-1-cyclopropylethyl]amino}-5-ethoxy-2-(pyrazolo[5,1-b][1,3]thiazol-7-yl)pyrimidin-4-yl]carbonyl}piperidin-4-yl)carbamate Under argon atmosphere, to a solution of methyl(1-{[6-chloro-5-ethoxy-2-(pyrazolo[5,1-b][1,3]thiazol-7-yl)pyrimidin-4-yl]carbonyl}piperidin-4-yl)carbamate obtained in Reference Example 36 (10 mg) in 2-propanol (1 mL) were added TEA (12 µL) and (1S)-1-cyclopropylethanamine (4 mg), and the mixture was stirred at 100° C. overnight. The reaction solution was concentrated under reduced pressure, and the resulting residue was purified by silica gel column chromatography to give the title compound (5 mg).
MS (m/z): 514 [M+H]$^+$

Example 155

Methyl(1-{[6-{[(2R)-3,3-dimethylbutan-2-yl]amino}-5-ethoxy-2-(pyrazolo[5,1-b][1,3]thiazol-7-yl)pyrimidin-4-yl]carbonyl}piperidin-4-yl)carbamate Analogous to the method in Example 154, the title compound was synthesized by using (2R)-3,3-dimethylbutan-2-amine in place of (1S)-1-cyclopropylethanamine. MS (m/z): 530 [M+H]$^+$

Example 156

Methyl(1-{[2-(pyrazolo[5,1-b][1,3]thiazol-7-yl)-6-(pyridin-3-yloxy)pyrimidin-4-yl]carbonyl}piperidin-4-yl)carbamate To a solution of pyridin-3-ol (34 mg) in DMF (1.5 mL) was added 60% sodium hydride (9.0 mg) under ice cooling, and the mixture was stirred for 5 min. Then, methyl(1-{[6-chloro-2-(pyrazolo[5,1-b][1,3]thiazol-7-yl)pyrimidin-4-yl]carbonyl}piperidin-4-yl)carbamate obtained in Reference Example 14 (30 mg) was added thereto, and the mixture was stirred at room temperature for 30 min. The reaction mixture was purified by silica gel column chromatography to give the title compound (23 mg).
MS (m/z): 480 [M+H]$^+$

Example 157

N-(1-{[6-(2-ethylpiperidin-1-yl)-2-(pyrazolo[5,1-b][1,3]thiazol-7-yl)pyrimidin-4-yl]carbonyl}piperidin-4-yl)cyclopropanecarboxamide To a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 15 (15 mg) in 1-butanol (1 mL) were added DIPEA (151 µL) and 2-ethylpiperidine (79 mg), and the mixture was reacted in a microwave reactor at 170° C. for 1 h. The reaction mixture was purified by silica gel column chromatography to give the title compound (18 mg).
MS (m/z): 508 [M+H]$^+$

Example 158

Methyl(1-2-(pyrazolo[5,1-b][1,3]thiazol-7-yl)-6-[(2,2,2-trifluoroethyl)amino]pyrimidine-4-carbonylpiperidin-4-yl)carbamate Analogous to the method in Example 24 Step 1, the title compound was synthesized by using 2,2,2-trifluoroethan-1-amine in place of (2R)-3-methylbutan-2-amine.
MS (m/z): 484 [M+H]$^+$

Example 159

N-1-[2-(pyrazolo[5,1-b][1,3]thiazol-7-yl)-6-[(thiophen-2-yl)methyl]aminopyrimidine-4-carbonyl]piperidin-4-ylcyclopropanecarboxamide Analogous to the method in Example 16, the title compound was synthesized by using thiophen-2-ylmethanamine in place of (2R)-3,3-dimethylbutan-2-amine.
MS (m/z): 508 [M+H]$^+$

Example 160

N-1-[6-[(furan-2-yl)methyl]amino-2-(pyrazolo[5,1-b][1,3]thiazol-7-yl)pyrimidine-4-carbonyl]piperidin-4-ylcyclopropanecarboxamide Analogous to the method in Example 16, the title compound was synthesized by using furan-2-ylmethanamine in place of (2R)-3,3-dimethylbutan-2-amine.
MS (m/z): 492 [M+H]$^+$

Example 161

Methyl 1-[6-[(1R)-1-cyclohexylethyl]amino-2-(pyrazolo[5,1-b][1,3]thiazol-7-yl)pyrimidine-4-carbonyl]piperidin-4-ylcarbamate Analogous to the method in Example 24 Step 1, the title compound was synthesized by using (1R)-1-cyclohexylethan-1-amine in place of (2R)-3-methylbutan-2-amine.
MS (m/z): 512 [M+H]$^+$

Example 162

Methyl 1-[2-(pyrazolo[5,1-b][1,3]thiazol-7-yl)-6-[1-(pyridin-4-yl)ethyl]aminopyrimidine-4-carbonyl]piperidin-4-ylcarbamate Analogous to the method in Example 24 Step 1, the title compound was synthesized by using 1-(pyridin-4-yl)ethan-1-amine in place of (2R)-3-methylbutan-2-amine.
MS (m/z): 507 [M+H]$^+$

Example 163

Methyl(1-6-[(2-cyclopropylethyl)amino]-2-(pyrazolo[5,1-b][1,3]thiazol-7-yl)pyrimidine-4-carbonylpiperidin-4-yl)carbamate Analogous to the method in Example 24 Step 1, the title compound was synthesized by using 2-cyclopropylethanamine in place of (2R)-3-methylbutan-2-amine.
MS (m/z): 470 [M+H]$^+$.

Example 164

Tert-butyl 3-([6-4-[(methoxycarbonyl)amino]piperidine-1-carbonyl-2-(pyrazolo[5,1-b][1,3]thiazol-7-yl)pyrimidin-4-yl]oxymethyl)azetidine-1-carboxylate Analogous to the method in Example 64, the title compound was synthesized by using tert-butyl 3-(hydroxymethyl)azetidine-1-carboxylate in place of 3,3-dimethylbutan-2-ol.
MS (m/z): 572 [M+H]$^+$

Example 165

N-1-[6-[(1S)-1-cyclopropylethyl]amino-2-(pyrazolo[5,1-b][1,3]thiazol-7-yl)pyrimidine-4-carbonyl]piperidin-4-yl cyclobutanecarboxamide Analogous to the method in Example 30 Step 3, the title compound was synthesized by using cyclobutanecarbonyl chloride in place of benzoyl chloride.
MS (m/z): 494 [M+H]$^+$

Example 166

N-1-[6-[(1S)-1-cyclopropylethyl])amino-2-(pyrazolo[5,1-b][1,3]thiazol-7-yl)pyrimidine-4-carbonyl]piperidin-4-ylcyclopentanecarboxamide Analogous to the method in Example 30 Step 3, the title compound was synthesized by using cyclopentanecarbonyl chloride in place of benzoyl chloride.
MS (m/z): 508 [M+H]$^+$

Example 167

N-1-[6-[(1S)-1-cyclopropylethyl]amino-2-(pyrazolo[5,1-b][1,3]thiazol-7-yl)pyrimidine-4-carbonyl]piperidin-4-ylcyclohexanecarboxamide Analogous to the method in Example 30 Step 3, the title compound was synthesized by using cyclohexanecarbonyl chloride in place of benzoyl chloride.
MS (m/z): 522 [M+H]$^+$

Example 168

N-(1-6-[(trans-4-hydroxycyclohexyl)amino]-2-(pyrazolo[5,1-b][1,3]thiazol-7-yl)pyrimidine-4-carbonylpiperidin-4-yl)cyclopropanecarboxamide Analogous to the method in Example 16, the title compound was synthesized by using trans-4-aminocyclohexan-1-ol in place of (2R)-3,3-dimethylbutan-2-amine.
MS (m/z): 510 [M+H]$^+$

Example 169

N-1-[6-[(1R)-1-cyclohexylethyl]amino-2-(pyrazolo[5,1-b][1,3]thiazol-7-yl)pyrimidine-4-carbonyl]piperidin-4-ylcyclopropanecarboxamide Analogous to the method in Example 16, the title compound was synthesized by using (1R)-1-cyclohexylethan-1-amine in place of (2R)-3,3-dimethylbutan-2-amine.
MS (m/z): 522 [M+H]$^+$

Example 170

N-1-[2-(pyrazolo[5,1-b][1,3]thiazol-7-yl)-6-[1-(pyridin-4-yl)ethyl]aminopyrimidine-4-carbonyl]piperidin-4-ylcyclopropancarboxamide Analogous to the method in Example 16, the title compound was synthesized by using 1-(4-pyridyl)ethanamine in place of (2R)-3,3-dimethylbutan-2-amine.
MS (m/z): 517 [M+H]$^+$

Example 171

Tert-butyl 4-[6-4-[(cyclopropanecarbonyl)amino]piperidine-1-carbonyl-2-(pyrazolo[5,1-b][1,3]thiazol-7-yl)pyrimidin-4-yl]aminopiperidine-1-carboxylate Analogous to the method in Example 16, the title compound was synthesized by using tert-butyl 4-aminopiperidine-1-carboxylate in place of (2R)-3,3-dimethylbutan-2-amine.
MS (m/z): 595 [M+H]$^+$

Example 172

N-(1-6-[(oxan-4-yl)amino]-2-(pyrazolo[5,1-b][1,3]thiazol-7-yl)pyrimidine-4-carbonylpiperidin-4-yl)cyclopropanecarboxamide Analogous to the method in Example 16, the title compound was synthesized by using tetrahydropyran-2-amine in place of (2R)-3,3-dimethylbutan-2-amine.
MS (m/z): 496 [M+H]$^+$

Example 173

N-(1-6-[(oxetan-3-yl)amino]-2-(pyrazolo[5,1-b][1,3]thiazol-7-yl)pyrimidine-4-carbonylpiperidin-4-yl)cyclopropanecarboxamide Analogous to the method in Example 16, the title compound was synthesized by using oxetan-3-amine in place of (2R)-3,3-dimethylbutan-2-amine.
MS (m/z): 468 [M+H]$^+$

Example 174

Methyl(1-6-[(3-cyclopropyl-2,2-dimethylpropyl)amino]-2-(pyrazolo[5,1-b][1,3]thiazol-7-yl)pyrimidine-4-carbonylpiperidin-4-yl)carbamate Analogous to the method in Example 24 Step 1, the title compound was synthesized by using 3-cyclopropyl-2,2-dimethylpropane-1-amine hydrochloride in place of (2R)-3-methylbutan-2-amine.
MS (m/z): 512 [M+H]$^+$

Example 175

Methyl 1-[6-([1-(methanesulfonyl)piperidin-4-yl]methylamino)-2-(pyrazolo[5,1-b][1,3]thiazol-7-yl)pyrimidine-4-carbonyl]piperidin-4-ylcarbamate

[Step 1] Preparation of tert-butyl 4-([6-4-[(methoxycarbonyl)amino]piperidine-1-carbonyl-2-(pyrazolo[5,1-b][1,3]thiazol-7-yl)pyrimidin-4-yl]aminomethyl)piperidine-1-carboxylate Analogous to the method in Example 24 Step 1, the title compound was synthesized by using tert-butyl 4-(aminomethyl)piperidine-1-carboxylate in place of (2R)-3-methylbutan-2-amine.
MS (m/z): 599 [M+H]$^+$

[Step 2] Preparation of methyl 1-[6-([1-(methanesulfonyl)piperidin-4-yl]methylamino)-2-(pyrazolo[5,1-b][1,3]thiazol-7-yl)pyrimidine-4-carbonyl]piperidin-4-ylcarbamate To tert-butyl 4-([6-4-[(methoxycarbonyl)amino]piperidine-1-carbonyl-2-(pyrazolo[5,1-b][1,3]thiazol-7-yl)pyrimidin-4-yl]aminomethyl)piperidine-1-carboxylate obtained in Step 1 (115 mg) was added 2 M hydrogen chloride-methanol solution (2 mL), and the mixture was stirred at 40° C. for 5 h. The reaction solution was concentrated under reduced pressure, and the resulting residue was washed with ether, collected on a filter, and dried to give a solid compound (105 mg). The obtained solid compound (25 mg) was suspended in dichloromethane, and DIPEA (38 µL) and methanesulfonyl chloride (8 mg) were added, and the mixture was stirred under ice cooling for 15 min. The reaction mixture was purified by silica gel column chromatography to give the title compound (17 mg).
MS (m/z): 577 [M+H]$^+$

Example 176

N-1-[6-[(1R)-bicyclo[2.2.1]heptan-2-yl]amino-2-(pyrazolo[5,1-b][1,3]thiazol-7-yl)pyrimidine-4-carbonyl]piperidin-4-ylcyclopropanecarboxamide Analogous to the method in Example 16, the title compound was synthesized by using norbornene-2-amine hydrochloride in place of (2R)-3,3-dimethylbutan-2-amine.
MS (m/z): 506 [M+H]$^+$

Example 177

Methyl(1-6-[(cis-4-hydroxycyclohexyl)amino]-2-(pyrazolo[5,1-b][1,3]thiazol-7-yl)pyrimidine-4-carbonylpiperidin-4-yl)carbamate Analogous to the method in Example 24 Step 1, the title compound was synthesized by using cis-4-aminocyclohexanol in place of (2R)-3-methylbutan-2-amine.
MS (m/z): 500 [M+H]$^+$

Example 178

Methyl(1-6-[(trans-4-hydroxycyclohexyl)amino]-2-(pyrazolo[5,1-b][1,3]thiazol-7-yl)pyrimidine-4-carbonylpiperidin-4-yl)carbamate Analogous to the method in Example 24 Step 1, the title compound was synthesized by using trans-4-aminocyclohexanol in place of (2R)-3-methylbutan-2-amine.
MS (m/z): 500 [M+H]$^+$

Example 179

Methyl 1-[6-(cyclopentylamino)-2-(pyrazolo[5,1-b][1,3]thiazol-7-yl)pyrimidine-4-carbonyl]piperidin-4-ylcarbamate Analogous to the method in Example 24 Step 1, the title compound was synthesized by using cyclopentanamine in place of (2R)-3-methylbutan-2-amine.
MS (m/z): 470 [M+H]$^+$

Example 180

Methyl 1-[6-(cyclohexylamino)-2-(pyrazolo[5,1-b][1,3]thiazol-7-yl)pyrimidine-4-carbonyl]piperidin-4-ylcarbamate Analogous to the method in Example 24 Step 1, the title compound was synthesized by using cyclohexanamine in place of (2R)-3-methylbutan-2-amine.
MS (m/z): 584 [M+H]$^+$

Example 181

N-(1-6-[(piperidin-4-yl)amino]-2-(pyrazolo[5,1-b][1,3]thiazol-7-yl)pyrimidine-4-carbonylpiperidin-4-yl)cyclopropanecarboxamide dihydrochloride To tert-butyl 4-[6-4-[(cyclopropanecarbonyl)amino]piperidine-1-carbonyl-2-(pyrazolo[5,1-b][1,3]thiazol-7-yl)pyrimidin-4-yl]aminopiperidine-1-carboxylate obtained in Example 171 (55 mg) was added 2 M hydrogen chloride-methanol solution (3 mL), and the mixture was stirred at room temperature for 2 h. The reaction solution was concentrated under reduced pressure, the resulting residue was washed with ether, collected on a filter, and dried to give the title compound (52 mg).
MS (m/z): 495[M−2Cl−H]$^+$

Example 182

N-1-[6-[(2R)-3,3-dimethylbutan-2-yl]amino-2-(pyrazolo[5,1-b][1,3]thiazol-7-yl)pyrimidine-4-carbonyl]piperidin-4-ylcyclohexanecarboxamide Analogous to the method in Example 40, the title compound was synthesized by using N-(piperidin-4-yl)cyclohexanecarboxamide hydrochloride in place of ethyl piperidin-4-ylcarbamate.
MS (m/z): 538 [M+H]$^+$

Example 183

N-1-[6-[(2R)-3,3-dimethylbutan-2-yl]amino-2-(pyrazolo[5,1-b][1,3]thiazol-7-yl)pyrimidine-4-carbonyl]piperidin-4-ylbenzamide Analogous to the method in Example 40, the title compound was synthesized by using N-(4-piperidyl)benzamide hydrochloride in place of ethyl piperidin-4-ylcarbamate.
MS (m/z): 532 [M+H]$^+$

Example 184

N-1-[6-[(1S)-1-cyclopropylethyl]amino-2-(pyrazolo[5,1-b][1,3]thiazol-7-yl)pyrimidine-4-carbonyl]piperidin-4-yl-2-methylbenzamide Analogous to the method in Example 30 step 3, the title compound was synthesized by using 2-methylbenzoyl chloride in place of benzoyl chloride.
MS (m/z): 530 [M+H]$^+$

Example 185

N-1-[6-[(1S)-1-cyclopropylethyl]amino-2-(pyrazolo[5,1-b][1,3]thiazol-7-yl)pyrimidine-4-carbonyl]piperidin-4-ylpyridine-2-carboxamide Analogous to the method in Example 30 step 3, the title compound was synthesized by using pyridine-2-carbonyl chloride hydrochloride in place of benzoyl chloride.
MS (m/z): 517 [M+H]$^+$

Example 186

N-1-[6-[(1S)-1-cyclopropylethyl]amino-2-(pyrazolo[5,1-b][1,3]thiazol-7-yl)pyrimidine-4-carbonyl]piperidin-4-yl-2-methoxybenzamide Analogous to the method in Example 30 step 3, the title compound was synthesized by using 2-methoxybenzoyl chloride in place of benzoyl chloride.
MS (m/z): 546 [M+H]$^+$

Example 187

N-1-[6-[(1S)-1-cyclopropylethyl]amino-2-(pyrazolo[5,1-b][1,3]thiazol-7-yl)pyrimidine-4-carbonyl]piperidin-4-ylpyridine-4-carboxamide Analogous to the method in Example 30 step 3, the title compound was synthesized by using pyridine-4-carbonyl chloride in place of benzoyl chloride.
MS (m/z): 517 [M+H]$^+$

Example 188

N-(1-6-[(1-acetylpiperidin-4-yl)amino]-2-(pyrazolo[5,1-b][1,3]thiazol-7-yl)pyrimidine-4-carbonylpiperidin-4-yl)cyclopropanecarboxamide Under argon atmosphere, to a solution of N-(1-{[6-chloro-2-(pyrazolo[5,1-b][1,3]thiazol-7-yl)pyrimidin-4-yl]carbonyl}piperidin-4-yl)cyclopropanecarboxamide (30 mg) obtained in Reference Example 15 in 2-propanol (2 mL) were added DIPEA (48 μL) and 1-(4-amino-1-piperidyl)ethanone (15 mg), and the mixture was stirred at 90° C. for 1 h. NMP (0.5 mL) was further added, and the mixture was stirred at 120° C. for 2 h. The reaction mixture was concentrated under reduced pressure. The resulting residue was purified by silica gel column chromatography to give the title compound (30 mg).
MS (m/z): 537 [M+H]$^+$

Example 189

N-1-[6-[1-(methanesulfonyl)piperidin-4-yl]amino-2-(pyrazolo[5,1-b][1,3]thiazol-7-yl)pyrimidine-4-carbonyl]piperidin-4-ylcyclopropanecarboxamide N-(1-6-[(piperidin-4-yl)amino]-2-(pyrazolo[5,1-b][1,3]thiazol-7-yl)pyrimidine-4-carbonylpiperidin-4-yl)cyclopropanecarboxamide dihydrochloride (20 mg) obtained in Example 181 was suspended in dichloromethane (2 mL), and DIPEA (30 μL) and methanesulfonyl chloride (6 mg) were added, and the mixture was stirred under ice cooling for 15 min. The reaction mixture was purified by silica gel column chromatography to give the title compound (12 mg).
MS (m/z): 573 [M+H]$^+$

Example 190

N-1-[6-[(1S)-1-cyclopropylethyl]amino-2-(pyrazolo[5,1-b][1,3]thiazol-7-yl)pyrimidine-4-carbonyl]piperidin-4-ylpentanamide Analogous to the method in Example 30 step 3, the title compound was synthesized by using valeroyl chloride in place of benzoyl chloride.
MS (m/z): 496 [M+H]$^+$

Example 191

N-1-[6-[(3R)-1-(cyanoacetyl)pyrrolidin-3-yl]amino-2-(pyrazolo[5,1-b][1,3]thiazol-7-yl)pyrimidine-4-carbonyl]piperidin-4-ylcyclopropanecarboxamide Under argon atmosphere, to a solution of tert-butyl-[(3R)-pyrrolidin-3-yl]carbamate (500 mg) in THF (5 mL) were added ethyl cyanoacetate (607 mg) and 1,8-diazabicyclo[5.4.0]-7-undecene (204 mg), and the mixture was stirred at 40° C. for 2 h. The reaction solution was diluted with ethyl acetate, separated by adding saturated aqueous sodium bicarbonate solution, and the aqueous layer was extracted with ethyl acetate. The combined organic layers were dried over anhydrous magnesium sulfate, and concentrated under reduced pressure. The resulting residue was purified by silica gel column chromatography to give a solid compound 1 (530 mg). The obtained solid compound 1 (530 mg) was dissolved in 2 M-hydrochloric acid-methanol solution (8 mL), and the mixture was stirred at room temperature overnight. Diethyl ether was added to the reaction mixture, and the resulting precipitate was collected by filtration and dried to give a solid compound 2 (331 mg). To a solution of N-(1-{[6-chloro-2-(pyrazolo[5,1-b][1,3]thiazol-7-yl)pyrimidin-4-yl]carbonyl}piperidin-4 yl)cyclopropanecarboxamide obtained in Reference Example 15 (30 mg) in NMP (1 mL) were added DIPEA (48 μL) and the above solid compound 2 (26 mg), and the mixture was stirred at 120° C. for 3 h. The reaction solution was diluted with ethyl acetate, separated by adding saturated aqueous sodium bicarbonate solution, washed with saturated brine, and the aqueous layer was extracted with ethyl acetate. The combined organic layers were dried over anhydrous magnesium sulfate, and concentrated under reduced pressure. The resulting residue was purified by silica gel column chromatography to give the title compound (22 mg).
MS (m/z): 548 [M+H]$^+$ Example 192

Methyl 4-([6-4-[(methoxycarbonyl)amino]piperidine-1-carbonyl-2-(pyrazolo[5,1-b][1,3]thiazol-7-yl)pyrimidin-4-yl]aminomethyl)piperidine-1-carboxylate Analogous to the method in Example 175 Step 2, the title compound was synthesized by using methyl chloroformate in place of methanesulfonyl chloride.
MS (m/z): 557 [M+H]$^+$ Example 193

N-1-[6-[1-(propane-2-sulfonyl)piperidin-4-yl]amino-2-(pyrazolo[5,1-b][1,3]thiazol-7-yl)pyrimidine-4-carbonyl]piperidin-4-ylcyclopropanecarboxamide Analogous to the method in Example 189, the title compound was synthesized by using propane-2-sulfonyl chloride in place of methanesulfonyl chloride.
MS (m/z): 601 [M+H]$^+$ Example 194

Methyl 4-[6-4-[(cyclopropanecarbonyl)amino]piperidine-1-carbonyl-2-(pyrazolo[5,1-b][1,3]thiazol-7-yl)pyrimidin-4-yl]aminopiperidine-1-carboxylate Analogous to the method in Example 189, the title compound was synthesized by using methyl chloroformate in place of methanesulfonyl chloride.
MS (m/z): 553 [M+H]$^+$ Example 195

N-1-[6-[(2R)-3,3-dimethylbutan-2-yl]amino-2-(pyrazolo[5,1-b][1,3]thiazol-7-yl)pyrimidine-4-carbonyl]piperidin-4-ylheptanamide

[Step 1] Preparation of (4-aminopiperidin-1-yl)[6-{[(2R)-3,3-dimethylbutan-2-yl]amino}-2-(pyrazolo[5,1-b][1,3]thiazol-7-yl)pyrimidin-4-yl]methanone To a solution of tert-butyl(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)carbamate obtained in Example 100 (305 mg) in dichloromethane (1 mL) was added TFA (1 mL), and the mixture was stirred at room temperature for 1 h. The reaction solution was diluted with chloroform, neutralized with saturated aqueous sodium bicarbonate solution, and the aqueous layer was further extracted with chloroform. The combined organic layers were washed with saturated aqueous sodium bicarbonate solution, dried over anhydrous magnesium sulfate, and concentrated under reduced pressure. The resulting residue was purified by silica gel column chromatography to give the title compound (180 mg).
MS (m/z): 428 [M+H]$^+$

[Step 2] Preparation of N-1-[6-[(2R)-3,3-dimethylbutan-2-yl]amino-2-(pyrazolo[5,1-b][1,3]thiazol-7-yl)pyrimidine-4-carbonyl]piperidin-4-ylheptanamide To a solution of (4-aminopiperidin-1-yl)[6-{[(2R)-3,3-dimethylbutan-2-yl]amino}-2-(pyrazolo[5,1-b][1,3]thiazol-7-yl)pyrimidin-4-yl]methanone obtained in step 1 (10 mg) in dichloromethane (1 mL) were added DIPEA (16 μL) and heptanoyl chloride (4 mg) under ice cooling, and the mixture was stirred at room temperature for 15 min. The reaction mixture was purified by silica gel column chromatography to give the title compound (18 mg).
MS (m/z): 540 [M+H]$^+$ Example 196

2-Chloro-N-1-[6-[(2R)-3,3-dimethylbutan-2-yl]amino-2-(pyrazolo[5,1-b][1,3]thiazol-7-yl)pyrimidine-4-carbonyl]piperidin-4-ylbenzamide Analogous to the method in Example 195 Step 2, the title compound was synthesized by using 2-chlorobenzoyl chloride in place of heptanoyl chloride.
MS (m/z): 566, 568 [M+H]$^+$ Example 197

N-1-[6-[(2R)-3,3-dimethylbutan-2-yl]amino-2-(pyrazolo[5,1-b][1,3]thiazol-7-yl)pyrimidine-4-carbonyl]piperidin-4-yl-4-fluorobenzamide Analogous to the method in Example 195 Step 2, the title compound was synthesized by using 4-fluorobenzoyl chloride in place of heptanoyl chloride.
MS (m/z): 550 [M+H]$^+$ Example 198

Methyl(1-6-[(1-propanoylpiperidin-4-yl)amino]-2-(pyrazolo[5,1-b][1,3]thiazol-7-yl)pyrimidine-4-carbonylpiperidin-4-yl)carbamate To a solution of methyl(1-{[6-(piperidin-4-ylamino)-2-(pyrazolo[5,1-b][1,3]thiazol-7-yl)pyrimidin-4-yl]carbonyl}piperidin-4-yl)carbamate dihydrochloride obtained in Example 143 (15 mg) in THF (0.5 mL) were added TEA (38 μL) and propionyl chloride (17 mg), and the mixture was stirred at room temperature for 2 h. The reaction solution was diluted with ethyl acetate, separated by adding saturated aqueous sodium bicarbonate solution, and the aqueous layer was further extracted with ethyl acetate. The combined organic layer was dried over anhydrous magnesium sulfate, and concentrated under reduced pressure. The resulting residue was purified by silica gel column chromatography to give the title compound (9 mg).
MS (m/z): 541 [M+H]$^+$ Example 199

Methyl(1-{[6-{[1-(cyanoacetyl)piperidin-4-yl]amino}-2-(pyrazolo[5,1-b][1,3]thiazol-7-yl)pyrimidin-4-yl]carbonyl}piperidin-4-yl)carbamate To a solution of methyl(1-{[6-(piperidin-4-ylamino)-2-(pyrazolo[5,1-b][1,3]thiazol-7-yl)pyrimidin-4-yl]carbonyl}piperidin-4-yl)carbamate dihydrochloride obtained in Example 143 (15 mg) in DMF (0.5 mL) were added cyanoacetic acid (5 mg), DIPEA (14 μL) and HATU (15 mg), and the mixture was stirred at room temperature overnight. The reaction solution was diluted with ethyl acetate, separated by adding saturated aqueous sodium bicarbonate solution, and the aqueous layer was further extracted with ethyl acetate. The combined organic layer was dried over anhydrous magnesium sulfate, and concentrated under reduced pressure. The resulting residue was purified by silica gel column chromatography to give the title compound (3 mg).
MS (m/z): 552 [M+H]+

Example 200

Methyl 1-[6-[1-(methanesulfonyl)piperidin-4-yl]amino-2-(pyrazolo[5,1-b][1,3]thiazol-7-yl)pyrimidine-4-carbonyl]piperidin-4-ylcarbamate Analogous to the method in Example 198, the title compound was synthesized by using methanesulfonyl chloride in place of propionyl chloride.
MS (m/z): 563 [M+H]+

Example 201

Methyl 1-[6-[(3R)-1-(cyanoacetyl)pyrrolidin-3-yl]amino-2-(pyrazolo[5,1-b][1,3]thiazol-7-yl)pyrimidine-4-carbonyl]piperidin-4-ylcarbamate Analogous to the method in Example 191, the title compound was synthesized by using methyl(1-{[6-chloro-2-(pyrazolo[5,1-b][1,3]thiazol-7-yl)pyrimidin-4-yl]carbonyl}piperidin-4-yl)carbamate in place of N-(1-{[6-chloro-2-(pyrazolo[5,1-b][1,3]thiazol-7-yl)pyrimidin-4-yl]carbonyl}piperidin-4-yl)cyclopropanecarboxamide.
MS (m/z): 538 [M+H]+

Example 202

N-1-[6-[(3R)-1-(cyanoacetyl)pyrrolidin-3-yl]amino-2-(pyrazolo[5,1-b][1,3]thiazol-7-yl)pyrimidine-4-carbonyl]piperidin-4-ylpropanamide Analogous to the method in Example 191, the title compound was synthesized by using N-(1-{[6-chloro-2-(pyrazolo[5,1-b][1,3]thiazol-7-yl)pyrimidin-4-yl]carbonyl}piperidin-4-yl)propanamide in place of N-(1-{[6-chloro-2-(pyrazolo[5,1-b][1,3]thiazol-7-yl)pyrimidin-4-yl]carbonyl}piperidin-4-yl)cyclopropanecarboxamide.
MS (m/z): 536 [M+H]+

Example 203

Ethyl 1-[6-[(3R)-1-(cyanoacetyl)pyrrolidin-3-yl]amino-2-(pyrazolo[5,1-b][1,3]thiazol-7-yl)pyrimidine-4-carbonyl]piperidin-4-ylcarbamate Analogous to the method in Example 191, the title compound was synthesized by using ethyl(1-{[6-chloro-2-(pyrazolo[5,1-b][1,3]thiazol-7-yl)pyrimidin-4-yl]carbonyl}piperidin-4-yl)carbamate in place of N-(1-{[6-chloro-2-(pyrazolo[5,1-b][1,3]thiazol-7-yl)pyrimidin-4-yl]carbonyl}piperidin-4-yl)cyclopropanecarboxamide.
MS (m/z): 552 [M+H]+

Example 204

N-1-[6-[(3S)-1-(cyanoacetyl)pyrrolidin-3-yl]amino-2-(pyrazolo[5,1-b][1,3]thiazol-7-yl)pyrimidine-4-carbonyl]piperidin-4-ylcyclopropanecarboxamide Analogous to the method in Example 191, the title compound was synthesized by using tert-butyl N-[(3S)-pyrrolidin-3-yl]carbamate in place of tert-butyl N-[(3R)-pyrrolidin-3-yl]carbamate.
MS (m/z): 548 [M+H]+

Example 205

Methyl 1-[6-[(3R)-1-(cyclopropanecarbonyl)pyrrolidin-3-yl]amino-2-(pyrazolo[5,1-b][1,3]thiazol-7-yl)pyrimidine-4-carbonyl]piperidin-4-ylcarbamate Analogous to the method in Example 152, the title compound was synthesized by using cyclopropanecarbonyl chloride in place of acetyl chloride.
MS (m/z): 539 [M+H]+

Example 206

Methyl 1-[6-[(3R)-1-(cyclobutanecarbonyl)pyrrolidin-3-yl]amino-2-(pyrazolo[5,1-b][1,3]thiazol-7-yl)pyrimidine-4-carbonyl]piperidin-4-ylcarbamate Analogous to the method in Example 152, the title compound was synthesized by using cyclobutanecarbonyl chloride in place of acetyl chloride.
MS (m/z): 553 [M+H]+

Example 207

Methyl 1-[6-[(3R)-1-butanoylpyrrolidine-3-yl]amino-2-(pyrazolo[5,1-b][1,3]thiazol-7-yl)pyrimidine-4-carbonyl]piperidin-4-ylcarbamate Analogous to the method in Example 152, the title compound was synthesized by using butyryl chloride in place of acetyl chloride.
MS (m/z): 541 [M+H]+

Test Example 1

Inhibitory Effect on JAK Tyrosine Kinase

1. Preparation of Test Compound
The test compound was dissolved in dimethyl sulfoxide (DMSO) to 10 mM and further diluted with DMSO to the concentrations of 1000, 100, 10, 1, 0.1 and 0.01 µM, respectively. For JAK1, these solutions of the test compound at the six concentrations 10 mM, 1000 µM, 100 µM, 10 µM, 1 µM and 0.1 µM were used. For JAK2 and JAK3, these solutions of the test compound at the six concentrations 1000 µM, 100 µM, 10 µM, 1 µM, 0.1 µM and 0.01 µM were used. The test compound solutions were diluted further to 20-fold with an assay buffer to obtain a sample solution. 15 mM Tris-HCl (pH7.5), 0.01 (v/v) % Tween-20 and 1 mM dithiothreitol were used as an assay buffer. DMSO was diluted to 20-fold with the assay buffer and was used as a negative control.

2. JAK Tyrosine Kinase Inhibitory Activity in the Presence of 1 mM ATP
The activity was determined by ELISA method. Each of the sample solutions was added to a streptavidine coated 96-well plate (DELFIA Strip Plate 8×12 well, PerkinElmer) at 10 µL/well (n=2). A substrate solution containing biotinylated peptide substrate (1250 nM for JAK1, 625 nM for JAK2 and JAK3), 2.5 mM ATP (final concentration 1 mM), 25 mM MgCl$_2$, 15 mM Tris-HCl (pH 7.5), 0.01 (v/v) % Tween-20 and 1 mM dithiothreitol, was added to the plate at 20 µL/well. Finally, JAK tyrosine kinase (Carna Biosciences, Inc.), which was previously diluted with the assay buffer to 7.5 nM for JAK1 and 0.75 nM for JAK2 and JAK3, was added to the plate at 20 µL/well, and the plate was incubated at 30° C. for 1 h. The plate was washed four times with buffer (50 mM Tris-HCl (pH 7.5), 150 mM NaCl, 0.02 (v/v) % Tween-20). A blocking buffer (0.1% Bovine Serum Albumin, 50 mM Tris-HCl (pH 7.5), 150 mM NaCl, 0.02 (v/v) % Tween-20) was added to the plate at 150 µL/well and the plate was blocked at 30° C. for 1 h. The blocking buffer was removed, and a horse radish peroxidase-labeled anti-phosphorylated tyrosine antibody (BD Biosciences, Inc.) (diluted to 10000-fold with the blocking buffer) was added to the plate at 100 µL/well, and the plate was incubated at 30° C. for 30 min. The plate was washed with the washing buffer four times, and 3,3',5,5'-tetramethylbenzidine solution (Nacalai Tesque) was added to the plate at 100 µL/well to develop the color for 10 minutes. To the plate was added 0.1 M sulfuric acid at 100 µL/well to stop the reaction. The absorbance at 450 nm was measured using a microplate reader (BIO-RAD).

3. Analysis of the Results

A non-linear regression analysis using SAS system (SAS Institute Inc.) was performed for the absorbance as measured, and the concentration of the test compound that resulted in 50% inhibition of the respective tyrosine kinase activity ($IC_{50}$) was calculated. The results are shown in the following Tables 1 to 6.

TABLE 1

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
| --- | --- | --- | --- |
| 1 | 52 | 3400 | 3400 |
| 2 | 570 | 2100 | 2700 |
| 3 | 62 | 1400 | 3200 |
| 4 | 210 | 730 | 3000 |
| 5 | 130 | 2500 | 1400 |
| 6 | 240 | 1800 | 2800 |
| 7 | 69 | >10000 | 2700 |
| 8 | 52 | 2400 | 3800 |
| 9 | 19 | 960 | 2000 |
| 11 | 21 | 2500 | 4800 |
| 12 | 120 | 2200 | 1800 |
| 13 | 400 | 2400 | 1600 |
| 14 | 69 | 1700 | 1500 |
| 15 | 110 | 2500 | 7200 |
| 16 | 53 | 2200 | 2200 |
| 17 | 230 | 5100 | 5800 |
| 18 | 310 | 2300 | 1700 |
| 19 | 710 | 4400 | 6500 |
| 20 | 1400 | 4700 | 4200 |
| 21 | 230 | 2200 | >10000 |
| 22 | 130 | 800 | 3700 |
| 23 | 860 | 870 | 3300 |
| 24 | 290 | 1500 | 4200 |
| 25 | 200 | 800 | 2000 |
| 26 | 75 | 2100 | 2100 |
| 27 | 140 | 2500 | 4300 |
| 28 | 120 | 2100 | >10000 |
| 29 | 140 | 1200 | 3000 |
| 30 | 110 | 1400 | >10000 |

TABLE 2

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
| --- | --- | --- | --- |
| 32 | 380 | 1800 | >10000 |
| 33 | 130 | 1700 | 1700 |
| 34 | 350 | 1900 | 3000 |
| 35 | 270 | 2400 | >10000 |
| 36 | 86 | 620 | >10000 |
| 37 | 240 | 1600 | >10000 |
| 38 | 260 | 1200 | >10000 |
| 39 | 140 | 1300 | 2900 |
| 41 | 96 | 2700 | >10000 |
| 43 | 130 | >10000 | >10000 |
| 44 | 66 | 1300 | >10000 |
| 45 | 310 | 5700 | >10000 |
| 46 | 170 | 1600 | 7200 |
| 48 | 150 | >10000 | >10000 |
| 50 | 150 | 2000 | 2500 |
| 52 | 180 | 9300 | >10000 |
| 55 | 140 | >10000 | >10000 |
| 56 | 940 | 7300 | >10000 |
| 58 | 400 | 2900 | >10000 |
| 59 | 140 | 3900 | 5600 |
| 60 | 72 | 5400 | 6100 |
| 61 | 540 | >10000 | 9400 |
| 62 | 10 | 1000 | 1100 |
| 63 | 180 | 7300 | 10000 |
| 64 | 260 | 3100 | >10000 |
| 65 | 130 | 3100 | 10000 |
| 66 | 110 | 620 | 2400 |
| 67 | 25 | 680 | 1900 |
| 68 | 73 | 790 | 2100 |
| 69 | 810 | 3500 | 5700 |

TABLE 3

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
| --- | --- | --- | --- |
| 71 | 200 | 3700 | 4000 |
| 72 | 310 | 6100 | 5900 |
| 73 | 73 | 3200 | 2200 |
| 74 | 95 | 3100 | 2600 |
| 75 | 150 | 930 | 4800 |
| 77 | 980 | 3200 | >10000 |
| 78 | 4100 | >10000 | >10000 |
| 79 | 870 | 3300 | >10000 |
| 80 | 110 | 820 | 2300 |
| 81 | 1600 | 2200 | 3300 |
| 82 | 58 | 9700 | 5800 |
| 85 | 330 | 2200 | 2300 |
| 87 | 250 | 1600 | 9500 |
| 88 | 190 | 1000 | 4100 |
| 90 | 620 | 1200 | 1800 |
| 93 | 40 | 1200 | 1000 |
| 94 | 1900 | 2200 | 5400 |
| 96 | 250 | 1000 | 2200 |
| 97 | 210 | 1300 | 2700 |
| 98 | 37 | 1400 | 1400 |
| 99 | 19 | 790 | 2600 |
| 100 | 140 | 3000 | 3400 |
| 101 | 98 | 1800 | 3100 |
| 102 | 24 | 1300 | 1700 |
| 103 | 140 | 2400 | 5900 |
| 104 | 200 | 3000 | 3400 |
| 106 | 600 | 1300 | 2800 |
| 107 | 200 | 3500 | 1600 |
| 108 | 200 | 2500 | >10000 |
| 109 | 190 | 1800 | 2400 |

TABLE 4

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
| --- | --- | --- | --- |
| 110 | 78 | 880 | >10000 |
| 111 | 120 | 2400 | >10000 |

TABLE 4-continued

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
|---|---|---|---|
| 112 | 350 | 3500 | 2900 |
| 114 | 360 | 1200 | 2700 |
| 116 | 210 | 1900 | 3800 |
| 117 | 1400 | >10000 | 5700 |
| 119 | 670 | 4200 | >10000 |
| 120 | 870 | 3000 | 3400 |
| 123 | 260 | 1400 | 1600 |
| 124 | 220 | 1700 | 2200 |
| 125 | 210 | 4700 | >10000 |
| 126 | 820 | >10000 | >10000 |
| 127 | 590 | >10000 | >10000 |
| 128 | 760 | 8500 | >10000 |
| 131 | 310 | 2200 | 4700 |
| 132 | 790 | >10000 | >10000 |
| 133 | 2900 | >10000 | >10000 |
| 135 | 68 | 2400 | 3700 |
| 136 | 490 | 1400 | 3500 |
| 137 | 640 | 1400 | 4200 |
| 138 | 650 | 2000 | 4300 |
| 139 | 43 | 2900 | 2100 |
| 140 | 280 | 770 | 340 |
| 141 | 1100 | >10000 | >10000 |
| 142 | 1200 | >10000 | >10000 |
| 143 | 1900 | >10000 | >10000 |
| 144 | 480 | >10000 | 6600 |
| 145 | 270 | 1200 | 1400 |
| 146 | 270 | 1600 | 1400 |
| 147 | 2600 | >10000 | >10000 |

TABLE 5

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
|---|---|---|---|
| 148 | 1600 | >10000 | >10000 |
| 149 | 1000 | >10000 | >10000 |
| 150 | 5200 | >10000 | >10000 |
| 151 | 2600 | >10000 | >10000 |
| 152 | 2300 | >10000 | >10000 |
| 153 | 210 | 7200 | 9000 |
| 154 | 180 | 5300 | 3100 |
| 155 | 24 | 4600 | 1400 |
| 156 | 820 | >10000 | 10000 |
| 157 | 310 | 5100 | >10000 |
| 158 | 1300 | >10000 | >10000 |
| 159 | 2600 | >10000 | >10000 |
| 160 | 980 | >10000 | >10000 |
| 161 | 47 | >10000 | >10000 |
| 162 | 1100 | >10000 | >10000 |
| 163 | 450 | >10000 | 5600 |
| 164 | 2600 | >10000 | >10000 |
| 165 | 40 | >10000 | 1200 |
| 166 | 280 | 10000 | 1300 |
| 167 | 230 | 9500 | 1100 |
| 168 | 1200 | >10000 | 3200 |
| 169 | 160 | 6400 | 2100 |
| 170 | 1600 | >10000 | >10000 |
| 171 | 850 | >10000 | >10000 |
| 172 | 320 | >10000 | >10000 |
| 173 | 3400 | >10000 | >10000 |
| 174 | 300 | >10000 | 5600 |
| 175 | 96 | >10000 | >10000 |
| 176 | 78 | 4400 | 4600 |
| 177 | 300 | >10000 | >10000 |

TABLE 6

| Test Compound (Example) | JAK1 Inhibitory Activity ($IC_{50}$: nM) | JAK2 Inhibitory Activity ($IC_{50}$: nM) | JAK3 Inhibitory Activity ($IC_{50}$: nM) |
|---|---|---|---|
| 178 | 510 | >10000 | 9500 |
| 179 | 320 | >10000 | >10000 |
| 180 | 560 | >10000 | >10000 |
| 181 | 860 | >10000 | >10000 |
| 182 | 88 | 5400 | 1700 |
| 183 | 87 | >10000 | 1200 |
| 184 | 62 | >10000 | 470 |
| 185 | 190 | >10000 | 810 |
| 186 | 81 | >10000 | 580 |
| 187 | 68 | 2100 | 1800 |
| 188 | 1300 | >10000 | >10000 |
| 189 | 1100 | >10000 | >10000 |
| 190 | 65 | 6600 | 1000 |
| 191 | 52 | >10000 | >10000 |
| 192 | 690 | >10000 | >10000 |
| 193 | 470 | >10000 | >10000 |
| 194 | 260 | >10000 | >10000 |
| 195 | 310 | 9000 | 4900 |
| 196 | 110 | 9100 | 7300 |
| 197 | 120 | 8200 | 3800 |
| 198 | 1500 | >10000 | >10000 |
| 199 | 2800 | >10000 | >10000 |
| 200 | 2400 | >10000 | >10000 |
| 201 | 120 | >10000 | >10000 |
| 202 | 300 | >10000 | >10000 |
| 203 | 70 | >10000 | >10000 |
| 204 | 2700 | >10000 | >10000 |
| 205 | 850 | >10000 | >10000 |
| 206 | 940 | >10000 | >10000 |
| 207 | 410 | >10000 | >10000 |

Test Example 2

Inhibitory Effect on *Aspergillus*-induced Airway Inflammation Model

*Aspergillus fumigatus* extracts (Greer laboratories, Inc.) were adjusted to 400 μg/mL with PBS. The *Aspergillus fumigatus* solutions thus prepared were administered to mice as nasal drops (50 μL) on Day 0, Day 1, Day 7 and Day 8. The nasal drop was administered one hour after the administration of test compounds in the morning. The test compound was administered twice a day in the morning and evening of Day 0 to Day 9. The test compound was suspended in 0.5% methylcellulose at 10 mg/mL, and orally administered at the dosage of 10 mL/kg. The bronchoalveolar lavage fluid (BALF) was collected at Day 10, and the total white blood cell count in BALF was measured using Celltac (NIHON KOHDEN). The ratio of eosinophil in total white blood cell was calculated using ADVIA 120 (Siemens Healthcare Diagnostics), and the ratio was multiplied by the total white blood cell count to determine the eosinophil count in BALF. The inhibition rate of the test compound was determined, assuming the inhibitory ratio in the treatment with *Aspergillus fumigatus* extract and 0.5% methylcellulose as 0% and the inhibitory ratio in the treatment without *Aspergillus fumigatus* extract but with 0.5% methylcellulose as 100%. The results are shown in Table 7.

TABLE 7

| Test Compound (Example) | Inhibition rate on count of invasive eosinophil in BALF (%) |
|---|---|
| 1 | 43 |
| 16 | 33 |
| 20 | 61 |

TABLE 7-continued

| Test Compound (Example) | Inhibition rate on count of invasive eosinophil in BALF (%) |
|---|---|
| 21 | 47 |
| 22 | 57 |
| 23 | 31 |
| 24 | 35 |
| 25 | 30 |
| 26 | 58 |
| 27 | 62 |
| 28 | 52 |
| 33 | 37 |
| 41 | 51 |
| 58 | 37 |
| 62 | 36 |
| 73 | 64 |
| 74 | 34 |
| 81 | 43 |
| 87 | 24 |
| 96 | 51 |
| 97 | 43 |
| 125 | 35 |
| 126 | 57 |
| 127 | 38 |

As seen in Table 7, the compounds of the invention have a significant effect on this in vivo inflammation model.

By using the compounds shown above in Table 7, the following tests (Test Examples 3 and 4) were conducted.

Test Example 3

Inhibitory Effect on IL-4 Stimulated STAT6 Phosphorylation

1. Preparation of Test Compound

The test compound was dissolved in dimethyl sulfoxide (DMSO) to 10 mM, and further diluted with DMSO to the concentrations of 300 and 100 μM. The solution was further diluted with RPMI 1640 medium to 100-fold to obtain a sample solution. Also, DMSO was diluted to 100-fold with RPMI 1640 medium and was used as a negative control.

2. Phosphorylated STAT6 Activity

The sample solution or the negative control solution (50 μL) was mixed with a solution of DND39 cell (400 μL) (Cell number: $10^5$ cells) and shaken at 37° C. for 30 min. 50 μL of Interleukin-4 (10 ng/mL) was added as a stimulant, and the mixture was shaken for 15 min. 500 μL of Fixation buffer (BD Biosciences, Inc.) was added to the mixture, and the mixture was shaken for 10 min to stop the reaction. After centrifuge and removing the supernatant, 500 μL of a membrane-permeabilizing agent Perm buffer III (BD Biosciences, Inc.) was added to the pellet, and incubation was conducted at 4° C. for 30 min. After washing twice with a stain buffer (BD Biosciences, Inc.), Alexa Fluor 647 Mouse Anti-Stat6 (pY641) (BD Biosciences, Inc.) was added, and incubation was conducted in a cool dark place for 30 min. The obtained cell solution was subjected to a flow cytometer. The inhibition activity of the test compound was calculated, assuming the GEOMEAN value of the interleukin-4 stimulated negative control group fluorescence intensity as the inhibitory ratio of 0% and the GEOMEAN value of the non-stimulated negative control group fluorescence intensity as the inhibitory ratio of 100%. From the results, it was confirmed that the test compounds suppressed IL-4 signaling.

Test Example 4

Inhibitory Effect on IL-7 Stimulated STAT5 Phosphorylation

1. Preparation of Test Compound

The test compound was dissolved in dimethyl sulfoxide (DMSO) to 10 mM and further diluted with RPMI 1640 medium to 100-fold to prepare a sample solution. Also, DMSO was diluted with RPMI 1640 medium to 100-fold and was used as a negative control.

2. Phosphorylated STAT5 Activity

To 100 μL of human fresh blood was added 10 μL of the sample solution or the negative control solution, and shaken at 37° C. for 30 min. 10 μL of interleukin-7 (100 ng/mL) was added as a stimulant, and the mixture was shaken for 15 min. 1.4 mL of Lyse/fix buffer (BD Biosciences, Inc.), which was diluted to 5-fold by distilled water, was added to the reaction system. The mixture was shaken for 10 min, and centrifuged to separate cells. After removing the supernatant, 1 mL of PBS was added to the pellet. After centrifuging to remove PBS, 500 μL of Perm buffer III (BD Biosciences, Inc.) was added, and incubation was conducted at 4° C. for 30 min. After washing twice with Stain buffer (BD Biosciences, Inc.), Alexa Fluor 647 Mouse Anti-Stat5 antibody (pY694) (BD Biosciences, Inc.) was added, and incubation was conducted in a cool dark place for 30 min. The obtained cell solution was subjected to a flow cytometer. The inhibition activity of the test compound was calculated, assuming the GEOMEAN value of the IL-7 stimulated negative control group fluorescence intensity as the inhibitory ratio of 0% and the GEOMEAN value of the non-stimulated negative control group fluorescence intensity as the inhibitory ratio of 100%. From the result, it was confirmed that the test compounds suppressed IL-7 signaling.

As shown in Test Examples 1 to 4, the compound of the invention showed JAK1 inhibitory activity, and thus, is effective in in vivo inflammation model.

INDUSTRIAL APPLICABILITY

In view of the fact that the compound of the invention or a pharmaceutically acceptable salt thereof exhibits JAK1 inhibitory activity, it is useful as a therapeutic agent for an autoimmune disease (e.g., rheumatoid arthritis, psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (e.g., Takayasu's arteritis, giant cell arteritis, microscopic polyangiitis, granulomatosis with polyangiitis and eosinophilic granulomatosis with polyangiitis), dermatomyositis, polymyositis and neuromyelitis optica), inflammatory diseases (e.g., atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (e.g., solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection.

Formulation Example 1

Tablet (Oral Tablet)
In an 80 mg tablet of the formulation:

| | |
|---|---|
| Compound of Example 1 | 5.0 mg |
| Corn starch | 46.6 mg |
| Crystalline cellulose | 24.0 mg |
| Methylcellulose | 4.0 mg |
| Magnesium stearate | 0.4 mg |

According to a conventional method, a mixed powder of the components was tableted to form an oral tablet.

What is claimed is:

1. A pyrazolothiazole compound selected from the group consisting of
   N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide,
   N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide,
   methyl (1-{[6-{[(1S)-1-cyclopropylethyl]amino-}2-(pyrazolo[5,1-b][1,3]thiazol-7-yl)pyrimidin-4-yl]carbonyl}piperidin-4-yl)carbamate,
   ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate,
   methyl [1-({6-[(2S)-butan-2-ylamino]-2-(pyrazolo[5,1-b][1,3]thiazol-7-yl)pyrimidin-4-yl}carbonyl)piperidin-4-yl]carbamate, and
   methyl [1-({6-[(2R)-butan-2-ylamino]-2-(pyrazolo[5,1-b][1,3]thiazol-7-yl)pyrimidin-4-yl}carbonyl)piperidin-4-yl]carbamate,
or a pharmaceutically acceptable salt thereof, or a solvate thereof.

2. A pharmaceutical composition comprising:
   the pyrazolothiazole compound or a pharmaceutically acceptable salt thereof or a solvate thereof according to claim 1 as an active ingredient; and
   one or more pharmaceutically acceptable nontoxic and inactive carrier(s).

3. A method for treating an inflammatory disease, comprising the step of administering the pyrazolothiazole compound or a pharmaceutically acceptable salt thereof or a solvate thereof according to claim 1 as an active ingredient, wherein the inflammatory disease is atopic dermatitis, bronchial asthma, eosinophilic pneumonia, chronic obstructive pulmonary disease, eosinophilic sinusitis, nasal polyp, or eosinophilic esophagitis.

4. A method for treating an autoimmune disease, comprising the step of administering the pyrazolothiazole compound or a pharmaceutically acceptable salt thereof or a solvate thereof according to claim 1 as an active ingredient, wherein the autoimmune disease is rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis or neuromyelitis optica.

5. A method for treating a proliferative disease, comprising the step of administering the pyrazolothiazole compound or a pharmaceutically acceptable salt thereof or a solvate thereof according to claim 1 as an active ingredient, wherein the proliferative disease is eosinophilia.

6. A method for treating bone marrow transplant rejection, comprising the step of administering the pyrazolothiazole compound or a pharmaceutically acceptable salt thereof or a solvate thereof according to claim 1 as an active ingredient.

* * * * *